US009844587B2

(12) United States Patent
Tuomanen et al.

(10) Patent No.: US 9,844,587 B2
(45) Date of Patent: Dec. 19, 2017

(54) METHODS AND COMPOSITIONS EMPLOYING IMMUNOGENIC FUSION PROTEINS

(71) Applicant: St. Jude Children's Research Hospital, Memphis, TN (US)

(72) Inventors: Elaine Tuomanen, Brownsville, TN (US); Elizabeth R. Mann, Germantown, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 4 days.

(21) Appl. No.: 14/877,322

(22) Filed: Oct. 7, 2015

(65) Prior Publication Data

US 2016/0022799 A1     Jan. 28, 2016

Related U.S. Application Data

(62) Division of application No. 14/007,159, filed as application No. PCT/US2012/030241 on Mar. 23, 2012, now Pat. No. 9,181,308.

(60) Provisional application No. 61/468,407, filed on Mar. 28, 2011.

(51) Int. Cl.
| | |
|---|---|
| A61K 39/02 | (2006.01) |
| A61K 39/09 | (2006.01) |
| C07K 14/315 | (2006.01) |
| C07K 14/47 | (2006.01) |
| A61K 39/00 | (2006.01) |

(52) U.S. Cl.
CPC ........ *A61K 39/092* (2013.01); *C07K 14/3156* (2013.01); *C07K 14/47* (2013.01); *A61K 2039/543* (2013.01); *A61K 2039/545* (2013.01); *A61K 2039/55505* (2013.01); *A61K 2039/55544* (2013.01); *A61K 2039/55583* (2013.01); *A61K 2039/575* (2013.01); *A61K 2039/6068* (2013.01); *A61K 2039/645* (2013.01); *C07K 2319/00* (2013.01); *C07K 2319/40* (2013.01)

(58) Field of Classification Search
None
See application file for complete search history.

(56) References Cited

U.S. PATENT DOCUMENTS

| | | |
|---|---|---|
| 2009/0170162 A1 | 7/2009 | Hollingshead et al. |
| 2009/0285846 A1 | 11/2009 | Tweten |
| 2010/0143394 A1 | 6/2010 | El Kasmi et al. |
| 2010/0166795 A1 | 7/2010 | Mitchell et al. |

FOREIGN PATENT DOCUMENTS

WO    WO 2008/039838 A2    4/2008

OTHER PUBLICATIONS

Daniels, C., et al., "The Proline-Rich Region of Pneumococcal Surface Proteins A and C Contains Surface-Accessible Epitopes Common to All Pneumococci and Elicits Antibody-Mediated Protection against Sepsis," *Infection and Immunity*, 2010, vol. 78(5), pp. 2163-2172.
Douce, G., et al., "Novel mucosal vaccines generated by genetic conjugation of heterologous proteins to pneumolysin (PLY) from *Streptococcus pneumoniae*," *Vaccine*, 2010, vol. 28, pp. 3231-3237.
Greenspan, N., et al., "Defining epitopes: It's not as easy as it seems," *Nature Biotechnology*, 1999, vol. 17, pp. 936-937.
Lu, L., et al., "*Streptococcus pneumoniae* Recruits Complement Factor H through the Amino Terminus of CbpA," *The Journal of Biological Chemistry*, 2006, vol. 281(22), pp. 15464-15474.
Luo, R., et al., "Solution structure of choline binding protein A, the major adhesin of *Streptococcus pneumoniae*," *The EMBO Journal*, 2005, vol. 24(1), pp. 34-43.
Ogunniyi, A., et al., "Protection against *Streptococcus pneumoniae* Elicited by Immunization with Pneumolysin and CbpA," *Infection and Immunity*, 2001, vol. 69(10), pp. 5997-6003.

*Primary Examiner* — J. Hines
*Assistant Examiner* — Khatol Shahnan Shah
(74) *Attorney, Agent, or Firm* — Womble Bond Dickinson (US) LLP

(57) ABSTRACT

Compositions and methods are provided for the prevention and treatment of bacterial infections, including pneumococcal infections. Compositions provided herein comprise a variety of immunogenic fusion proteins, wherein at least one polypeptide component of a given fusion protein comprises a CbpA polypeptide and/or a cytolysoid polypeptide, or an active variant or fragment thereof. Methods are provided for the prevention and treatment of bacterial infections, including pneumococcal infections by employing the various immunogenic fusion proteins having at least one polypeptide component comprising a CbpA polypeptide and/or a cytolysoid polypeptide, or an active variant or fragment thereof.

10 Claims, 27 Drawing Sheets

Figure 2. Structure of the R2 polypeptide region of CbpA*

A) Linear representation of the CbpA R2 domain sequence
B) Experimentally determined tertiary structure of the R2 domain; spirals represent alpha helices; boxes indicate nonhelical loops known to be critical to bioactivities of CbpA Figure 3
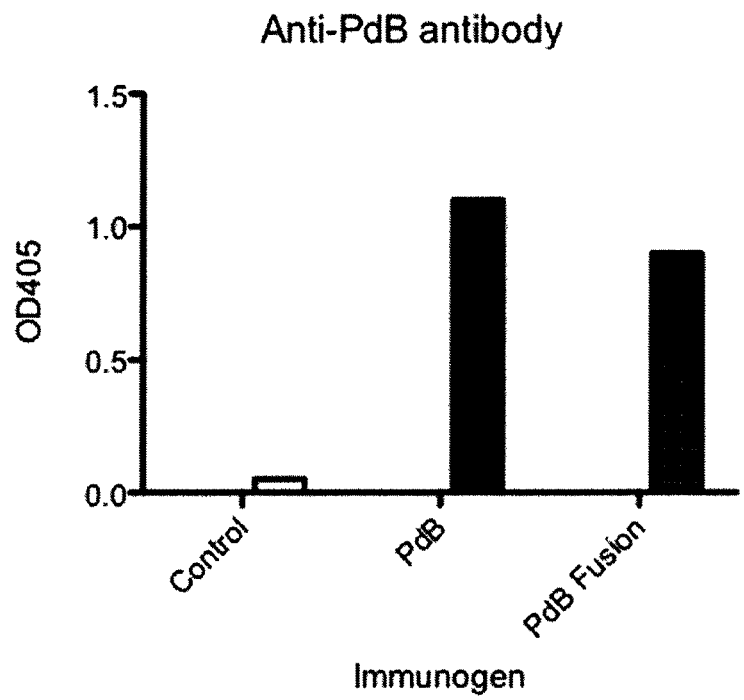
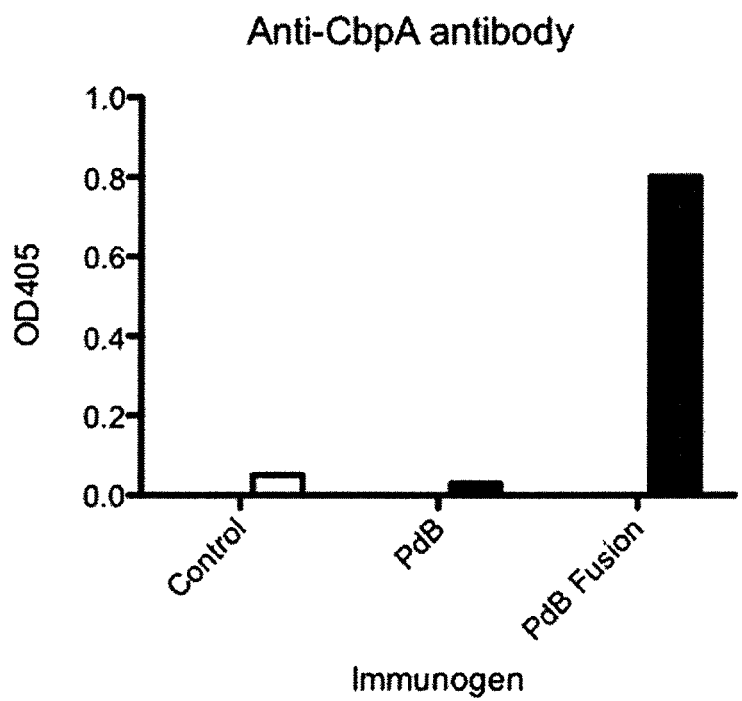

Figure 8
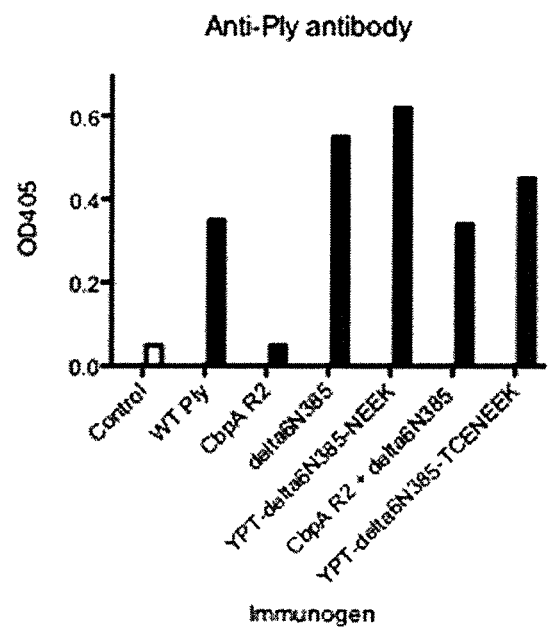
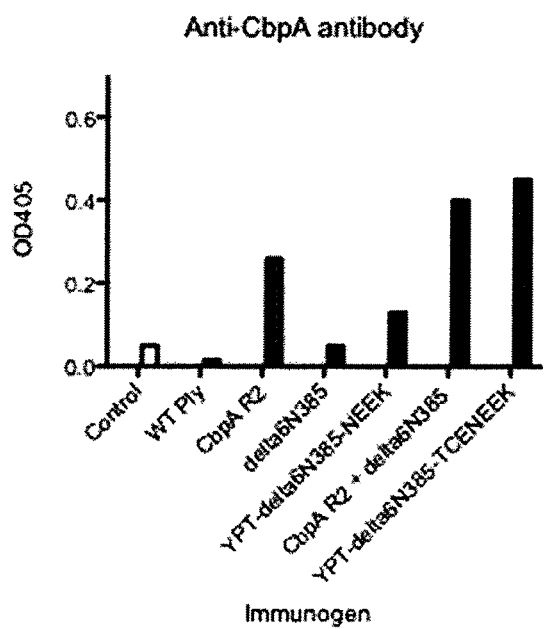

Figure 10
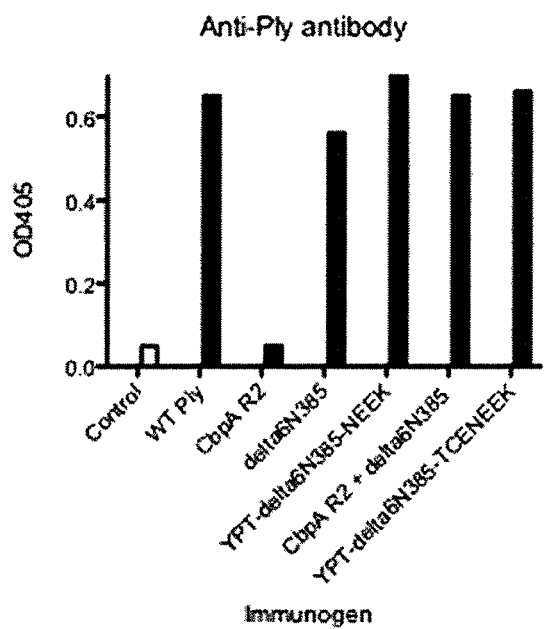
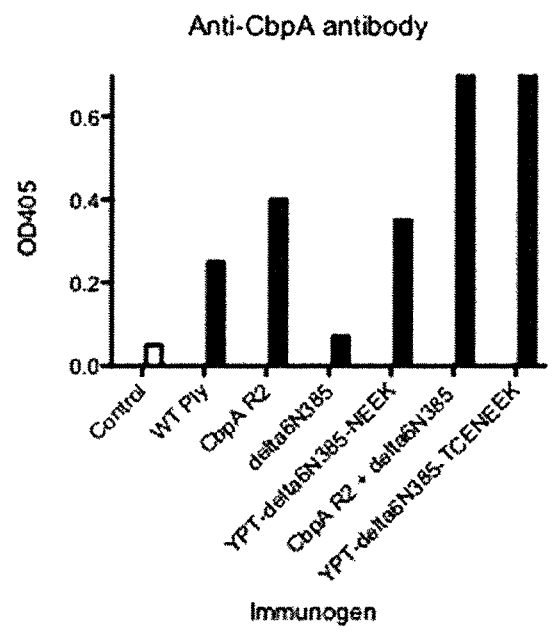

Figure 12
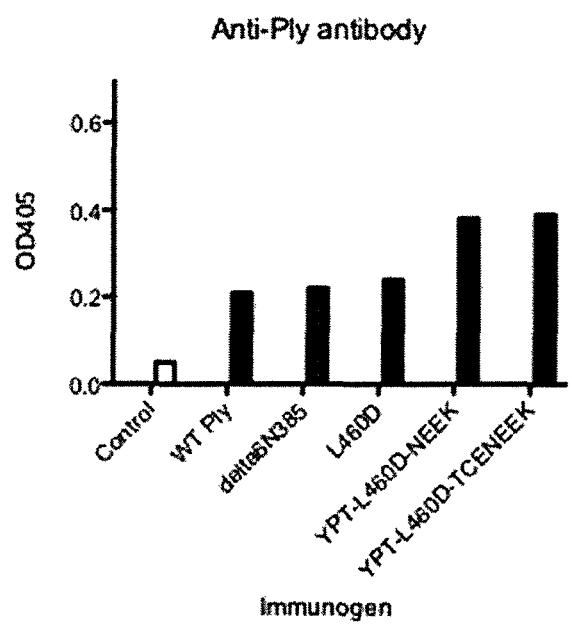
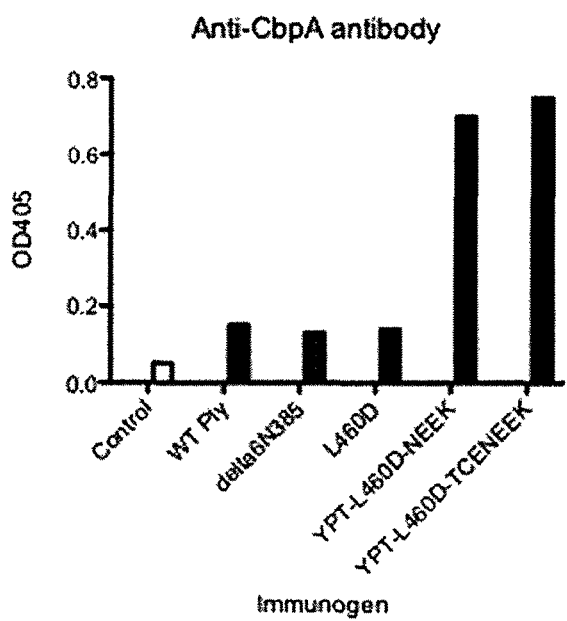

Figure 18

Fusion is protective against development of meningitis compared
To toxoid alone or negative control Figure 19
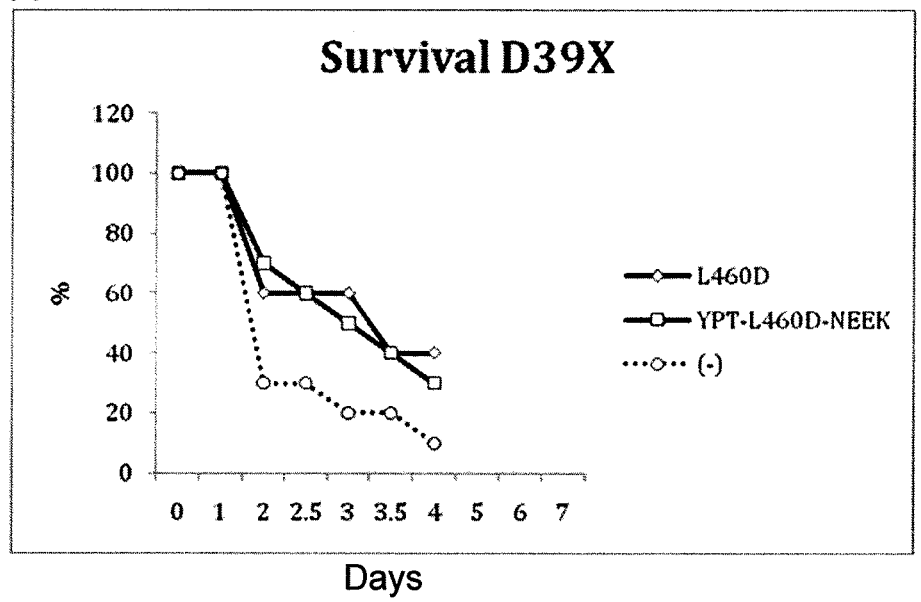
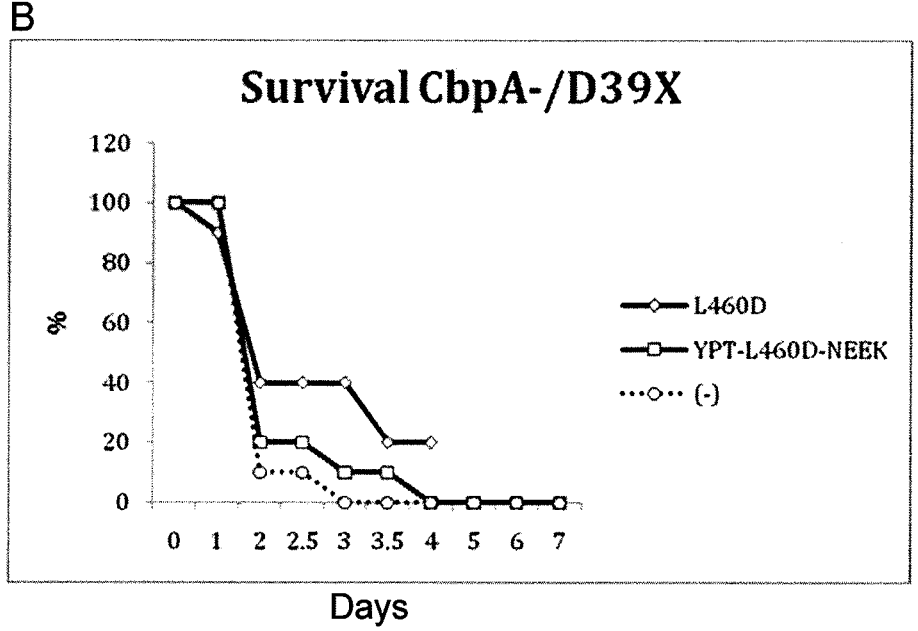

Figure 21

|  | % Survival | % Meningitis |
|---|---|---|
| L460D | 59-80% | 20-29% |
| YPT L460D NEEK | 85-94%* | 5-15%* |
| L460D NEEK | 75% | 10% |

* = significantly different from no immunogen control

The percent of mice that developed meningitis is as follows: L460D (36%), YPT-L460D-NEEK (15%) and Alum (62%).

Black line = mean
0 days = never develop meningitis

***The percent survival of L460D (62%) was significantly higher than Alum (28%) with a p value=0.0004 as was the YPT-L460D-NEEK (70%) mice with a p value<0.0001.

Black line = mean

0= never develop meningitis
black line= mean

SEQUENCE LISTING

<160> NUMBER OF SEQ ID NOS: 39

<210> SEQ ID NO 1

-continued

```
<211> LENGTH: 30
<212> TYPE: PRT
<213> ORGANISM: Streptococcus pneumoniae

<400> SEQUENCE: 1

Ala Val Lys Lys Ala Glu Asp Gln Lys Glu Glu Asp Arg Arg Asn Tyr
 1               5                  10                  15

Pro Thr Asn Thr Tyr Lys Thr Leu Glu Leu Glu Lys Ala Glu
             20                  25                  30

<210> SEQ ID NO 2
<211> LENGTH: 17
<212> TYPE: PRT
<213> ORGANISM: Streptococcus pneumoniae

<400> SEQUENCE: 2

Lys Glu Lys Ala Lys Glu Pro Arg Asn Glu Glu Lys Val Lys Gln Val
 1               5                  10                  15

Lys

<210> SEQ ID NO 3
<211> LENGTH: 30
<212> TYPE: PRT
<213> ORGANISM: Artificial Sequence
<220> FEATURE:
<223> OTHER INFORMATION: Cysteine mutant of R21 fragment of
      Streptococcus pneumoniae

<400> SEQUENCE: 3

Ala Cys Lys Lys Ala Glu Asp Gln Lys Glu Glu Asp Arg Arg Asn Tyr
 1               5                  10                  15

Pro Thr Asn Thr Tyr Lys Thr Leu Glu Leu Glu Cys Ala Glu
             20                  25                  30

<210> SEQ ID NO 4
<211> LENGTH: 17
<212> TYPE: PRT
<213> ORGANISM: Artificial Sequence
<220> FEATURE:
<223> OTHER INFORMATION: Cysteine mutant of R22 fragment of
      Streptococcus pneumoniae

<400> SEQUENCE: 4

Lys Glu Cys Ala Lys Glu Pro Arg Asn Glu Glu Lys Val Lys Gln Cys
 1               5                  10                  15

Lys

<210> SEQ ID NO 5
<211> LENGTH: 471
<212> TYPE: PRT
<213> ORGANISM: Streptococcus pneumoniae

<400> SEQUENCE: 5

Met Ala Asn Lys Ala Val Asn Asp Phe Ile Leu Ala Met Asn Tyr Asp
 1               5                  10                  15

Lys Lys Lys Leu Leu Thr His Gln Gly Glu Ser Ile Glu Asn Arg Phe
             20                  25                  30

Ile Lys Glu Gly Asn Gln Leu Pro Asp Glu Phe Val Val Ile Glu Arg
                 35                  40                  45

Lys Lys Arg Ser Leu Ser Thr Asn Thr Ser Asp Ile Ser Val Thr Ala
         50                  55                  60

Thr Asn Asp Ser Arg Leu Tyr Pro Gly Ala Leu Leu Val Val Asp Glu
```

```
             65                  70                  75                  80
        Thr Leu Leu Glu Asn Asn Pro Thr Leu Leu Ala Val Asp Arg Ala Pro
                         85                  90                  95
        Met Thr Tyr Ser Ile Asp Leu Pro Gly Leu Ala Ser Ser Asp Ser Phe
                        100                 105                 110
        Leu Gln Val Glu Asp Pro Ser Asn Ser Ser Val Arg Gly Ala Val Asn
                    115                 120                 125
        Asp Leu Leu Ala Lys Trp His Gln Asp Tyr Gly Gln Val Asn Asn Val
                130                 135                 140
        Pro Ala Arg Met Gln Tyr Glu Lys Ile Thr Ala His Ser Met Glu Gln
        145                 150                 155                 160
        Leu Lys Val Lys Phe Gly Ser Asp Phe Glu Lys Thr Gly Asn Ser Leu
                        165                 170                 175
        Asp Ile Asp Phe Asn Ser Val His Ser Gly Glu Lys Gln Ile Gln Ile
                        180                 185                 190
        Val Asn Phe Lys Gln Ile Tyr Tyr Thr Val Ser Val Asp Ala Val Lys
                    195                 200                 205
        Asn Pro Gly Asp Val Phe Gln Asp Thr Val Thr Val Glu Asp Leu Lys
        210                 215                 220
        Gln Arg Gly Ile Ser Ala Glu Arg Pro Leu Val Tyr Ile Ser Ser Val
        225                 230                 235                 240
        Ala Tyr Gly Arg Gln Val Tyr Leu Lys Leu Glu Thr Thr Ser Lys Ser
                        245                 250                 255
        Asp Glu Val Glu Ala Ala Phe Glu Ala Leu Ile Lys Gly Val Lys Val
                    260                 265                 270
        Ala Pro Gln Thr Glu Trp Lys Gln Ile Leu Asp Asn Thr Glu Val Lys
                275                 280                 285
        Ala Val Ile Leu Gly Gly Asp Pro Ser Ser Gly Ala Arg Val Val Thr
                290                 295                 300
        Gly Lys Val Asp Met Val Glu Asp Leu Ile Gln Glu Gly Ser Arg Phe
        305                 310                 315                 320
        Thr Ala Asp His Pro Gly Leu Pro Ile Ser Tyr Thr Thr Ser Phe Leu
                        325                 330                 335
        Arg Asp Asn Val Val Ala Thr Phe Gln Asn Ser Thr Asp Tyr Val Glu
                    340                 345                 350
        Thr Lys Val Thr Ala Tyr Arg Asn Gly Asp Leu Leu Leu Asp His Ser
                355                 360                 365
        Gly Ala Tyr Val Ala Gln Tyr Tyr Ile Thr Trp Asp Glu Leu Ser Tyr
            370                 375                 380
        Asp His Gln Gly Lys Glu Val Leu Thr Pro Lys Ala Trp Asp Arg Asn
        385                 390                 395                 400
        Gly Gln Asp Leu Thr Ala His Phe Thr Thr Ser Ile Pro Leu Lys Gly
                        405                 410                 415
        Asn Val Arg Asn Leu Ser Val Lys Ile Arg Glu Cys Thr Gly Leu Ala
                    420                 425                 430
        Trp Glu Trp Trp Arg Thr Val Tyr Glu Lys Thr Asp Leu Pro Leu Val
                435                 440                 445
        Arg Lys Arg Thr Ile Ser Ile Trp Gly Thr Thr Leu Tyr Pro Gln Val
                450                 455                 460
        Glu Asp Lys Val Glu Asn Asp
        465                 470

<210> SEQ ID NO 6
```

<211> LENGTH: 1413
<212> TYPE: DNA
<213> ORGANISM: Streptococcus pneumoniae

<400> SEQUENCE: 6

```
atggcaaata aagcagtaaa tgactttata ctagctatga attacgataa aaagaaactc      60
ttgacccatc agggagaaag tattgaaaat cgtttcatca agagggtaa tcagctaccc     120
gatgagtttg ttgttatcga agaaagaag cggagcttgt cgacaaatac aagtgatatt     180
tctgtaacag ctaccaacga cagtcgcctc tatcctggag cacttctcgt agtggatgag     240
accttgttag agaataatcc cactcttctt gcggttgatc gtgctccgat gacttatagt     300
attgatttgc ctggtttggc aagtagcgat agctttctcc aagtggaaga ccccagcaat     360
tcaagtgttc gcggagcggt aaacgatttg ttggctaagt ggcatcaaga ttatggtcag     420
gtcaataatg tcccagctag aatgcagtat gaaaaaataa cggctcacag catggaacaa     480
ctcaaggtca agtttggttc tgactttgaa aagacaggga attctcttga tattgatttt     540
aactctgtcc attcaggtga aaagcagatt cagattgtta attttaagca gatttattat     600
acagtcagcg tagacgctgt taaaaatcca ggagatgtgt tcaagatac tgtaacggta     660
gaggatttaa aacagagagg aatttctgca gagcgtcctt tggtctatat ttcgagtgt    720
gcttatgggc gccaagtcta tctcaagttg gaaaccacga gtaagagtga tgaagtagag     780
gctgcttttg aagctttgat aaaaggagtc aaggtagctc ctcagacaga gtggaagcag     840
attttggaca atacagaagt gaaggcggtt attttagggg gcgacccaag ttcgggtgcc    900
cgagttgtaa caggcaaggt ggatatggta gaggacttga ttcaagaagg cagtcgcttt     960
acagcagatc atccaggctt gccgatttcc tatacaactt cttttttacg tgacaatgta    1020
gttgcgacct tcaaaacag tacagactat gttgagacta aggttacagc ttacagaaac    1080
ggagatttac tgctggatca tagtggtgcc tatgttgccc aatattatat tacttgggat    1140
gaattatcct atgatcatca aggtaaggaa gtcttgactc ctaaggcttg ggacagaaat    1200
gggcaggatt tgacggctca ctttaccact agtattcctt aaaagggaa tgttcgtaat    1260
ctctctgtca aaattagaga gtgtaccggg cttgcctggg aatggtggcg tacggtttat    1320
gaaaaaaccg atttgccact agtgcgtaag cggacgattt ctatttgggg aacaactctc    1380
tatcctcagg tagaggataa ggtagaaaat gac                                  1413
```

<210> SEQ ID NO 7
<211> LENGTH: 471
<212> TYPE: PRT
<213> ORGANISM: Artificial Sequence
<220> FEATURE:
<223> OTHER INFORMATION: L460D pneumolysin mutant

<400> SEQUENCE: 7

Met Ala Asn Lys Ala Val Asn Asp Phe Ile Leu Ala Met Asn Tyr Asp
1 5 10 15

Lys Lys Lys Leu Leu Thr His Gln Gly Glu Ser Ile Glu Asn Arg Phe
20 25 30

Ile Lys Glu Gly Asn Gln Leu Pro Asp Glu Phe Val Val Ile Glu Arg
35 40 45

Lys Lys Arg Ser Leu Ser Thr Asn Thr Ser Asp Ile Ser Val Thr Ala
50 55 60

Thr Asn Asp Ser Arg Leu Tyr Pro Gly Ala Leu Leu Val Val Asp Glu
65 70 75 80

```
Thr Leu Leu Glu Asn Asn Pro Thr Leu Leu Ala Val Asp Arg Ala Pro
             85                  90                  95

Met Thr Tyr Ser Ile Asp Leu Pro Gly Leu Ala Ser Ser Asp Ser Phe
        100                 105                 110

Leu Gln Val Glu Asp Pro Ser Asn Ser Ser Val Arg Gly Ala Val Asn
    115                 120                 125

Asp Leu Leu Ala Lys Trp His Gln Asp Tyr Gly Gln Val Asn Asn Val
130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Ser Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Asp Tyr Pro Gln Val
    450                 455                 460

Glu Asp Lys Val Glu Asn Asp
465                 470

<210> SEQ ID NO 8
<211> LENGTH: 469
<212> TYPE: PRT
```

<213> ORGANISM: Artificial Sequence
<220> FEATURE:
<223> OTHER INFORMATION: Delta6N385 pneumolysin mutant

<400> SEQUENCE: 8

```
Met Ala Asn Lys Ala Val Asn Asp Phe Ile Leu Ala Met Asn Tyr Asp
1               5

```
                385                 390                 395                 400
Asp Leu Thr Ala His Phe Thr Thr Ser Ile Pro Leu Lys Gly Asn Val
                    405                 410                 415

Arg Asn Leu Ser Val Lys Ile Arg Glu Cys Thr Gly Leu Ala Trp Glu
                420                 425                 430

Trp Trp Arg Thr Val Tyr Glu Lys Thr Asp Leu Pro Leu Val Arg Lys
                435                 440                 445

Arg Thr Ile Ser Ile Trp Gly Thr Thr Leu Tyr Pro Gln Val Glu Asp
            450                 455                 460

Lys Val Glu Asn Asp
465

<210> SEQ ID NO 9
<211> LENGTH: 520
<212> TYPE: PRT
<213> ORGANISM: Artificial Sequence
<220> FEATURE:
<223> OTHER INFORMATION: YPT-L460D-NEEK fusion protein

<400> SEQUENCE: 9

Met Ala Cys Lys Lys Ala Glu Asp Gln Lys Glu Asp Arg Arg Asn
1               5                   10                  15

Tyr Pro Thr Asn Thr Tyr Lys Thr Leu Glu Leu Glu Cys Ala Glu Gly
                20                  25                  30

Gly Ala Asn Lys Ala Val Asn Asp Phe Ile Leu Ala Met Asn Tyr Asp
            35                  40                  45

Lys Lys Lys Leu Leu Thr His Gln Gly Glu Ser Ile Glu Asn Arg Phe
        50                  55                  60

Ile Lys Glu Gly Asn Gln Leu Pro Asp Glu Phe Val Val Ile Glu Arg
65                  70                  75                  80

Lys Lys Arg Ser Leu Ser Thr Asn Thr Ser Asp Ile Ser Val Thr Ala
                85                  90                  95

Thr Asn Asp Ser Arg Leu Tyr Pro Gly Ala Leu Leu Val Val Asp Glu
                100                 105                 110

Thr Leu Leu Glu Asn Asn Pro Thr Leu Leu Ala Val Asp Arg Ala Pro
            115                 120                 125

Met Thr Tyr Ser Ile Asp Leu Pro Gly Leu Ala Ser Ser Asp Ser Phe
        130                 135                 140

Leu Gln Val Glu Asp Pro Ser Asn Ser Ser Val Arg Gly Ala Val Asn
145                 150                 155                 160

Asp Leu Leu Ala Lys Trp His Gln Asp Tyr Gly Gln Val Asn Asn Val
                165                 170                 175

Pro Ala Arg Met Gln Tyr Glu Lys Ile Thr Ala His Ser Met Glu Gln
                180                 185                 190

Leu Lys Val Lys Phe Gly Ser Asp Phe Glu Lys Thr Gly Asn Ser Leu
            195                 200                 205

Asp Ile Asp Phe Asn Ser Val His Ser Gly Glu Lys Gln Ile Gln Ile
        210                 215                 220

Val Asn Phe Lys Gln Ile Tyr Tyr Thr Val Ser Val Asp Ala Val Lys
225                 230                 235                 240

Asn Pro Gly Asp Val Phe Gln Asp Thr Val Thr Val Glu Asp Leu Lys
                245                 250                 255

Gln Arg Gly Ile Ser Ala Glu Arg Pro Leu Val Tyr Ile Ser Ser Val
                260                 265                 270

Ala Tyr Gly Arg Gln Val Tyr Leu Lys Leu Glu Thr Thr Ser Lys Ser
```

-continued

```
            275                 280                 285
Asp Glu Val Glu Ala Ala Phe Glu Ala Leu Ile Lys Gly Val Lys Val
    290                 295                 300
Ala Pro Gln Thr Glu Trp Lys Gln Ile Leu Asp Asn Thr Glu Val Lys
305                 310                 315                 320
Ala Val Ile Leu Gly Asp Pro Ser Ser Gly Ala Arg Val Thr
            325                 330                 335
Gly Lys Val Asp Met Val Glu Asp Leu Ile Gln Glu Gly Ser Arg Phe
            340                 345                 350
Thr Ala Asp His Pro Gly Leu Pro Ile Ser Tyr Thr Thr Ser Phe Leu
        355                 360                 365
Arg Asp Asn Val Val Ala Thr Phe Gln Asn Ser Thr Asp Tyr Val Glu
    370                 375                 380
Thr Lys Val Thr Ala Tyr Arg Asn Gly Asp Leu Leu Asp His Ser
385                 390                 395                 400
Gly Ala Tyr Val Ala Gln Tyr Tyr Ile Thr Trp Asp Glu Leu Ser Tyr
            405                 410                 415
Asp His Gln Gly Lys Glu Val Leu Thr Pro Lys Ala Trp Asp Arg Asn
            420                 425                 430
Gly Gln Asp Leu Thr Ala His Phe Thr Thr Ser Ile Pro Leu Lys Gly
        435                 440                 445
Asn Val Arg Asn Leu Ser Val Lys Ile Arg Glu Cys Thr Gly Leu Ala
    450                 455                 460
Trp Glu Trp Trp Arg Thr Val Tyr Glu Lys Thr Asp Leu Pro Leu Val
465                 470                 475                 480
Arg Lys Arg Thr Ile Ser Ile Trp Gly Thr Thr Asp Tyr Pro Gln Val
            485                 490                 495
Glu Asp Lys Val Glu Asn Asp Lys Glu Cys Ala Lys Gly Pro Arg Asn
            500                 505                 510
Glu Glu Lys Val Lys Gln Cys Lys
        515                 520

<210> SEQ ID NO 10
<211> LENGTH: 1566
<212> TYPE: DNA
<213> ORGANISM: Artificial Sequence
<220> FEATURE:
<223> OTHER INFORMATION: YPT-L460D-NEEK fusion protein nucleotide
      sequence

<400> SEQUENCE: 10
catatggctt gtaaaaaagc cgaggatcaa aaagaagaag atcgccgtaa ctacccaacc      60
aatacttaca aaacgcttga acttgaatgt gctgagggtg gtgcaaataa agcagtaaat     120
gactttatac tagctatgaa ttacgataaa aagaaactct tgacccatca gggagaaagt     180
attgaaaatc gtttcatcaa agagggtaat cagctacccg atgagtttgt tgttatcgaa     240
agaaagaagc ggagcttgtc gacaaataca agtgatattt ctgtaacagc taccaacgac     300
agtcgcctct atcctggagc acttctcgta gtggatgaga ccttgttaga gaataatccc     360
actcttcttg cggttgatcg tgctccgatg acttatagta ttgatttgcc tggtttggca     420
agtagcgata gctttctcca gtggaagac cccagcaatt caagtgttcg cggagcggta     480
aacgatttgt tggctaagtg gcatcaagat tatggtcagg tcaataatgt cccagctaga     540
atgcagtatg aaaaaataac ggctcacagc atggaacaac tcaaggtcaa gtttggttct     600
gactttgaaa agacagggaa ttctcttgat attgattta actctgtcca ttcaggtgaa     660
```

```
aagcagattc agattgttaa ttttaagcag atttattata cagtcagcgt agacgctgtt    720
aaaaatccag gagatgtgtt tcaagatact gtaacggtag aggatttaaa acagagagga    780
atttctgcag agcgtccttt ggtctatatt tcgagtgttg cttatgggcg ccaagtctat    840
ctcaagttgg aaaccacgag taagagtgat gaagtagagg ctgcttttga agctttgata    900
aaaggagtca aggtagctcc tcagacagag tggaagcaga ttttggacaa tacagaagtg    960
aaggcggtta ttttagggggg cgacccaagt tcgggtgccc gagttgtaac aggcaaggtg   1020
gatatggtag aggacttgat tcaagaaggc agtcgcttta cagcagatca tccaggcttg   1080
ccgatttcct atacaacttc tttttttacgt gacaatgtag ttgcgaccttt tcaaaacagt  1140
acagactatg ttgagactaa ggttacagct tacagaaacg agatttact gctggatcat    1200
agtggtgcct atgttgccca atattatatt acttgggatg aattatccta tgatcatcaa   1260
ggtaaggaag tcttgactcc taaggcttgg gacagaaatg ggcaggattt gacggctcac   1320
tttaccacta gtattccttt aaaagggaat gttcgtaatc tctctgtcaa aattagagag   1380
tgtaccgggc ttgcctggga atggtggcgt acggtttatg aaaaaaccga tttgccacta   1440
gtgcgtaagc ggacgatttc tatttgggga caactgact atcctcaggt agaggataag    1500
gtagaaaatg acaaagagtg tgctaaggaa cctcgaaacg aggaaaaagt taagcaatgt   1560
aaatag                                                              1566
```

<210> SEQ ID NO 11
<211> LENGTH: 518
<212> TYPE: PRT
<213> ORGANISM: Artificial Sequence
<220> FEATURE:
<223> OTHER INFORMATION: YPT-Delta6N385-NEEK fusion protein

<400> SEQUENCE: 11

Met Ala Cys Lys Lys Ala Glu Asp Gln Lys Glu Glu Asp Arg Arg Asn
1               5                   10                  15

Tyr Pro Thr Asn Thr Tyr Lys Thr Leu Glu Leu Glu Cys Ala Glu Gly
            20                  25                  30

Gly Ala Asn Lys Ala Val Asn Asp Phe Ile Leu Ala Met Asn Tyr Asp
        35                  40                  45

Lys Lys Lys Leu Leu Thr His Gln Gly Glu Ser Ile Glu Asn Arg Phe
    50                  55                  60

Ile Lys Glu Gly Asn Gln Leu Pro Asp Glu Phe Val Val Ile Glu Arg
65                  70                  75                  80

Lys Lys Arg Ser Leu Ser Thr Asn Thr Ser Asp Ile Ser Val Thr Ala
                85                  90                  95

Thr Asn Asp Ser Arg Leu Tyr Pro Gly Ala Leu Leu Val Val Asp Glu
            100                 105                 110

Thr Leu Leu Glu Asn Asn Pro Thr Leu Leu Ala Val Asp Arg Ala Pro
        115                 120                 125

Met Thr Tyr Ser Ile Asp Leu Pro Gly Leu Ala Ser Ser Asp Ser Phe
    130                 135                 140

Leu Gln Val Glu Asp Pro Ser Asn Ser Ser Val Arg Gly Ala Val Asn
145                 150                 155                 160

Asp Leu Leu Ala Lys Trp His Gln Asp Tyr Gly Gln Val Asn Asn Val
                165                 170                 175

Pro Met Gln Tyr Glu Lys Ile Thr Ala His Ser Met Glu Gln Leu Lys
            180                 185                 190

Val Lys Phe Gly Ser Asp Phe Glu Lys Thr Gly Asn Ser Leu Asp Ile
             195                 200                 205

Asp Phe Asn Ser Val His Ser Gly Glu Lys Gln Ile Gln Ile Val Asn
210                 215                 220

Phe Lys Gln Ile Tyr Tyr Thr Val Ser Val Asp Ala Val Lys Asn Pro
225                 230                 235                 240

Gly Asp Val Phe Gln Asp Thr Val Thr Val Glu Asp Leu Lys Gln Arg
                245                 250                 255

Gly Ile Ser Ala Glu Arg Pro Leu Val Tyr Ile Ser Ser Val Ala Tyr
                260                 265                 270

Gly Arg Gln Val Tyr Leu Lys Leu Glu Thr Thr Ser Lys Ser Asp Glu
            275                 280                 285

Val Glu Ala Ala Phe Glu Ala Leu Ile Lys Gly Val Lys Val Ala Pro
        290                 295                 300

Gln Thr Glu Trp Lys Gln Ile Leu Asp Asn Thr Glu Val Lys Ala Val
305                 310                 315                 320

Ile Leu Gly Gly Asp Pro Ser Ser Gly Ala Arg Val Val Thr Gly Lys
                325                 330                 335

Val Asp Met Val Glu Asp Leu Ile Gln Glu Gly Ser Arg Phe Thr Ala
                340                 345                 350

Asp His Pro Gly Leu Pro Ile Ser Tyr Thr Thr Ser Phe Leu Arg Asp
            355                 360                 365

Asn Val Val Ala Thr Phe Gln Asn Ser Thr Asp Tyr Val Glu Thr Lys
370                 375                 380

Val Thr Ala Tyr Arg Asn Gly Asp Leu Leu Asp His Ser Gly Ala
385                 390                 395                 400

Tyr Val Ala Gln Tyr Tyr Ile Thr Trp Asp Glu Leu Ser Tyr Asn His
                405                 410                 415

Gln Gly Lys Glu Val Leu Thr Pro Lys Ala Trp Asp Arg Asn Gly Gln
            420                 425                 430

Asp Leu Thr Ala His Phe Thr Thr Ser Ile Pro Leu Lys Gly Asn Val
        435                 440                 445

Arg Asn Leu Ser Val Lys Ile Arg Glu Cys Thr Gly Leu Ala Trp Glu
450                 455                 460

Trp Trp Arg Thr Val Tyr Glu Lys Thr Asp Leu Pro Leu Val Arg Lys
465                 470                 475                 480

Arg Thr Ile Ser Ile Trp Gly Thr Thr Leu Tyr Pro Gln Val Glu Asp
                485                 490                 495

Lys Val Gly Asn Asp Lys Glu Cys Ala Lys Glu Pro Arg Asn Glu Glu
            500                 505                 510

Lys Val Lys Gln Cys Lys
        515

<210> SEQ ID NO 12
<211> LENGTH: 693
<212> TYPE: PRT
<213> ORGANISM: Streptococcus pneumoniae

<400> SEQUENCE: 12

Met Phe Ala Ser Lys Ser Glu Arg Lys Val His Tyr Ser Ile Arg Lys
1               5                   10                  15

Phe Ser Val Gly Val Ala Ser Val Val Val Ala Ser Leu Val Met Gly
                20                  25                  30

Ser Val Val His Ala Thr Glu Asn Glu Gly Ala Thr Gln Val Pro Thr
            35                  40                  45

```
Ser Ser Asn Arg Ala Asn Glu Ser Gln Ala Glu Gln Gly Glu Gln Pro
    50                  55                  60

Lys Lys Leu Asp Ser Glu Arg Asp Lys Ala Arg Lys Glu Val Glu Glu
65                  70                  75                  80

Tyr Val Lys Lys Ile Val Gly Glu Ser Tyr Ala Lys Ser Thr Lys Lys
                85                  90                  95

Arg His Thr Ile Thr Val Ala Leu Val Asn Glu Leu Asn Asn Ile Lys
            100                 105                 110

Asn Glu Tyr Leu Asn Lys Ile Val Glu Ser Thr Ser Glu Ser Gln Leu
        115                 120                 125

Gln Ile Leu Met Met Glu Ser Arg Ser Lys Val Asp Glu Ala Val Ser
130                 135                 140

Lys Phe Glu Lys Asp Ser Ser Ser Ser Ser Ser Asp Ser Ser Thr
145                 150                 155                 160

Lys Pro Glu Ala Ser Asp Thr Ala Lys Pro Asn Lys Pro Thr Glu Pro
                165                 170                 175

Gly Glu Lys Val Ala Glu Ala Lys Lys Val Glu Ala Glu Lys
            180                 185                 190

Lys Ala Lys Asp Gln Lys Glu Glu Asp Arg Arg Asn Tyr Pro Thr Ile
        195                 200                 205

Thr Tyr Lys Thr Leu Glu Leu Glu Ile Ala Glu Ser Asp Val Glu Val
210                 215                 220

Lys Lys Ala Glu Leu Glu Leu Val Lys Val Lys Ala Asn Glu Pro Arg
225                 230                 235                 240

Asp Glu Gln Lys Ile Lys Gln Ala Glu Ala Val Glu Ser Lys Gln
                245                 250                 255

Ala Glu Ala Thr Arg Leu Lys Lys Ile Lys Thr Asp Arg Glu Glu Ala
            260                 265                 270

Glu Glu Glu Ala Lys Arg Arg Ala Asp Ala Lys Glu Gln Gly Lys Pro
        275                 280                 285

Lys Gly Arg Ala Lys Arg Gly Val Pro Gly Glu Leu Ala Thr Pro Asp
290                 295                 300

Lys Lys Glu Asn Asp Ala Lys Ser Ser Asp Ser Ser Val Gly Glu Glu
305                 310                 315                 320

Thr Leu Pro Ser Pro Ser Leu Lys Pro Glu Lys Lys Val Ala Glu Ala
                325                 330                 335

Glu Lys Lys Val Glu Glu Ala Lys Lys Lys Ala Glu Asp Gln Lys Glu
            340                 345                 350

Glu Asp Arg Arg Asn Tyr Pro Thr Asn Thr Tyr Lys Thr Leu Glu Leu
        355                 360                 365

Glu Ile Ala Glu Ser Asp Val Glu Val Lys Lys Ala Glu Leu Glu Leu
370                 375                 380

Val Lys Glu Glu Ala Lys Glu Pro Arg Asn Glu Glu Lys Val Lys Gln
385                 390                 395                 400

Ala Lys Ala Glu Val Glu Ser Lys Lys Ala Glu Ala Thr Arg Leu Glu
                405                 410                 415

Lys Ile Lys Thr Asp Arg Lys Lys Ala Glu Glu Glu Ala Lys Arg Lys
            420                 425                 430

Ala Ala Glu Glu Asp Lys Val Lys Glu Lys Pro Ala Glu Gln Pro Gln
        435                 440                 445

Pro Ala Pro Ala Pro Lys Ala Glu Lys Pro Ala Pro Ala Pro Lys Pro
450                 455                 460
```

```
Glu Asn Pro Ala Glu Gln Pro Lys Ala Glu Lys Pro Ala Asp Gln Gln
465                 470                 475                 480

Ala Glu Glu Asp Tyr Ala Arg Arg Ser Glu Glu Tyr Asn Arg Leu
                485                 490                 495

Thr Gln Gln Gln Pro Pro Lys Thr Glu Lys Pro Ala Gln Pro Ser Thr
            500                 505                 510

Pro Lys Thr Gly Trp Lys Gln Glu Asn Gly Met Trp Tyr Phe Tyr Asn
            515                 520                 525

Thr Asp Gly Ser Met Ala Thr Gly Trp Leu Gln Asn Gly Ser Trp
530                 535                 540

Tyr Tyr Leu Asn Ser Asn Gly Ala Met Ala Thr Gly Trp Leu Gln Asn
545                 550                 555                 560

Asn Gly Ser Trp Tyr Tyr Leu Asn Ala Asn Gly Ser Met Ala Thr Gly
                565                 570                 575

Trp Leu Gln Asn Asn Gly Ser Trp Tyr Tyr Leu Asn Ala Asn Gly Ser
                580                 585                 590

Met Ala Thr Gly Trp Leu Gln Tyr Asn Gly Ser Trp Tyr Tyr Leu Asn
                595                 600                 605

Ala Asn Gly Ser Met Ala Thr Gly Trp Leu Gln Tyr Asn Gly Ser Trp
610                 615                 620

Tyr Tyr Leu Asn Ala Asn Gly Asp Met Ala Thr Gly Trp Val Lys Asp
625                 630                 635                 640

Gly Asp Thr Trp Tyr Tyr Leu Glu Ala Ser Gly Ala Met Lys Ala Ser
                645                 650                 655

Gln Trp Phe Lys Val Ser Asp Lys Trp Tyr Tyr Val Asn Gly Ser Gly
                660                 665                 670

Ala Leu Ala Val Asn Thr Thr Val Asp Gly Tyr Gly Val Asn Ala Asn
                675                 680                 685

Gly Glu Trp Val Asn
690

<210> SEQ ID NO 13
<211> LENGTH: 472
<212> TYPE: PRT
<213> ORGANISM: Streptococcus pneumoniae

<400> SEQUENCE: 13

Glu Asn Glu Gly Ala Thr Gln Val Pro Thr Ser Ser Asn Arg Ala Asn
1               5                   10                  15

Glu Ser Gln Ala Glu Gln Gly Glu Gln Pro Lys Lys Leu Asp Ser Glu
                20                  25                  30

Arg Asp Lys Ala Arg Lys Glu Val Glu Glu Tyr Val Lys Lys Ile Val
            35                  40                  45

Gly Glu Ser Tyr Ala Lys Ser Thr Lys Lys Arg His Thr Ile Thr Val
50                  55                  60

Ala Leu Val Asn Glu Leu Asn Asn Ile Lys Asn Glu Tyr Leu Asn Lys
65                  70                  75                  80

Ile Val Glu Ser Thr Ser Glu Ser Gln Leu Gln Ile Leu Met Met Glu
                85                  90                  95

Ser Arg Ser Lys Val Asp Glu Ala Val Ser Lys Phe Glu Lys Asp Ser
            100                 105                 110

Ser Ser Ser Ser Ser Ser Asp Ser Ser Thr Lys Pro Glu Ala Ser Asp
        115                 120                 125

Thr Ala Lys Pro Asn Lys Pro Thr Glu Pro Gly Glu Lys Val Ala Glu
130                 135                 140
```

Ala Lys Lys Lys Val Glu Ala Glu Lys Ala Lys Asp Gln Lys
145                 150                 155                 160

Glu Glu Asp Arg Arg Asn Tyr Pro Thr Ile Thr Tyr Lys Thr Leu Glu
            165                 170                 175

Leu Glu Ile Ala Glu Ser Asp Val Glu Val Lys Lys Ala Glu Leu Glu
            180                 185                 190

Leu Val Lys Val Lys Ala Asn Glu Pro Arg Asp Glu Gln Lys Ile Lys
        195                 200                 205

Gln Ala Glu Ala Glu Val Glu Ser Lys Gln Ala Glu Ala Thr Arg Leu
210                 215                 220

Lys Lys Ile Lys Thr Asp Arg Glu Glu Ala Glu Glu Ala Lys Arg
225                 230                 235                 240

Arg Ala Asp Ala Lys Glu Gln Gly Lys Pro Lys Gly Arg Ala Lys Arg
                245                 250                 255

Gly Val Pro Gly Glu Leu Ala Thr Pro Asp Lys Lys Glu Asn Asp Ala
                260                 265                 270

Lys Ser Ser Asp Ser Ser Val Gly Glu Glu Thr Leu Pro Ser Pro Ser
        275                 280                 285

Leu Lys Pro Glu Lys Val Ala Glu Ala Glu Lys Lys Val Glu Glu
290                 295                 300

Ala Lys Lys Lys Ala Glu Asp Gln Lys Glu Glu Asp Arg Arg Asn Tyr
305                 310                 315                 320

Pro Thr Asn Thr Tyr Lys Thr Leu Glu Leu Glu Ile Ala Glu Ser Asp
                325                 330                 335

Val Glu Val Lys Lys Ala Glu Leu Glu Leu Val Lys Glu Glu Ala Lys
                340                 345                 350

Glu Pro Arg Asn Glu Glu Lys Val Lys Gln Ala Lys Ala Glu Val Glu
                355                 360                 365

Ser Lys Lys Ala Glu Ala Thr Arg Leu Glu Lys Ile Lys Thr Asp Arg
        370                 375                 380

Lys Lys Ala Glu Glu Ala Lys Arg Lys Ala Ala Glu Glu Asp Lys
385                 390                 395                 400

Val Lys Glu Lys Pro Ala Glu Gln Pro Gln Pro Ala Pro Ala Pro Lys
                405                 410                 415

Ala Glu Lys Pro Ala Pro Ala Pro Lys Pro Glu Asn Pro Ala Glu Gln
                420                 425                 430

Pro Lys Ala Glu Lys Pro Ala Asp Gln Gln Ala Glu Glu Asp Tyr Ala
        435                 440                 445

Arg Arg Ser Glu Glu Glu Tyr Asn Arg Leu Thr Gln Gln Pro Pro
450                 455                 460

Lys Thr Glu Lys Pro Ala Gln Pro
465                 470

<210> SEQ ID NO 14
<211> LENGTH: 115
<212> TYPE: PRT
<213> ORGANISM: Streptococcus pneumoniae

<400> SEQUENCE: 14

Pro Glu Lys Lys Val Ala Glu Ala Glu Lys Lys Val Glu Glu Ala Lys
1               5                   10                  15

Lys Lys Ala Glu Asp Gln Lys Glu Glu Asp Arg Arg Asn Tyr Pro Thr
                20                  25                  30

Asn Thr Tyr Lys Thr Leu Glu Leu Glu Ile Ala Glu Ser Asp Val Glu

```
                35                  40                  45
Val Lys Lys Ala Glu Leu Glu Leu Val Lys Glu Ala Lys Glu Pro
 50                  55                  60

Arg Asn Glu Glu Lys Val Lys Gln Ala Lys Ala Glu Val Glu Ser Lys
 65                  70                  75                  80

Lys Ala Glu Ala Thr Arg Leu Glu Lys Ile Lys Thr Asp Arg Lys Lys
                 85                  90                  95

Ala Glu Glu Glu Ala Lys Arg Lys Ala Ala Glu Glu Asp Lys Val Lys
                100                 105                 110

Glu Lys Pro
        115

<210> SEQ ID NO 15
<211> LENGTH: 13
<212> TYPE: PRT
<213> ORGANISM: Artificial Sequence
<220> FEATURE:
<223> OTHER INFORMATION: T cell epitope

<400> SEQUENCE: 15

Gln Tyr Ile Lys Ala Asn Ser Lys Phe Ile Gly Ile Thr
 1               5                  10

<210> SEQ ID NO 16
<211> LENGTH: 15
<212> TYPE: PRT
<213> ORGANISM: Artificial Sequence
<220> FEATURE:
<223> OTHER INFORMATION: T cell epitope

<400> SEQUENCE: 16

Pro Val Val Glu Val Asn Gly Val Thr Ile Gln Val Gly Ser Arg
 1               5                  10                  15

<210> SEQ ID NO 17
<211> LENGTH: 471
<212> TYPE: PRT
<213> ORGANISM: Artificial Sequence
<220> FEATURE:
<223> OTHER INFORMATION: PdB pneumolysin mutant

<400> SEQUENCE: 17

Met Ala Asn Lys Ala Val Asn Asp Phe Ile Leu Ala Met Asn Tyr Asp
 1               5                  10                  15

Lys Lys Lys Leu Leu Thr His Gln Gly Glu Ser Ile Glu Asn Arg Phe
                20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
         50                  55                  60

Thr Asn Asp Ser Arg Leu Tyr Pro Gly Ala Leu Leu Val Val Asp Glu
 65                  70                  75                  80

Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
        130                 135                 140
```

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
            165                 170                 175

Asp Ile Asp Phe Asn Ser Val His Ser Gly Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Phe Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
450                 455                 460

Glu Asp Lys Val Glu Asn Asp
465                 470

<210> SEQ ID NO 18
<211> LENGTH: 529
<212> TYPE: PRT
<213> ORGANISM: Artificial Sequence
<220> FEATURE:
<223> OTHER INFORMATION: PdB-2TCE-linear NEEK fusion protein

<400> SEQUENCE: 18

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
                35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
                115                 120                 125

Asp Leu Leu Ala Lys Trp His Gln Asp Tyr Gly Gln Val Asn Asn Val
                130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
                195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
                260                 265                 270

Ala Pro Gln Thr Glu Trp Lys Gln Ile Leu Asp Asn Thr Glu Val Lys
                275                 280                 285

Ala Val Ile Leu Gly Gly Asp Pro Ser Ser Gly Ala Arg Val Val Thr
                290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
                355                 360                 365

Gly Ala Tyr Val Ala Gln Tyr Tyr Ile Thr Trp Asp Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
                420                 425                 430

Phe Glu Trp Trp Arg Thr Val Tyr Glu Lys Thr Asp Leu Pro Leu Val
                435                 440                 445

```
Arg Lys Arg Thr Ile Ser Ile Trp Gly Thr Thr Leu Tyr Pro Gln Val
    450                 455                 460

Glu Asp Lys Val Glu Asn Asp Gln Tyr Ile Lys Ala Asn Ser Lys Phe
465                 470                 475                 480

Ile Gly Ile Thr Gln Tyr Ile Lys Ala Asn Ser Lys Phe Ile Gly Ile
            485                 490                 495

Thr Gly Gly Lys Ala Glu Leu Glu Leu Val Lys Glu Glu Ala Lys Glu
            500                 505                 510

Pro Arg Asn Glu Glu Lys Val Lys Gln Ala Lys Ala Glu Val Glu Ser
            515                 520                 525

Lys

<210> SEQ ID NO 19
<211> LENGTH: 559
<212> TYPE: PRT
<213> ORGANISM: Artificial Sequence
<220> FEATURE:
<223> OTHER INFORMATION: Looped YPT-PdB-2TCE-linear NEEK fusion
      protein

<400> SEQUENCE: 19

Met Ala Cys Lys Lys Ala Glu Asp Gln Lys Glu Glu Asp Arg Arg Asn
 1               5                  10                  15

Tyr Pro Thr Asn Thr Tyr Lys Thr Leu Glu Leu Glu Cys Ala Glu Ala
            20                  25                  30

Asn Lys Ala Val Asn Asp Phe Ile Leu Ala Met Asn Tyr Asp Lys Lys
        35                  40                  45

Lys Leu Leu Thr His Gln Gly Glu Ser Ile Glu Asn Arg Phe Ile Lys
50                  55                  60

Glu Gly Asn Gln Leu Pro Asp Glu Phe Val Val Ile Glu Arg Lys Lys
65                  70                  75                  80

Arg Ser Leu Ser Thr Asn Thr Ser Asp Ile Ser Val Thr Ala Thr Asn
                85                  90                  95

Asp Ser Arg Leu Tyr Pro Gly Ala Leu Leu Val Val Asp Glu Thr Leu
            100                 105                 110

Leu Glu Asn Asn Pro Thr Leu Leu Ala Val Asp Arg Ala Pro Met Thr
        115                 120                 125

Tyr Ser Ile Asp Leu Pro Gly Leu Ala Ser Ser Asp Ser Phe Leu Gln
130                 135                 140

Val Glu Asp Pro Ser Asn Ser Ser Val Arg Gly Ala Val Asn Asp Leu
145                 150                 155                 160

Leu Ala Lys Trp His Gln Asp Tyr Gly Gln Val Asn Asn Val Pro Ala
                165                 170                 175

Arg Met Gln Tyr Glu Lys Ile Thr Ala His Ser Met Glu Gln Leu Lys
            180                 185                 190

Val Lys Phe Gly Ser Asp Phe Glu Lys Thr Gly Asn Ser Leu Asp Ile
        195                 200                 205

Asp Phe Asn Ser Val His Ser Gly Glu Lys Gln Ile Gln Ile Val Asn
210                 215                 220

Phe Lys Gln Ile Tyr Tyr Thr Val Ser Val Asp Ala Val Lys Asn Pro
225                 230                 235                 240

Gly Asp Val Phe Gln Asp Thr Val Thr Val Glu Asp Leu Lys Gln Arg
                245                 250                 255

Gly Ile Ser Ala Glu Arg Pro Leu Val Tyr Ile Ser Ser Val Ala Tyr
            260                 265                 270
```

-continued

```
Gly Arg Gln Val Tyr Leu Lys Leu Glu Thr Thr Ser Lys Ser Asp Glu
            275                 280                 285

Val Glu Ala Ala Phe Glu Ala Leu Ile Lys Gly Val Lys Val Ala Pro
290                 295                 300

Gln Thr Glu Trp Lys Gln Ile Leu Asp Asn Thr Glu Val Lys Ala Val
305                 310                 315                 320

Ile Leu Gly Gly Asp Pro Ser Ser Gly Ala Arg Val Val Thr Gly Lys
                325                 330                 335

Val Asp Met Val Glu Asp Leu Ile Gln Glu Gly Ser Arg Phe Thr Ala
            340                 345                 350

Asp His Pro Gly Leu Pro Ile Ser Tyr Thr Thr Ser Phe Leu Arg Asp
            355                 360                 365

Asn Val Val Ala Thr Phe Gln Asn Ser Thr Asp Tyr Val Glu Thr Lys
        370                 375                 380

Val Thr Ala Tyr Arg Asn Gly Asp Leu Leu Leu Asp His Ser Gly Ala
385                 390                 395                 400

Tyr Val Ala Gln Tyr Tyr Ile Thr Trp Asp Glu Leu Ser Tyr Asp His
                405                 410                 415

Gln Gly Lys Glu Val Leu Thr Pro Lys Ala Trp Asp Arg Asn Gly Gln
            420                 425                 430

Asp Leu Thr Ala His Phe Thr Thr Ser Ile Pro Leu Lys Gly Asn Val
        435                 440                 445

Arg Asn Leu Ser Val Lys Ile Arg Glu Cys Thr Gly Leu Ala Phe Glu
    450                 455                 460

Trp Trp Arg Thr Val Tyr Glu Lys Thr Asp Leu Pro Leu Val Arg Lys
465                 470                 475                 480

Arg Thr Ile Ser Ile Trp Gly Thr Thr Leu Tyr Pro Gln Val Glu Asp
                485                 490                 495

Lys Val Glu Asn Asp Gln Tyr Ile Lys Ala Asn Ser Lys Phe Ile Gly
            500                 505                 510

Ile Thr Gln Tyr Ile Lys Ala Asn Ser Lys Phe Ile Gly Ile Thr Gly
        515                 520                 525

Gly Lys Cys Glu Leu Glu Leu Val Lys Glu Glu Ala Lys Glu Pro Arg
    530                 535                 540

Asn Glu Glu Lys Val Lys Gln Ala Lys Ala Glu Cys Glu Ser Lys
545                 550                 555
```

<210> SEQ ID NO 20
<211> LENGTH: 486
<212> TYPE: PRT
<213> ORGANISM: Artificial Sequence
<220> FEATURE:
<223> OTHER INFORMATION: Delta6N385-NEEK fusion protein

<400> SEQUENCE: 20

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80
```

```
Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Met Gln Tyr Glu Lys Ile Thr Ala His Ser Met Glu Gln Leu Lys
145                 150                 155                 160

Val Lys Phe Gly Ser Asp Phe Glu Lys Thr Gly Asn Ser Leu Asp Ile
                165                 170                 175

Asp Phe Asn Ser Val His Ser Gly Glu Lys Gln Ile Gln Ile Val Asn
            180                 185                 190

Phe Lys Gln Ile Tyr Tyr Thr Val Ser Val Asp Ala Val Lys Asn Pro
        195                 200                 205

Gly Asp Val Phe Gln Asp Thr Val Thr Val Glu Asp Leu Lys Gln Arg
    210                 215                 220

Gly Ile Ser Ala Glu Arg Pro Leu Val Tyr Ile Ser Ser Val Ala Tyr
225                 230                 235                 240

Gly Arg Gln Val Tyr Leu Lys Leu Glu Thr Thr Ser Lys Ser Asp Glu
                245                 250                 255

Val Glu Ala Ala Phe Glu Ala Leu Ile Lys Gly Val Lys Val Ala Pro
            260                 265                 270

Gln Thr Glu Trp Lys Gln Ile Leu Asp Asn Thr Glu Val Lys Ala Val
        275                 280                 285

Ile Leu Gly Gly Asp Pro Ser Ser Gly Ala Arg Val Val Thr Gly Lys
    290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
            340                 345                 350

Val Thr Ala Tyr Arg Asn Gly Asp Leu Leu Asp His Ser Gly Ala
        355                 360                 365

Tyr Val Ala Gln Tyr Tyr Ile Thr Trp Asp Glu Leu Ser Tyr Asn His
    370                 375                 380

Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
                405                 410                 415

Arg Asn Leu Ser Val Lys Ile Arg Glu Cys Thr Gly Leu Ala Trp Glu
            420                 425                 430

Trp Trp Arg Thr Val Tyr Glu Lys Thr Asp Leu Pro Leu Val Arg Lys
        435                 440                 445

Arg Thr Ile Ser Ile Trp Gly Thr Thr Leu Tyr Pro Gln Val Glu Asp
    450                 455                 460

Lys Val Glu Asn Asp Lys Glu Cys Ala Lys Glu Pro Arg Asn Glu Glu
465                 470                 475                 480

Lys Val Lys Gln Cys Lys
                485
```

```
<210> SEQ ID NO 21
<211> LENGTH: 516
<212> TYPE: PRT
<213> ORGANISM: Artificial Sequence
<220> FEATURE:
<223> OTHER INFORMATION: Delta6N385-TCE-NEEK fusion protein

<400> SEQUENCE: 21

Met Ala Asn Lys Ala Val Asn Asp Phe Ile Leu Ala Met Asn Tyr Asp
 1               5                  10                  15

Lys Lys Lys Leu Leu Thr His Gln Gly Glu Ser Ile Glu Asn Arg Phe
                20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
        50                  55                  60

Thr Asn Asp Ser Arg Leu Tyr Pro Gly Ala Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Met Gln Tyr Glu Lys Ile Thr Ala His Ser Met Glu Gln Leu Lys
145                 150                 155                 160

Val Lys Phe Gly Ser Asp Phe Glu Lys Thr Gly Asn Ser Leu Asp Ile
                165                 170                 175

Asp Phe Asn Ser Val His Ser Gly Glu Lys Gln Ile Gln Ile Val Asn
            180                 185                 190

Phe Lys Gln Ile Tyr Tyr Thr Val Ser Val Asp Ala Val Lys Asn Pro
        195                 200                 205

Gly Asp Val Phe Gln Asp Thr Val Thr Val Glu Asp Leu Lys Gln Arg
    210                 215                 220

Gly Ile Ser Ala Glu Arg Pro Leu Val Tyr Ile Ser Ser Val Ala Tyr
225                 230                 235                 240

Gly Arg Gln Val Tyr Leu Lys Leu Glu Thr Thr Ser Lys Ser Asp Glu
                245                 250                 255

Val Glu Ala Ala Phe Glu Ala Leu Ile Lys Gly Val Lys Val Ala Pro
            260                 265                 270

Gln Thr Glu Trp Lys Gln Ile Leu Asp Asn Thr Glu Val Lys Ala Val
        275                 280                 285

Ile Leu Gly Gly Asp Pro Ser Ser Gly Ala Arg Val Val Thr Gly Lys
    290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
            340                 345                 350

Val Thr Ala Tyr Arg Asn Gly Asp Leu Leu Leu Asp His Ser Gly Ala
        355                 360                 365

Tyr Val Ala Gln Tyr Tyr Ile Thr Trp Asp Glu Leu Ser Tyr Asn His
```

```
            370                 375                 380
Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
                405                 410                 415

Arg Asn Leu Ser Val Lys Ile Arg Glu Cys Thr Gly Leu Ala Trp Glu
            420                 425                 430

Trp Trp Arg Thr Val Tyr Glu Lys Thr Asp Leu Pro Leu Val Arg Lys
        435                 440                 445

Arg Thr Ile Ser Ile Trp Gly Thr Thr Leu Tyr Pro Gln Val Glu Asp
    450                 455                 460

Lys Val Glu Asn Asp Gly Gly Gln Tyr Ile Lys Ala Asn Ser Lys Phe
465                 470                 475                 480

Ile Gly Ile Thr Gln Tyr Ile Lys Ala Asn Ser Lys Phe Ile Gly Ile
                485                 490                 495

Thr Gly Gly Lys Glu Cys Ala Lys Glu Pro Arg Asn Glu Glu Lys Val
            500                 505                 510

Lys Gln Cys Lys
        515

<210> SEQ ID NO 22
<211> LENGTH: 500
<212> TYPE: PRT
<213> ORGANISM: Artificial Sequence
<220> FEATURE:
<223> OTHER INFORMATION: YPT-Delta6N385 fusion protein

<400> SEQUENCE: 22

Met Ala Cys Lys Lys Ala Glu Asp Gln Lys Glu Glu Asp Arg Arg Asn
1               5                   10                  15

Tyr Pro Thr Asn Thr Tyr Lys Thr Leu Glu Leu Glu Cys Ala Glu Met
            20                  25                  30

Ala Asn Lys Ala Val Asn Asp Phe Ile Leu Ala Met Asn Tyr Asp Lys
        35                  40                  45

Lys Lys Leu Leu Thr His Gln Gly Glu Ser Ile Glu Asn Arg Phe Ile
50                  55                  60

Lys Glu Gly Asn Gln Leu Pro Asp Glu Phe Val Val Ile Glu Arg Lys
65                  70                  75                  80

Lys Arg Ser Leu Ser Thr Asn Thr Ser Asp Ile Ser Val Thr Ala Thr
                85                  90                  95

Asn Asp Ser Arg Leu Tyr Pro Gly Ala Leu Leu Val Val Asp Glu Thr
            100                 105                 110

Leu Leu Glu Asn Asn Pro Thr Leu Leu Ala Val Asp Arg Ala Pro Met
        115                 120                 125

Thr Tyr Ser Ile Asp Leu Pro Gly Leu Ala Ser Ser Asp Ser Phe Leu
    130                 135                 140

Gln Val Glu Asp Pro Ser Asn Ser Ser Val Arg Gly Ala Val Asn Asp
145                 150                 155                 160

Leu Leu Ala Lys Trp His Gln Asp Tyr Gly Gln Val Asn Asn Val Pro
                165                 170                 175

Met Gln Tyr Glu Lys Ile Thr Ala His Ser Met Glu Gln Leu Lys Val
            180                 185                 190

Lys Phe Gly Ser Asp Phe Glu Lys Thr Gly Asn Ser Leu Asp Ile Asp
        195                 200                 205

Phe Asn Ser Val His Ser Gly Glu Lys Gln Ile Gln Ile Val Asn Phe
```

```
                   210                 215                 220
Lys Gln Ile Tyr Tyr Thr Val Ser Val Asp Ala Val Lys Asn Pro Gly
225                 230                 235                 240

Asp Val Phe Gln Asp Thr Val Thr Val Glu Asp Leu Lys Gln Arg Gly
                245                 250                 255

Ile Ser Ala Glu Arg Pro Leu Val Tyr Ile Ser Ser Val Ala Tyr Gly
                260                 265                 270

Arg Gln Val Tyr Leu Lys Leu Glu Thr Thr Ser Lys Ser Asp Glu Val
            275                 280                 285

Glu Ala Ala Phe Glu Ala Leu Ile Lys Gly Val Lys Val Ala Pro Gln
        290                 295                 300

Thr Glu Trp Lys Gln Ile Leu Asp Asn Thr Glu Val Lys Ala Val Ile
305                 310                 315                 320

Leu Gly Gly Asp Pro Ser Ser Gly Ala Arg Val Val Thr Gly Lys Val
                325                 330                 335

Asp Met Val Glu Asp Leu Ile Gln Glu Gly Ser Arg Phe Thr Ala Asp
                340                 345                 350

His Pro Gly Leu Pro Ile Ser Tyr Thr Thr Ser Phe Leu Arg Asp Asn
            355                 360                 365

Val Val Ala Thr Phe Gln Asn Ser Thr Asp Tyr Val Glu Thr Lys Val
        370                 375                 380

Thr Ala Tyr Arg Asn Gly Asp Leu Leu Leu Asp His Ser Gly Ala Tyr
385                 390                 395                 400

Val Ala Gln Tyr Tyr Ile Thr Trp Asp Glu Leu Ser Tyr Asn His Gln
                405                 410                 415

Gly Lys Glu Val Leu Thr Pro Lys Ala Trp Asp Arg Asn Gly Gln Asp
            420                 425                 430

Leu Thr Ala His Phe Thr Thr Ser Ile Pro Leu Lys Gly Asn Val Arg
        435                 440                 445

Asn Leu Ser Val Lys Ile Arg Glu Cys Thr Gly Leu Ala Trp Glu Trp
450                 455                 460

Trp Arg Thr Val Tyr Glu Lys Thr Asp Leu Pro Leu Val Arg Lys Arg
465                 470                 475                 480

Thr Ile Ser Ile Trp Gly Thr Thr Leu Tyr Pro Gln Val Glu Asp Lys
                485                 490                 495

Val Glu Asn Asp
            500

<210> SEQ ID NO 23
<211> LENGTH: 547
<212> TYPE: PRT
<213> ORGANISM: Artificial Sequence
<220> FEATURE:
<223> OTHER INFORMATION: YPT-Delta6N385-TCE-NEEK fusion protein

<400> SEQUENCE: 23

Met Ala Cys Lys Lys Ala Glu Asp Gln Lys Glu Glu Asp Arg Arg Asn
  1               5                  10                  15

Tyr Pro Thr Asn Thr Tyr Lys Thr Leu Glu Leu Glu Cys Ala Glu Met
                 20                  25                  30

Ala Asn Lys Ala Val Asn Asp Phe Ile Leu Ala Met Asn Tyr Asp Lys
             35                  40                  45

Lys Lys Leu Leu Thr His Gln Gly Glu Ser Ile Glu Asn Arg Phe Ile
         50                  55                  60

Lys Glu Gly Asn Gln Leu Pro Asp Glu Phe Val Val Ile Glu Arg Lys
```

```
            65                  70                  75                  80
Lys Arg Ser Leu Ser Thr Asn Thr Ser Asp Ile Ser Val Thr Ala Thr
                    85                  90                  95

Asn Asp Ser Arg Leu Tyr Pro Gly Ala Leu Leu Val Val Asp Glu Thr
                100                 105                 110

Leu Leu Glu Asn Asn Pro Thr Leu Leu Ala Val Asp Arg Ala Pro Met
                115                 120                 125

Thr Tyr Ser Ile Asp Leu Pro Gly Leu Ala Ser Ser Asp Ser Phe Leu
            130                 135                 140

Gln Val Glu Asp Pro Ser Asn Ser Ser Val Arg Gly Ala Val Asn Asp
145                 150                 155                 160

Leu Leu Ala Lys Trp His Gln Asp Tyr Gly Gln Val Asn Asn Val Pro
                    165                 170                 175

Met Gln Tyr Glu Lys Ile Thr Ala His Ser Met Glu Gln Leu Lys Val
                180                 185                 190

Lys Phe Gly Ser Asp Phe Glu Lys Thr Gly Asn Ser Leu Asp Ile Asp
                195                 200                 205

Phe Asn Ser Val His Ser Gly Glu Lys Gln Ile Gln Ile Val Asn Phe
            210                 215                 220

Lys Gln Ile Tyr Tyr Thr Val Ser Val Asp Ala Val Lys Asn Pro Gly
225                 230                 235                 240

Asp Val Phe Gln Asp Thr Val Thr Val Glu Asp Leu Lys Gln Arg Gly
                245                 250                 255

Ile Ser Ala Glu Arg Pro Leu Val Tyr Ile Ser Ser Val Ala Tyr Gly
                260                 265                 270

Arg Gln Val Tyr Leu Lys Leu Glu Thr Thr Ser Lys Ser Asp Glu Val
            275                 280                 285

Glu Ala Ala Phe Glu Ala Leu Ile Lys Gly Val Lys Val Ala Pro Gln
                290                 295                 300

Thr Glu Trp Lys Gln Ile Leu Asp Asn Thr Glu Val Lys Ala Val Ile
305                 310                 315                 320

Leu Gly Gly Asp Pro Ser Ser Gly Ala Arg Val Val Thr Gly Lys Val
                325                 330                 335

Asp Met Val Glu Asp Leu Ile Gln Glu Gly Ser Arg Phe Thr Ala Asp
                340                 345                 350

His Pro Gly Leu Pro Ile Ser Tyr Thr Thr Ser Phe Leu Arg Asp Asn
            355                 360                 365

Val Val Ala Thr Phe Gln Asn Ser Thr Asp Tyr Val Glu Thr Lys Val
            370                 375                 380

Thr Ala Tyr Arg Asn Gly Asp Leu Leu Leu Asp His Ser Gly Ala Tyr
385                 390                 395                 400

Val Ala Gln Tyr Tyr Ile Thr Trp Asp Glu Leu Ser Tyr Asn His Gln
                405                 410                 415

Gly Lys Glu Val Leu Thr Pro Lys Ala Trp Asp Arg Asn Gly Gln Asp
                420                 425                 430

Leu Thr Ala His Phe Thr Thr Ser Ile Pro Leu Lys Gly Asn Val Arg
            435                 440                 445

Asn Leu Ser Val Lys Ile Arg Glu Cys Thr Gly Leu Ala Trp Glu Trp
            450                 455                 460

Trp Arg Thr Val Tyr Glu Lys Thr Asp Leu Pro Leu Val Arg Lys Arg
465                 470                 475                 480

Thr Ile Ser Ile Trp Gly Thr Thr Leu Tyr Pro Gln Val Glu Asp Lys
                485                 490                 495
```

```
Val Glu Asn Asp Gly Gly Gln Tyr Ile Lys Ala Asn Ser Lys Phe Ile
            500                 505                 510

Gly Ile Thr Gln Tyr Ile Lys Ala Asn Ser Lys Phe Ile Gly Ile Thr
            515                 520                 525

Gly Gly Lys Glu Cys Ala Lys Glu Pro Arg Asn Glu Glu Lys Val Lys
            530                 535                 540

Gln Cys Lys
545

<210> SEQ ID NO 24
<211> LENGTH: 548
<212> TYPE: PRT
<213> ORGANISM: Artificial Sequence
<220> FEATURE:
<223> OTHER INFORMATION: YPT-L460D-TCE-NEEK fusion protein

<400> SEQUENCE: 24

Met Ala Cys Lys Lys Ala Glu Asp Gln Lys Glu Glu Asp Arg Arg Asn
  1               5                  10                  15

Tyr Pro Thr Asn Thr Tyr Lys Thr Leu Glu Leu Glu Cys Ala Glu Gly
             20                  25                  30

Gly Ala Asn Lys Ala Val Asn Asp Phe Ile Leu Ala Met Asn Tyr Asp
         35                  40                  45

Lys Lys Lys Leu Leu Thr His Gln Gly Glu Ser Ile Glu Asn Arg Phe
 50                  55                  60

Ile Lys Glu Gly Asn Gln Leu Pro Asp Glu Phe Val Val Ile Glu Arg
 65                  70                  75                  80

Lys Lys Arg Ser Leu Ser Thr Asn Thr Ser Asp Ile Ser Val Thr Ala
                 85                  90                  95

Thr Asn Asp Ser Arg Leu Tyr Pro Gly Ala Leu Leu Val Val Asp Glu
            100                 105                 110

Thr Leu Leu Glu Asn Asn Pro Thr Leu Leu Ala Val Asp Arg Ala Pro
        115                 120                 125

Met Thr Tyr Ser Ile Asp Leu Pro Gly Leu Ala Ser Ser Asp Ser Phe
130                 135                 140

Leu Gln Val Glu Asp Pro Ser Asn Ser Ser Val Arg Gly Ala Val Asn
145                 150                 155                 160

Asp Leu Leu Ala Lys Trp His Gln Asp Tyr Gly Gln Val Asn Asn Val
                165                 170                 175

Pro Ala Arg Met Gln Tyr Glu Lys Ile Thr Ala His Ser Met Glu Gln
            180                 185                 190

Leu Lys Val Lys Phe Gly Ser Asp Phe Glu Lys Thr Gly Asn Ser Leu
        195                 200                 205

Asp Ile Asp Phe Asn Ser Val His Ser Gly Glu Lys Gln Ile Gln Ile
210                 215                 220

Val Asn Phe Lys Gln Ile Tyr Tyr Thr Val Ser Val Asp Ala Val Lys
225                 230                 235                 240

Asn Pro Gly Asp Val Phe Gln Asp Thr Val Thr Val Glu Asp Leu Lys
                245                 250                 255

Gln Arg Gly Ile Ser Ala Glu Arg Pro Leu Val Tyr Ile Ser Ser Val
            260                 265                 270

Ala Tyr Gly Arg Gln Val Tyr Leu Lys Leu Glu Thr Thr Ser Lys Ser
        275                 280                 285

Asp Glu Val Glu Ala Ala Phe Glu Ala Leu Ile Lys Gly Val Lys Val
290                 295                 300
```

Ala Pro Gln Thr Glu Trp Lys Gln Ile Leu Asp Asn Thr Glu Val Lys
305                 310                 315                 320

Ala Val Ile Leu Gly Gly Asp Pro Ser Ser Gly Ala Arg Val Val Thr
            325                 330                 335

Gly Lys Val Asp Met Val Glu Asp Leu Ile Gln Glu Gly Ser Arg Phe
            340                 345                 350

Thr Ala Asp His Pro Gly Leu Pro Ile Ser Tyr Thr Thr Ser Phe Leu
            355                 360                 365

Arg Asp Asn Val Val Ala Thr Phe Gln Asn Ser Thr Asp Tyr Val Glu
        370                 375                 380

Thr Lys Val Thr Ala Tyr Arg Asn Gly Asp Leu Leu Leu Asp His Ser
385                 390                 395                 400

Gly Ala Tyr Val Ala Gln Tyr Tyr Ile Thr Trp Asp Glu Leu Ser Tyr
                405                 410                 415

Asp His Gln Gly Lys Glu Val Leu Thr Pro Lys Ala Trp Asp Arg Asn
            420                 425                 430

Gly Gln Asp Leu Thr Ala His Phe Thr Thr Ser Ile Pro Leu Lys Gly
            435                 440                 445

Asn Val Arg Asn Leu Ser Val Lys Ile Arg Glu Cys Thr Gly Leu Ala
        450                 455                 460

Trp Glu Trp Trp Arg Thr Val Tyr Glu Lys Thr Asp Leu Pro Leu Val
465                 470                 475                 480

Arg Lys Arg Thr Ile Ser Ile Trp Gly Thr Thr Asp Tyr Pro Gln Val
                485                 490                 495

Glu Asp Lys Val Glu Asn Asp Gln Tyr Ile Lys Ala Asn Ser Lys Phe
            500                 505                 510

Ile Gly Ile Thr Gln Tyr Ile Lys Ala Asn Ser Lys Phe Ile Gly Ile
            515                 520                 525

Thr Gly Gly Lys Glu Cys Ala Lys Glu Pro Arg Asn Glu Glu Lys Val
            530                 535                 540

Lys Gln Cys Lys
545

<210> SEQ ID NO 25
<211> LENGTH: 488
<212> TYPE: PRT
<213> ORGANISM: Artificial Sequence
<220> FEATURE:
<223> OTHER INFORMATION: L460D-NEEK fusion protein

<400> SEQUENCE: 25

Met Ala Asn Lys Ala Val Asn Asp Phe Ile Leu Ala Met Asn Tyr Asp
  1               5                  10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

```
Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
                195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
                260                 265                 270

Ala Pro Gln Thr Glu Trp Lys Gln Ile Leu Asp Asn Thr Glu Val Lys
                275                 280                 285

Ala Val Ile Leu Gly Gly Asp Pro Ser Ser Gly Ala Arg Val Val Thr
                290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
                355                 360                 365

Gly Ala Tyr Val Ala Gln Tyr Tyr Ile Thr Trp Asp Glu Leu Ser Tyr
                370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
                420                 425                 430

Trp Glu Trp Trp Arg Thr Val Tyr Glu Lys Thr Asp Leu Pro Leu Val
                435                 440                 445

Arg Lys Arg Thr Ile Ser Ile Trp Gly Thr Thr Asp Tyr Pro Gln Val
                450                 455                 460

Glu Asp Lys Val Glu Asn Asp Lys Glu Cys Ala Lys Glu Pro Arg Asn
465                 470                 475                 480

Glu Glu Lys Val Lys Gln Cys Lys
                485

<210> SEQ ID NO 26
<211> LENGTH: 31
<212> TYPE: DNA
<213> ORGANISM: Artificial Sequence
<220> FEATURE:
```

```
<223> OTHER INFORMATION: JAT201 primer

<400> SEQUENCE: 26
cgcgggatcc agaagatggc aaataaagca g                                    31

<210> SEQ ID NO 27
<211> LENGTH: 180
<212> TYPE: DNA
<213> ORGANISM: Artificial Sequence
<220> FEATURE:
<223> OTHER INFORMATION: C-term fusion primer

<400> SEQUENCE: 27
cgcggagctc agagctattt aagttgctta acttttttcct cgtttcgagg ttccttagca    60
agtttaccac cagtaatacc aataaattta gaattagctt taatatattg agtaatacca   120
ataaatttag aattagcttt aatatattga ccaccgtcat tttctacctt atcttctacc   180

<210> SEQ ID NO 28
<211> LENGTH: 29
<212> TYPE: DNA
<213> ORGANISM: Artificial Sequence
<220> FEATURE:
<223> OTHER INFORMATION: JAT209 primer

<400> SEQUENCE: 28
cgcgcatatg aagatggcaa ataaagcag                                       29

<210> SEQ ID NO 29
<211> LENGTH: 32
<212> TYPE: DNA
<213> ORGANISM: Artificial Sequence
<220> FEATURE:
<223> OTHER INFORMATION: JAT210 primer

<400> SEQUENCE: 29
cgcgggatcc agagctattt aagttgctta ac                                   32

<210> SEQ ID NO 30
<211> LENGTH: 127
<212> TYPE: DNA
<213> ORGANISM: Artificial Sequence
<220> FEATURE:
<223> OTHER INFORMATION: Construct 2 primer

<400> SEQUENCE: 30
cgcgcatatg gcttgtaaaa aagccgagga tcaaaaagaa gaagatcgcc gtaactaccc     60
aaccaatact tacaaaacgc ttgaacttga atgtgctgag ggtggtgcaa ataaagcagt   120
aaatgac                                                              127

<210> SEQ ID NO 31
<211> LENGTH: 35
<212> TYPE: DNA
<213> ORGANISM: Artificial Sequence
<220> FEATURE:
<223> OTHER INFORMATION: PLYNde1 primer

<400> SEQUENCE: 31
gcgcgcgcca tatggcaaat aaagcagtaa atgac                                35

<210> SEQ ID NO 32
<211> LENGTH: 87
<212> TYPE: DNA
<213> ORGANISM: Artificial Sequence
```

```
<220> FEATURE:
<223> OTHER INFORMATION: NEEK Sac1 primer

<400> SEQUENCE: 32
cgcgcggagc tcctatttac attgcttaac ttttcctcg tttcgaggtt ccttagcaca    60
ctctttgtca ttttctacct tatcctc                                      87

<210> SEQ ID NO 33
<211> LENGTH: 127
<212> TYPE: DNA
<213> ORGANISM: Artificial Sequence
<220> FEATURE:
<223> OTHER INFORMATION: YPT primer

<400> SEQUENCE: 33
cgcgcatatg gcttgtaaaa aagccgagga tcaaaagaa gaagatcgcc gtaactaccc    60
aaccaatact tacaaaacgc ttgaacttga atgtgctgag ggtggtgcaa ataaagcagt  120
aaatgac                                                           127

<210> SEQ ID NO 34
<211> LENGTH: 29
<212> TYPE: DNA
<213> ORGANISM: Artificial Sequence
<220> FEATURE:
<223> OTHER INFORMATION: JAT201b primer

<400> SEQUENCE: 34
cgcgtaacat atgatggcaa ataaagcag                                    29

<210> SEQ ID NO 35
<211> LENGTH: 181
<212> TYPE: DNA
<213> ORGANISM: Artificial Sequence
<220> FEATURE:
<223> OTHER INFORMATION: TCENEEK2 primer

<400> SEQUENCE: 35
cgcggagctc ctatttacat tgcttaactt ttcctcgtt tcgaggttcc ttagcacact    60
ctttaccacc agtaatacca ataaatttag aattagcttt aatatattga ccaccagtaa  120
taccaataaa tttagaatta gctttaatat attgaccacc gtcattttct accttatcct  180
c                                                                 181

<210> SEQ ID NO 36
<211> LENGTH: 34
<212> TYPE: DNA
<213> ORGANISM: Artificial Sequence
<220> FEATURE:
<223> OTHER INFORMATION: JAT215 primer

<400> SEQUENCE: 36
cgccgagctc ctagtcattt tctaccttat cctc                              34

<210> SEQ ID NO 37
<211> LENGTH: 33
<212> TYPE: DNA
<213> ORGANISM: Artificial Sequence
<220> FEATURE:
<223> OTHER INFORMATION: YPTNDE primer

<400> SEQUENCE: 37
cgcgcgcgca tatggcttgt aaaaaagccg agg                               33
```

<210> SEQ ID NO 38
<211> LENGTH: 40
<212> TYPE: DNA
<213> ORGANISM: Artificial Sequence
<220> FEATURE:
<223> OTHER INFORMATION: NeekSac primer

<400> SEQUENCE: 38

```
gcgcgcgagc tcttactatt tacattgctt aactttttcc                                40
```

<210> SEQ ID NO 39
<211> LENGTH: 471
<212> TYPE: PRT
<213> ORGANISM: Artificial Sequence
<220> FEATURE:
<223> OTHER INFORMATION: L460D pneumolysoid mutant

<400> SEQUENCE: 39

```
Met Ala Asn Lys Ala Val Asn Asp Phe Ile Leu Ala Met Asn Tyr Asp
  1               5                  10                  15

Lys Lys Lys Leu Leu Thr His Gln Gly Glu Ser Ile Glu Asn Arg Phe
             20                  25                  30

Ile Lys Glu Gly Asn Gln Leu Pro Asp Glu Phe Val Val Ile Glu Arg
         35                  40                  45

Lys Lys Arg Ser Leu Ser Thr Asn Thr Ser Asp Ile Ser Val Thr Ala
     50                  55                  60

Thr Asn Asp Ser Arg Leu Tyr Pro Gly Ala Leu Leu Val Val Asp Glu
 65                  70                  75                  80

Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Arg
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300
```

-continued

```
Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Asp Tyr Pro Gln Val
    450                 455                 460

Glu Asp Lys Val Glu Asn Asp
465                 470
```

METHODS AND COMPOSITIONS EMPLOYING IMMUNOGENIC FUSION PROTEINS

CROSS-REFERENCE TO RELATED APPLICATIONS

The present application is a divisional of U.S. application Ser. No. 14/007,159, filed on Oct. 2, 2013, which is a U.S. National Stage Application of PCT/US2012/030241, filed Mar. 23, 2012, which claims priority to U.S. Provisional Application No. 61/468,407, filed Mar. 28, 2011, the entire specification of each being incorporated herein by reference.

FIELD OF THE INVENTION

The present invention relates to the field of vaccines for preventing or treating pneumococcal infection.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 416012SEQLIST.txt, created on Feb. 21, 2012, and having a size of 82 KB and is filed concurrently with the specification. The sequence listing contained in this ASCII formatted document is part of the specification and is herein incorporated by reference in its entirety.

BACKGROUND OF THE INVENTION

*Streptococcus pneumoniae* is a gram positive bacterium which is a major cause of invasive infections such as sepsis, meningitis, otitis media and lobar pneumonia (Tuomanen et al. NEJM 322:1280-1284, 1995). Infection by *S. pneumoniae* remains a significant health threat worldwide. Pneumococci bind avidly to cells of the upper and lower respiratory tract and to endothelial cells present in blood vessels. Like most bacteria, adherence of pneumococci to human cells is achieved by presentation of bacterial surface proteins that bind to eukaryotic cell surface proteins (Cundell, D. & Tuomanen, E. (1994) *Microb Pathog* 17:361-374). For example, bacteria translocate across cells of the upper respiratory tract and nasopharynx via the polymeric immunoglobulin receptor (pIgR) (Zhang et al. (2000) *Cell* 102:827-837). Alternatively, when the bacteria are in the blood stream, the pneumococcal bacteria bind to endothelial cells, and the bacteria cross the blood vessel endothelium and enter tissues by binding to and transcytosing with the platelet activating factor (PAF) receptor (Cundell et al. (1995) *Nature*, 377:435-438).

Current vaccines against *S. pneumoniae* employ purified carbohydrates of the capsules of up to the 23 most common serotypes of this bacterium, but such vaccines are only 50% protective against pneumonia (Shapiro et al. *NJEM* 325: 1453, 1991) and are not immunogenic under the age of 2. Conjugate vaccines are based on pneumococcal capsular carbohydrates linked to proteins such as diphtheria toxoid or tetanus toxoid. Protection against pneumonia, sepsis, or meningitis for these vaccines is limited to the serotypes present in the formulation, thereby leaving patients unprotected against most of the ninety-two serotypes of this bacterium. Further, vaccines that are protective against both the colonization of pneumococcal bacteria in the nasopharynx, as well, as against entry of pneumococcal bacteria into the bloodstream are needed in the art. Therefore, compositions and methods provided herein fills a long felt need by providing pharmaceutical compositions (e.g., vaccines) for the prevention and treatment of a wide range of serotypes of pneumococcal infections across all age groups.

BRIEF SUMMARY OF THE INVENTION

Compositions and methods are provided for the prevention and treatment of bacterial infections, including pneumococcal infections. Compositions provided herein comprise a variety of immunogenic fusion proteins, wherein at least one polypeptide component of a given fusion protein comprises a CbpA polypeptide and/or a cytolysoid polypeptide, or an active variant or fragment thereof. Methods are provided for the prevention and treatment of bacterial infections, including pneumococcal infections by employing the various immunogenic fusion proteins having at least one polypeptide component comprising a CbpA polypeptide and/or a cytolysoid polypeptide, or an active variant or fragment thereof.

BRIEF DESCRIPTION OF THE DRAWINGS

FIG. 3 demonstrates that the fusion protein elicits antibodies against both PdB and CbpA.

FIG. 8 provides antibody titers for various fusion proteins.

FIG. 10 provides antibody titers for various fusion proteins.

FIG. 12 shows the antibody titers of various fusion proteins.

FIG. 18 shows that the fusion protein is protective against meningitis compared to toxoid alone or negative control.

FIG. 19 shows that various fusion toxoid showed enhanced survival for bacterial challenges.

FIG. 21 summarizes the percent survival and percent of meningitis.

DETAILED DESCRIPTION OF THE INVENTION

Figure 1:
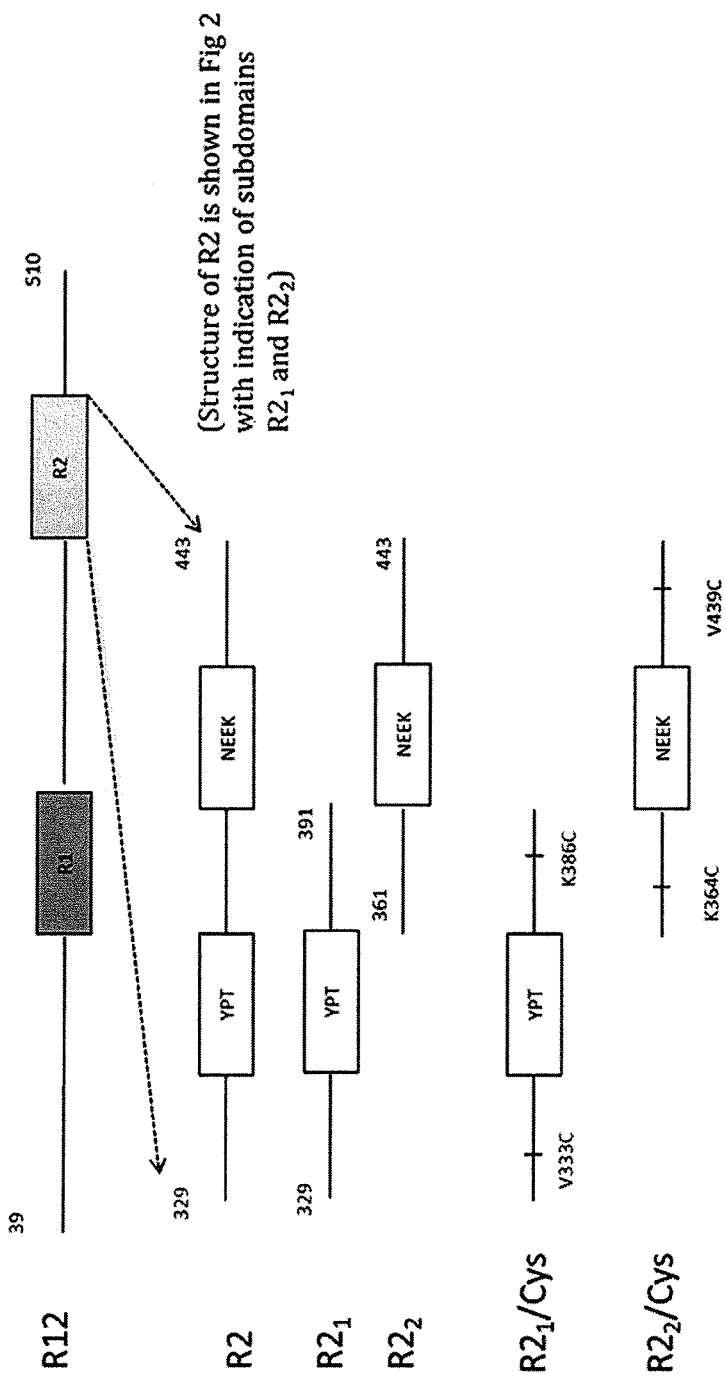
FIG. 1 illustrates the domain structure of CbpA and the fragments presented herein.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Compositions and methods are provided for the prevention and treatment of bacterial infections, including pneumococcal infections. Compositions provided herein comprise immunogenic fusion proteins comprising multiple operably linked polypeptides, wherein at least one polypeptide component of a given fusion protein comprises a CbpA polypeptide and/or a cytolysoid polypeptide, or an active variant or fragment thereof. The fusion of multiple genes encoding polypeptides together resulting in one fusion protein minimizes cost of vaccine production, and continues to allow for designs which provide efficacy to a breadth of serotypes.

The fusion proteins disclosed herein are immunogenic. As used herein, an "immunogen" is a substance that induces an immune response. The term "immunogenic" refers to the ability of a substance to induce an immune response when administered to an animal. A substance such as a polypeptide displays "increased immunogenicity" relative to another polypeptide when administration of the first polypeptide to an animal results in a greater immune response than that observed with administration of the other polypeptide. An increase in immunogenicity can also refer to not only a greater response in terms of the production of more antibody or T cells but also the production of more protective antibody or T cells. Thus, in specific embodiments, an increase in immunogenicity refers to any statistically significant increase in the level of antibodies or T cells or antibody or T cell production or any statistically significant increase in a protective antibody response. Such an increase can include a 5%, 10%, 20%, 30%, 40%, 50%, 60%, 70%, 80%, 90%, 100% or higher increase in the level of antibodies or in the protective antibody response. The immunogenicity of a polypeptide can be assayed for by measuring the level of antibodies or T cells produced against the polypeptide. Assays to measure for the level of antibodies are known, for example, see Harlow and Lane (1988) *Antibodies, A Laboratory Manual* (Cold Spring Harbor Publications, New York), for a standard description of antibody generation, immunoassay formats and conditions that can be used to determine specific immunoreactivity. Assays for T cells specific to a polypeptide are known, as shown in Example 7 herein, or see, for example, Rudraraju et al. (2011) *Virology* 410:429-36, herein incorporated by reference. In other instances, increased immunogenicity can be detected as an improved clinical outcome, as discussed elsewhere herein.

I. Compositions

Compositions disclosed herein provide fusion proteins comprising a first polypeptide operably linked to a second polypeptide. As used herein, "fusion protein" refers to the in frame genetic linkage of at least two heterologous polypeptides. Upon transcription/translation, a single protein is made. In this way, multiple proteins, or fragments thereof can be incorporated into a single polypeptide. "Operably linked" is intended to mean a functional linkage between two or more elements. For example, an operable linkage between two polypeptides fuses both polypeptides together in frame to produce a single polypeptide fusion protein. In particular aspects, the fusion protein further comprises a third polypeptide. Multiple forms of immunogenic fusion proteins are disclosed herein and discussed in detail below.

A. Fusion Proteins Comprising Immunogenic Regions of Choline Binding Protein A (CbpA)

i. CbpA

Figure 2:
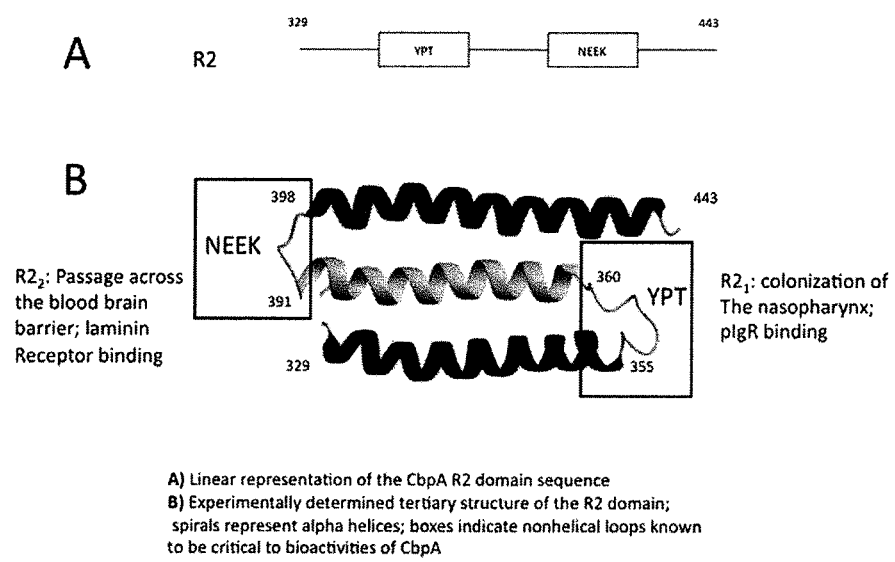
FIG. 2 illustrates the tertiary structure of CbpA R2 domain and points out the $R2_1$ and $R2_2$ regions.

Compositions and methods are provided comprising immunogenic fusion proteins comprising immunogenic regions of the Choline Binding Protein A (CbpA). As used herein, a "CbpA fusion protein" can comprise the full CbpA polypeptide or active variants or fragments thereof or any immunogenic fragment of CbpA as discussed in further detail elsewhere herein. CbpA is a 75 kD surface-exposed choline binding protein of *Streptococcus pneumoniae*. CbpA binds several ligands in the host including pIgR, C3, factor H and laminin receptor. The N-terminus of CbpA (region without the terminal choline binding domain) contains numerous repeats of the leucine zipper motif that cluster within 5 domains termed the A, B, R1, R2, and C domains (FIG. 1). The R2 domain of CbpA (amino acid residues approximately 329 to 443) comprises three anti-parallel alpha-helices (FIG. 2). This three alpha-helix structure is similarly predicted for the R1 domain (Jordan et al. (2006) *J. Am. Chem. Soc.* 128(28):91199128). Notably, the R domains from the Tigr4 strain of *S. pneumoniae* are highly conserved among CbpA sequences from other pneumococcal strains.

While any immunogenic fragment or domain of CbpA can be used in the fusion proteins disclosed herein, in one embodiment, the fusion protein comprises at least one R2 domain or active variant or fragment of the R2 domain. The R2 domain of CpbA comprises two regions, $R2_1$ and $R2_2$, which have been shown to form a loop conformation at each of the two turns of the anti-parallel alpha-helices in the three-dimensional structure of the R2 domain. See FIG. 2 boxes. As discussed in U.S. Patent Publication No. 2010-0143394-A1, herein incorporated by reference, the loop conformation of the R2₁ and R2₂ regions increases the immunogenicity of the R2 regions. Thus, the fusion proteins disclosed herein can comprise at least one immunogenic fragment or variant of the R2 domain of CbpA, such as, as least 1, 2, 3, 4, or more copies of the R2 domain, the R2₁ region and/or the R2₂ region or active variants and fragments thereof.

The R2₁ and R2₂ regions of CbpA have defined functions in disease. The R2₁ region comprises the pIgR binding site. Binding of the R2₁ region of CbpA to the pIgR allows the pneumococcal bacteria to utilize endocytosis machinery to translocate across nasoparyngeal epithelial cells into the blood stream. This step is critical for bacterial colonization of the nasopharynx and entry of the bacteria into the blood stream.

The R2₁ polypeptide comprises the amino acid sequence set forth in SEQ ID NO: 1 or active variants or fragments thereof. In some embodiments, the immunogenic fusion proteins comprising at least one copy of the R2₁ region or active variants and fragments thereof can produce an immunogenic response which targets bacterial pIgR binding and colonization of the nasopharynx and entry into the blood stream.

The R2₂ region of CbpA comprises the laminin receptor binding site. When the R2₂ region of CbpA binds to the laminin receptor, it facilitates the hand off of the bacterium to platelet activating factor (PAF) receptor which carries the bacterium into the endothelial cell, across the blood vessel wall, out of the blood stream and into the tissues. Binding to the laminin receptor is a critical step for bacteria to cross the blood brain barrier and cause meningitis. The R2₂ polypeptide comprises the amino acid sequence set forth in SEQ ID NO: 2 or active variants or fragments thereof. In some embodiments, the immunogenic fusion proteins comprising the R2₂ region of CbpA or active variants and fragments thereof can produce an immunogenic response which targets laminin receptor binding, and thus the ability of the bacteria to cross the blood brain barrier and cause meningitis.

In light of the different activities of the R2₁ and R2₂ regions of CbpA, the immunogenic fusion proteins described herein can comprise one or more copies of the R2 regions or an active variant or fragment thereof, one or more copies of either the R2₁ region or the R2₂ region or active variants and fragment thereof, or a combination of both the R2₁ and R2₂ regions or active variant and fragments thereof. In view of the different functional aspects of the R2₁ and R2₂ regions, one can thereby design a fusion protein having immunogenic activity.

In specific embodiments, the R2₁ and/or R2₂ polypeptide or active variants and fragments thereof employed in the immunogenic fusion protein comprises a loop conformation similar to that present in the native protein. By "loop conformation" is intended a three dimensional protein structure stabilized in a loop structure by a synthetic linkage in the polypeptide. As used herein, a "synthetic linkage" comprises any covalent or non-covalent interaction that is created in the polypeptides that does not occur in the native protein. Any form of a synthetic linkage that can form a covalent or non-covalent bond between amino acids in the native or variant polypeptides can be used. Such synthetic linkages can include synthetic peptide bonds that are engineered to occur between amino acids present in either the native polypeptide or a variant thereof. The R2₁ and R2₂ polypeptides or active variants and fragments thereof may comprise any form of synthetic linkage that can result in the formation of a covalent bond between amino acids in the native CbpA protein or variant thereof. A synthetic linkage further includes any non-covalent interaction that does not occur in the native polypeptide. For example, loop polypeptides comprising the R2₁ and/or R2₂ region may be engineered to have cysteine residues that are not present in the native CbpA protein and that allow for the formation of a disulfide bridge that stabilizes the polypeptide in a loop conformation. Various methods are known in the art to form such loop conformations in a polypeptide. See, for example, Chhabra et al. (1998) *Tetrahedron Lett.* 39:1603-1606; Rohwedder et al. (1998) *Tetrahedron Lett.* 39:1175-1178; Wittmann & Seeberger (2000) *Angew. Chem. Int. Ed. Engl.* 39:4348-4352; and Chan et al. (1995) *J. Chem. Soc., Chem. Commun.* 21:2209-2210, all of which are herein incorporated by reference in their entirety. Non-limiting examples of R2₁ or R2₂ polypeptides with a loop conformation are discussed in, for example, U.S. Patent Publication No. 2010-0143394-A1, which is herein incorporated by reference in its entirety.

In one embodiment, the loop conformation of the R2₁ and R2₂ polypeptides is generated by at least a first cysteine residue and a second cysteine residue, where the first and the second cysteine residues form a disulfide bond such that the polypeptide is stabilized in a loop conformation. In some specific embodiments, the cysteine residues can be added to the N-terminal and C-terminal ends of the R2₁ and R2₂ polypeptides, or the cysteine residues may be added internally by substituting amino acids within the polypeptide sequence with cysteine residues such that the R2₁ and R2₂ polypeptides form a loop conformation. While not intending to be limited to a particular mechanism, it is believed that stabilization of the R2₁ and R2₂ polypeptides in a loop conformation more closely mimics the native conformation of these polypeptides within the CbpA protein. The R2₁ and R2₂ loop polypeptides thereby have increased protective immunogenicity relative to those polypeptides that are not stabilized in the loop conformation (e.g., linear versions of these polypeptides).

In one non-limiting embodiment, the looped R2₁ and R2₂ polypeptides or active variant or fragments thereof employed in the immunogenic fusion proteins have cysteine substitutions as set forth in SEQ ID NOS: 3 or 4, or active variants or fragments thereof. SEQ ID NO: 3 (AKA YPT) comprises amino acid residues 329-391 of the CbpA protein, wherein the valine at position 333 and the lysine at position 386 have each been substituted with a cysteine residue. SEQ ID NO: 4 (AKA NEEK) comprises amino acid residues 361-443 of the CbpA protein, wherein the lysine at position 364 and the valine at position 439 have each been substituted with a cysteine residue.

Active variants and fragments of the full-length CbpA polypeptide (SEQ ID NO: 12), the CbpA polypeptide without the choline binding domain (R1R2, SEQ ID NO: 13), the R2 domain of the CbpA polypeptide (SEQ ID NO: 14), the R2₁ region (SEQ ID NOS: 1 or 3) and/or the R2₂ region (SEQ ID NOS: 2 or 4) can be employed in the various fusion proteins disclosed herein. Such active variants can comprise at least 65%, 70%, 75%, 80%, 85%, 90%, 91%, 92%, 93%, 94%, 95%, 96%, 97%, 98%, 99% or more sequence identity to SEQ ID NOS: 1, 2, 3, 4, 12, 13 or 14, wherein the active variants retain biological activity and hence are immunogenic. Non-limiting examples of R2₁ and R2₂ polypeptide variants are disclosed, for example, in U.S. Patent Publication No. 2010-0143394-A1, herein incorporated by reference. Active fragment can comprises amino acid sequences having at least 5, 10, 15, 20, 25, 30, 35, 40, 50, 60, 70, 80, 100, 150, or more consecutive amino acids of any one of SEQ ID NOS: 1, 2, 3, 4, 12, 13 or 14, where the active fragments retain biological activity and hence are immunogenic.

ii. Other Components of CbpA Fusion Proteins

The immunogenicity of the fusion proteins disclosed herein can be increased through the addition of a heterologous T cell epitope (TCE). Thus, the fusion proteins disclosed herein further comprise at least one heterologous TCE fused in frame to a bacterial polypeptide or variant or fragment thereof (i.e. the CbpA polypeptide or active variant and fragment thereof). Thus, for example, an amino acid sequence for a TCE may be linked to a CbpA polypeptide or active variant or fragment thereof to increase the immunogenicity of the polypeptide relative to that of the same polypeptide lacking the TCE sequence.

As used herein, a "TCE" refers to a polypeptide sequence recognized by T cells. See, for example, El Kasmi et al. (2000) *J. Gen. Virol.* 81:729-735 and Obeid et al. (1995) *J. Virol.* 69:1420-1428; El Kasmi et al. (1999) *Vaccine* 17:2436-2445; El Kasmi et al. (1998) *Mol. Immunol.* 35:905-918; El Kasmi et al. (2000) *J. Gen. Virol.* 81:729-735; Obeid et al. (1995) *J. Virol.* 69:1420-1428; and Bouche et al. (2005) *Vaccine* 23:2074-2077. Polypeptides comprising a TCE sequence are generally between about 10-30, 30-50 or 50-90, or 90-100 amino acids, or up to a full length protein. While any amino acid sequence having a TCE can be used in the in the fusion proteins disclosed herein, non-limiting examples of TCE sequences are set forth in SEQ ID NOS: 15 and 16, or active variants and fragments thereof.

"Heterologous" in reference to a polypeptide is a polypeptide that originates from a different protein. The heterologous TCE sequence can originate from the same organism as the other polypeptide component of the fusion protein, or the TCE can be from a different organism than the other polypeptide components of the fusion protein.

In a specific embodiment, an immunogenic CbpA fusion protein comprises a first polypeptide having an $R2_1$ or $R2_2$ region of CbpA, for example, the amino acid sequence of SEQ ID NOS: 1, 2, 3 or 4, or active variants or fragments thereof, wherein the first polypeptide comprising either the $R2_1$ or $R2_2$ region of CbpA forms a loop conformation and is immunogenic, and the fusion protein comprises a second polypeptide comprising at least one heterologous TCE, fused in frame to the first polypeptide.

In some embodiments, the heterologous TCE employed in the CbpA fusion protein disclosed herein comprises an immunogenic pneumococcal polypeptide or an active variant or fragment thereof. In such embodiments, in addition to enhancing the immunogenicity of the first polypeptide by providing a TCE, employment of a second immunogenic pneumococcal polypeptide in the CbpA fusion proteins described herein provides another means to target the pneumococcal bacteria and improve immunogenicity against pneumococcal infections. Non-limiting examples of immunogenic pneumococcal proteins which can be employed in the CbpA fusion proteins disclosed herein, include, pneumolysin, pneumococcal surface protein A (PspA), neuraminidase A (nanA), β-N-acetylhexosaminidase (StrH), DnaK, or AliB protein or active variant and fragments thereof. Additional immunogenic pneumococcal polypeptides are known in the art and can be found, for example, in U.S. Pat. No. 6,042,838, U.S. Pat. No. 6,232,116, U.S. Patent Publication No. 2009/0170162A1, C. C. Daniels et al. (2010) *Infection and Immunity* 78:2163-72, and Zysk et al. (2000) *Infection and Immunity* 68:3740-3743, each of which is herein incorporated by reference in their entirety.

In one embodiment, the TCE of the CbpA fusion protein comprises a pneumolysoid polypeptide or a variant or fragment thereof. Pneumolysin is a pore forming toxin and is the major cytolysin produced by *Streptococcus pneumoniae*. Pneumolysin oligomerizes to form pores in cell membranes, and facilitates intrapulmonary bacterial growth and entry into the blood stream by its hemolytic and complement activating properties. The amino acid sequence of wild-type or native pneumolysin is set forth in SEQ ID NO: 5. As used herein, "pneumolysoid" refers to a modified pneumolysin (a pneumolysin toxoid), wherein the modification of the protein inactivates or reduces the oligomerization, hemolytic and/or complement activating properties of the pneumolysoid protein while still retaining immunogenic activity. A reduction in the toxicity of the pneumolysin protein (i.e. a reduction in oligomerization, hemolysis, and/or complement activation) comprises at least a 1%, 5%, 10%, 20%, 30%, 40%, 50%, 60%, 70%, 80%, 90% or greater statistically significant decrease relative to an appropriate control. Various methods to assay for pneumolysin activity are known in the art. For example, Example 10 described elsewhere herein, provides a detailed assay to determine hemolytic activity of pneumolysoids. Complement activation may be determined, for example, by a two-dimensional gel electrophoresis assay to detect conversion of C3. See, J. C. Paton et al. (1984) *Infection and Immunity* 43:1085-1087, herein incorporated by reference. Oligomerization of pneumolysin may be assessed, for example, by a combination of sucrose density gradient centrifugation and gel electrophoresis as described in F. D. Saunders et al. (1989) *Infection and Immunity* 57:2547-02552, herein incorporated by reference. Various pneumolysoids that can be employed in the various immunogenic fusion proteins provided herein are described in, for example, WO2005/108419, WO2005/108580, WO 90/06951, U.S. Patent Application No. 2009/0285846A1 and U.S. Patent Application No. 2010/0166795, which are herein incorporated by reference. WO2005/108419 and WO2005/108580 disclose pneumolysoids having a mutation (e.g. a substitution or deletion) within the region of amino acids 144 to 161 of the wild-type pneumolysin protein. These mutants have reduced oligomerization and/or hemolytic activity as compared to the wild-type pneumolysin, and are therefore less toxic. The mutant may have a substitution or deletion of one or more amino acids 144 to 161 of the wild-type pneumolysin sequence. Thus, the pneumolysoid may have a mutation at one or more of the amino acid residues 144, 145, 146, 147, 148, 149, 150, 151, 152, 153, 154, 155, 156, 157, 158, 159, 160 or 161 of wild-type pneumolysin. In addition, pneumolysoids having reduced hemolytic activity and having at least one amino acid substitution or deletion in at least one of the regions corresponding to amino acids 257-297, 367-397 or 424-437 of the wild-type pneumolysin are described in WO 90/06951.

The pneumolysoid set forth in SEQ ID NO: 7, or an active variant or fragment thereof, comprises a mutation of the lysine at amino acid position 460 to an aspartic acid residue (L460D) which renders the pneumolysoid non-hemolytic. This pneumolysoid is referred to herein as the "L460D" pneumolysoid and is disclosed in U.S. Patent Application No. 2009/0285846A1, herein incorporated by reference in its entirety. An active variant of SEQ ID NO: 7 is provided herein and is set forth in SEQ ID NO: 39. The active variant comprises an amino acid change from Lysine at position 208 to Arginine when compared to SEQ ID NO: 7.

The pneumolysoid set forth in SEQ ID NO:8, or an active variant or fragment thereof, comprises a substitution of asparagine in place of aspartic acid at amino acid position 385 and deletion of alanine 146 and arginine 147 of the wild-type pneumolysin sequence (Δ6N385 pneumolysoid). This Δ6N385 pneumolysoid is deficient in both hemolysis and complement activation and is disclosed in U.S. Patent Application No. 2010/0166795 and in T. J. Mitchell et al. (1991) *Molecular Microbiology* 5:1883-1888, herein incorporated by reference in their entirety.

The pneumolysoid set forth in SEQ ID NO: 17, or an active variant or fragment thereof, comprises an amino acid substitution of phenylalanine in place of tryptophan at amino acid position 433 of the wild-type pneumolysin sequence (PdB). This PdB pneumolysoid is deficient in hemolysis and is disclosed in U.S. Pat. No. 6,716,432, herein incorporated by reference in its entirety.

Active variants or fragments of the various pneumolysoids are provided herein. Such active variants can comprise at least 65%, 70%, 75%, 80%, 85%, 90%, 91%, 92%, 93%, 94%, 95%, 96%, 97%, 98%, 99% or more sequence identity to SEQ ID NOS: 5, 7, 8, 17 or 39. An active variant will retain immunogenic activity. Active variants of pneumolysin are well known in the art and find use as pneumolysoids. See, for example, US 2010/0166795 and US 2009/0285846A1, herein incorporated by reference. The art provides substantial guidance regarding the preparation of such variants, as described elsewhere herein. Thus, in one embodiment, the immunogenic CbpA fusion proteins can comprise the pneumolysoid set forth in SEQ ID NO: 7, 8, 17 or 39 or an active variant thereof having at least 80%, 85%, 90%, 91%, 92%, 93%, 94%, 95%, 96%, 97%, 98%, 99% sequence identity to the amino acid sequence of SEQ ID NO: 7, 8, 17 or 39, wherein the active variant is immunogenic.

iii. Non-Limiting Examples of CbpA/TCE Fusion Proteins

The immunogenic polypeptides as disclosed herein can be operably linked in a variety of ways to produce an immunogenic fusion protein. When a single CbpA polypeptide or active variant or fragment thereof is employed, the TCE can be fused to the N-terminal end or the C-terminal end of the CbpA polypeptide or active variant or fragment thereof. The fusion protein may comprise other protein components such as a linker peptide between the polypeptides of the fusion protein, or a peptide tag for affinity purification (for example at the N- or C-terminus).

In other embodiments, the CbpA immunogenic fusion proteins can comprise at least 1, 2, 3, 4, 5 or more of the $R2_1$ or $R2_2$ regions, or active variants or fragments thereof, operably linked to a heterologous TCE. In one embodiment, the immunogenic fusion protein can comprise a third polypeptide fused in frame to a first polypeptide or a second polypeptide comprising a TCE, wherein the third polypeptide is from a bacteria and is immunogenic. When multiple CbpA polypeptides or variants and fragments thereof are employed in the fusion protein, the TCE can be found at either the N-terminal or C-terminal end of the fusion protein, or alternatively can be located internally in the fusion protein so that it is flanked by CbpA polypeptide sequences. Using multiple regions of the same protein in the fusion protein, in combination with a TCE, may increase immunogenicity to the protein by inducing antibody responses to multiple regions of the protein.

In one embodiment, the immunogenic fusion protein comprises an $R2_1$ or $R2_2$ polypeptide in a loop conformation (i.e. SEQ ID NOS: 1, 2, 3 or 4) or active variants or fragments thereof, fused in frame to a heterologous TCE (i.e. a pneumococcal polypeptide or a pneumolysoid polypeptide such as those in SEQ ID NOS: 5, 7, 8, 17 or 39) or active variants or fragments thereof, fused in frame to a second $R2_1$ or $R2_2$ polypeptide in a loop conformation (i.e. SEQ ID NOS: 1, 2, 3 or 4) or active variants or fragments thereof. Table 1 provides a non-limiting list of the various structures encompassed by the CbpA fusion proteins disclosed herein.

In a specific embodiment, the immunogenic CbpA fusion protein comprises an $R2_1$ polypeptide comprising SEQ ID NOS: 1 or 3 or an active variant or fragment thereof in a loop conformation, the L460D pneumolysoid of SEQ ID NO: 7 or 39 or an active variant or fragment thereof, and an $R2_2$ polypeptide comprising SEQ ID NOS: 2 or 4 or an active variant or fragment thereof in a loop conformation. In a particular embodiment the immunogenic fusion protein comprises the amino acid sequence set forth in SEQ ID NO: 9 or an active variant or fragment thereof.

In other non-limiting embodiments, the immunogenic fusion protein comprises an $R2_1$ polypeptide comprising SEQ ID NOS: 1 or 3 or an active variant or fragment thereof in a loop conformation, the Δ6N385 pneumolysoid of SEQ ID NO: 8 or an active variant or fragment thereof, and an $R2_2$ polypeptide comprising SEQ ID NOS: 2 or 4 or an active variant or fragment thereof in a loop conformation. In a particular embodiment the immunogenic fusion protein comprises the amino acid sequence set forth in SEQ ID NO: 11 or an active variant or fragment thereof.

TABLE 1

Examples of CbpA fusion proteins*

| First Polypeptide | Second Polypeptide | Third Polypeptide |
|---|---|---|
| SEQ ID NOs: 1, 2, 3, 4 or active variants or fragments thereof | TCE | Any bacterial polypeptide |
| SEQ ID NOs: 1, 2, 3, 4 or active variants or fragments thereof | Pneumococcal polypeptide or active variant or fragment thereof | |
| SEQ ID NOs: 1, 2, 3, 4 or active variants or fragments thereof | Pneumolysoid or active variant or fragment thereof | |
| SEQ ID NOs: 1, 2, 3, 4 or active variants or fragments thereof | L460D (SEQ ID NO: 7 or 39 or active variant or fragment thereof) | |
| SEQ ID NOs: 1, 2, 3, 4 or active variants or fragments thereof | Δ6N385 (SEQ ID NO: 8 or active variant or fragment thereof) | |
| SEQ ID NOs: 1, 2, 3, 4 or active variants or fragments thereof | PdB (SEQ ID NO: 17 or active variant or fragment thereof) | |
| SEQ ID NO: 1 or an active variant or fragment thereof | Pneumococcal polypeptide or active variant or fragment thereof | SEQ ID NO: 1 or an active variant or fragment thereof |
| SEQ ID NO: 1 or an active variant or fragment thereof | Pneumolysoid or active variant or fragment thereof | SEQ ID NO: 1 or an active variant or fragment thereof |

TABLE 1-continued

Examples of CbpA fusion proteins*

| First Polypeptide | Second Polypeptide | Third Polypeptide |
|---|---|---|
| SEQ ID NO: 1 or an active variant or fragment thereof | L460D (SEQ ID NO: 7 or 39 or active variant or fragment thereof) | SEQ ID NO: 1 or an active variant or fragment thereof |
| SEQ ID NO: 1 or an active variant or fragment thereof | Δ6N385 (SEQ ID NO: 8 or active variant or fragment thereof) | SEQ ID NO: 1 or an active variant or fragment thereof |
| SEQ ID NO: 1 or an active variant or fragment thereof | PdB (SEQ ID NO: 17 or active variant or fragment thereof) | SEQ ID NO: 1 or an active variant or fragment thereof |
| SEQ ID NO: 1 or an active variant or fragment thereof | Pneumococcal polypeptide or active variant or fragment thereof | SEQ ID NO: 2 or an active variant or fragment thereof |
| SEQ ID NO: 1 or an active variant or fragment thereof | Pneumolysoid or active variant or fragment thereof | SEQ ID NO: 2 or an active variant or fragment thereof |
| SEQ ID NO: 1 or an active variant or fragment thereof | L460D (SEQ ID NO: 7 or 39 or active variant or fragment thereof) | SEQ ID NO: 2 or an active variant or fragment thereof |
| SEQ ID NO: 1 or an active variant or fragment thereof | Δ6N385 (SEQ ID NO: 8 or active variant or fragment thereof) | SEQ ID NO: 2 or an active variant or fragment thereof |
| SEQ ID NO: 1 or an active variant or fragment thereof | PdB (SEQ ID NO: 17 or active variant or fragment thereof) | SEQ ID NO: 2 or an active variant or fragment thereof |
| SEQ ID NO: 1 or an active variant or fragment thereof | Pneumococcal polypeptide or active variant or fragment thereof | SEQ ID NO: 4 or an active variant or fragment thereof |
| SEQ ID NO: 1 or an active variant or fragment thereof | Pneumolysoid or active variant or fragment thereof | SEQ ID NO: 4 or an active variant or fragment thereof |
| SEQ ID NO: 1 or an active variant or fragment thereof | L460D (SEQ ID NO: 7 or 39 or active variant or fragment thereof) | SEQ ID NO: 4 or an active variant or fragment thereof |
| SEQ ID NO: 1 or an active variant or fragment thereof | Δ6N385 (SEQ ID NO: 8 or active variant or fragment thereof) | SEQ ID NO: 4 or an active variant or fragment thereof |
| SEQ ID NO: 1 or an active variant or fragment thereof | PdB (SEQ ID NO: 17 or active variant or fragment thereof) | SEQ ID NO: 4 or an active variant or fragment thereof |
| SEQ ID NO: 2 or an active variant or fragment thereof | Pneumococcal polypeptide or active variant or fragment thereof | SEQ ID NO: 1 or an active variant or fragment thereof |
| SEQ ID NO: 2 or an active variant or fragment thereof | Pneumolysoid or active variant or fragment thereof | SEQ ID NO: 1 or an active variant or fragment thereof |
| SEQ ID NO: 2 or an active variant or fragment thereof | L460D (SEQ ID NO: 7 or 39 or active variant or fragment thereof) | SEQ ID NO: 1 or an active variant or fragment thereof |
| SEQ ID NO: 2 or an active variant or fragment thereof | Δ6N385 (SEQ ID NO: 8 or active variant or fragment thereof) | SEQ ID NO: 1 or an active variant or fragment thereof |
| SEQ ID NO: 2 or an active variant or fragment thereof | PdB (SEQ ID NO: 17 or active variant or fragment thereof) | SEQ ID NO: 1 or an active variant or fragment thereof |
| SEQ ID NO: 2 or an active variant or fragment thereof | Pneumococcal polypeptide or active variant or fragment thereof | SEQ ID NO: 2 or an active variant or fragment thereof |
| SEQ ID NO: 2 or an active variant or fragment thereof | Pneumolysoid or active variant or fragment thereof | SEQ ID NO: 2 or an active variant or fragment thereof |
| SEQ ID NO: 2 or an active variant or fragment thereof | L460D (SEQ ID NO: 7 or 39 or active variant or fragment thereof) | SEQ ID NO: 2 or an active variant or fragment thereof |
| SEQ ID NO: 2 or an active variant or fragment thereof | Δ6N385 (SEQ ID NO: 8 or active variant or fragment thereof) | SEQ ID NO: 2 or an active variant or fragment thereof |
| SEQ ID NO: 2 or an active variant or fragment thereof | PdB (SEQ ID NO: 17 or active variant or fragment thereof) | SEQ ID NO: 2 or an active variant or fragment thereof |
| SEQ ID NO: 2 or an active variant or fragment thereof | Pneumococcal polypeptide or active variant or fragment thereof | SEQ ID NO: 3 or an active variant or fragment thereof |
| SEQ ID NO: 2 or an active variant or fragment thereof | Pneumolysoid or active variant or fragment thereof | SEQ ID NO: 3 or an active variant or fragment thereof |
| SEQ ID NO: 2 or an active variant or fragment thereof | L460D (SEQ ID NO: 7 or 39 or active variant or fragment thereof) | SEQ ID NO: 3 or an active variant or fragment thereof |
| SEQ ID NO: 2 or an active variant or fragment thereof | Δ6N385 (SEQ ID NO: 8 or active variant or fragment thereof) | SEQ ID NO: 3 or an active variant or fragment thereof |
| SEQ ID NO: 2 or an active variant or fragment thereof | PdB (SEQ ID NO: 17 or active variant or fragment thereof) | SEQ ID NO: 3 or an active variant or fragment thereof |
| SEQ ID NO: 3 or an active variant or fragment thereof | Pneumococcal polypeptide or active variant or fragment thereof | SEQ ID NO: 2 or an active variant or fragment thereof |
| SEQ ID NO: 3 or an active variant or fragment thereof | Pneumolysoid or active variant or fragment thereof | SEQ ID NO: 2 or an active variant or fragment thereof |
| SEQ ID NO: 3 or an active variant or fragment thereof | L460D (SEQ ID NO: 7 or 39 or active variant or fragment thereof) | SEQ ID NO: 2 or an active variant or fragment thereof |
| SEQ ID NO: 3 or an active variant or fragment thereof | Δ6N385 (SEQ ID NO: 8 or active variant or fragment thereof) | SEQ ID NO: 2 or an active variant or fragment thereof |

TABLE 1-continued

Examples of CbpA fusion proteins*

| First Polypeptide | Second Polypeptide | Third Polypeptide |
|---|---|---|
| variant or fragment thereof | variant or fragment thereof) | variant or fragment thereof |
| SEQ ID NO: 3 or an active variant or fragment thereof | PdB (SEQ ID NO: 17 or active variant or fragment thereof) | SEQ ID NO: 2 or an active variant or fragment thereof |
| SEQ ID NO: 3 or an active variant or fragment thereof | Pneumococcal polypeptide or active variant or fragment thereof | SEQ ID NO: 3 or an active variant or fragment thereof |
| SEQ ID NO: 3 or an active variant or fragment thereof | Pneumolysoid or active variant or fragment thereof | SEQ ID NO: 3 or an active variant or fragment thereof |
| SEQ ID NO: 3 or an active variant or fragment thereof | L460D (SEQ ID NO: 7 or 39 or active variant or fragment thereof) | SEQ ID NO: 3 or an active variant or fragment thereof |
| SEQ ID NO: 3 or an active variant or fragment thereof | Δ6N385 (SEQ ID NO: 8 or active variant or fragment thereof) | SEQ ID NO: 3 or an active variant or fragment thereof |
| SEQ ID NO: 3 or an active variant or fragment thereof | PdB (SEQ ID NO: 17 or active variant or fragment thereof) | SEQ ID NO: 3 or an active variant or fragment thereof |
| SEQ ID NO: 3 or an active variant or fragment thereof | Pneumococcal polypeptide or active variant or fragment thereof | SEQ ID NO: 4 or an active variant or fragment thereof |
| SEQ ID NO: 3 or an active variant or fragment thereof | Pneumolysoid or active variant or fragment thereof | SEQ ID NO: 4 or an active variant or fragment thereof |
| SEQ ID NO: 3 or an active variant or fragment thereof | L460D (SEQ ID NO: 7 or 39 or active variant or fragment thereof) | SEQ ID NO: 4 or an active variant or fragment thereof |
| SEQ ID NO: 3 or an active variant or fragment thereof | Δ6N385 (SEQ ID NO: 8 or active variant or fragment thereof) | SEQ ID NO: 4 or an active variant or fragment thereof |
| SEQ ID NO: 3 or an active variant or fragment thereof | PdB (SEQ ID NO: 17 or active variant or fragment thereof) | SEQ ID NO: 4 or an active variant or fragment thereof |
| SEQ ID NO: 4 or an active variant or fragment thereof | Pneumococcal polypeptide or active variant or fragment thereof | SEQ ID NO: 1 or an active variant or fragment thereof |
| SEQ ID NO: 4 or an active variant or fragment thereof | Pneumolysoid or active variant or fragment thereof | SEQ ID NO: 1 or an active variant or fragment thereof |
| SEQ ID NO: 4 or an active variant or fragment thereof | L460D (SEQ ID NO: 7 or 39 or active variant or fragment thereof) | SEQ ID NO: 1 or an active variant or fragment thereof |
| SEQ ID NO: 4 or an active variant or fragment thereof | Δ6N385 (SEQ ID NO: 8 or active variant or fragment thereof) | SEQ ID NO: 1 or an active variant or fragment thereof |
| SEQ ID NO: 4 or an active variant or fragment thereof | PdB (SEQ ID NO: 17 or active variant or fragment thereof) | SEQ ID NO: 1 or an active variant or fragment thereof |
| SEQ ID NO: 4 or an active variant or fragment thereof | Pneumococcal polypeptide or active variant or fragment thereof | SEQ ID NO: 3 or an active variant or fragment thereof |
| SEQ ID NO: 4 or an active variant or fragment thereof | Pneumolysoid or active variant or fragment thereof | SEQ ID NO: 3 or an active variant or fragment thereof |
| SEQ ID NO: 4 or an active variant or fragment thereof | L460D (SEQ ID NO: 7 or 39 or active variant or fragment thereof) | SEQ ID NO: 3 or an active variant or fragment thereof |
| SEQ ID NO: 4 or an active variant or fragment thereof | Δ6N385 (SEQ ID NO: 8 or active variant or fragment thereof) | SEQ ID NO: 3 or an active variant or fragment thereof |
| SEQ ID NO: 4 or an active variant or fragment thereof | PdB (SEQ ID NO: 17 or active variant or fragment thereof) | SEQ ID NO: 3 or an active variant or fragment thereof |
| SEQ ID NO: 4 or an active variant or fragment thereof | Pneumococcal polypeptide or active variant or fragment thereof | SEQ ID NO: 4 or an active variant or fragment thereof |
| SEQ ID NO: 4 or an active variant or fragment thereof | Pneumolysoid or active variant or fragment thereof | SEQ ID NO: 4 or an active variant or fragment thereof |
| SEQ ID NO: 4 or an active variant or fragment thereof | L460D (SEQ ID NO: 7 or 39 or active variant or fragment thereof) | SEQ ID NO: 4 or an active variant or fragment thereof |
| SEQ ID NO: 4 or an active variant or fragment thereof | Δ6N385 (SEQ ID NO: 8 or active variant or fragment thereof) | SEQ ID NO: 4 or an active variant or fragment thereof |
| SEQ ID NO: 4 or an active variant or fragment thereof | PdB (SEQ ID NO: 17 or active variant or fragment thereof) | SEQ ID NO: 4 or an active variant or fragment thereof |

*Table 1 denotes a fusion protein with the first polypeptide fused in frame to the second polypeptide optionally fused in frame to the third polypeptide. Reference to active variants and fragments of SEQ ID NOS: 1, 2, 3 or 4 in Table 1 further includes the polypeptide having a loop conformation.

B. Fusion Proteins Comprising Cytolysoids

As discussed above, the various CbpA fusion proteins provided herein can include a pneumolysoid polypeptide or active variant or fragment thereof to increase immunogenicity against pneumococcal infections. While CbpA is from pneumococcus it is recognized polypeptides from other type of bacteria could be used to generate an immunogenic fusion protein which can produce protective antibodies against other forms of bacteria, for example, bacteria from the genera *Clostridium, Streptococcus, Listeria, Bacillus*, and *Arcanobacterium*.

In one embodiment, the immunogenic fusion protein can comprise a cytolysoid polypeptide or active variant or fragment thereof. As used herein, a "cytolysoid fusion protein" can comprise a full length cytolysoid polypeptide or active variants or fragments thereof or any immunogenic fragment of cytolysoid as discussed in further detail elsewhere herein. Cytolysins are a family of pore-forming toxins that are produced by more than 20 species from the genera *Clostridium, Streptococcus, Listeria, Bacillus*, and *Arcanobacterium*. Each cytolysin is produced as a monomer and upon encountering a eukaryotic cell the monomers convert into an oligomeric structure to form a pore complex. Cytolysins are well known as hemolytic proteins. As used herein, "cytolysoid" refers to a modified cytolysin, wherein the modification of the protein inactivates or reduces the oligomerization and/or hemolytic properties of the cytolysoid protein while still retaining immunogenic activity. A reduction in the toxicity of the cytolysin protein (i.e. a reduction in oligomerization, and/or hemolysis) comprises at least a 1%, 5%, 10%, 20%, 30%, 40%, 50%, 60%, 70%, 80%, 90% or greater statistically significant decrease relative to an appropriate control. Various methods to assay for cytolysin activity are known in the art and are the same as described elsewhere herein for pneumolysin.

The art provides substantial guidance regarding the modifications required to inactivate or reduce the toxic activity (i.e. oligomerization and/or hemolysis) of cytolysins. These modifications may be amino acid substitutions, deletions, and/or additions. Such modifications are well known in the art. Some examples include, but are not limited to, WO2005/108419 and WO2005/108580 which disclose cytolysoids having a mutation (e.g. a substitution or deletion) within the region corresponding to amino acids 144 to 161 of the wild-type pneumolysin protein. This region of pneumolysin has a consensus sequence that is shared among the cytolysins. These mutant cytolysins have reduced oligomerization and/or hemolytic activity as compared to the wild-type cytolysin, and are therefore less toxic. The mutant may have a substitution or deletion of one or more amino acids within the regions corresponding to amino acids 144 to 161 of the wild-type pneumolysin sequence. Thus, the cytolysoid may have a mutation at one or more of the amino acids residues corresponding to amino acids 144, 145, 146, 147, 148, 149, 150, 151, 152, 153, 154, 155, 156, 157, 158, 159, 160 or 161 of wild-type pneumolysin. Additional, non-limiting, examples of cytolysoids in the art are disclosed in U.S. Patent Application No. 2009/0285846A1 and U.S. Patent Application No. 2010/0166795, which are herein incorporated by reference.

Any cytolysin can be modified to a cytolysoid and employed in the fusion proteins presented herein. Examples include, but are not limited to, pneumolysin from *Streptococcus pneumoniae*, perfringolysin O from *Clostridium perfringens*, intermedilysin from *Streptococcus intermedius*, alveolysin from *Bacillus alvei*, anthrolysin from *Bacillus anthracis*, putative cereolysin from *Bacillus cereus*, ivanolysin O from *Listeria ivanovii*, pyolysin from *Arcanobacterium pyogenes*, seeligeriolysin O from *Listeria seeligeri*, streptolysin O from *S. pyogenes*, suilysin from *Streptococcus suis*, tetanolysin from *Clostridium tetani*, listeriolysin O from *Listeria monocytogenes*, streptolysin O from *Streptococcus equisimilis*, streptolysin O from *S. canis*, thuringiolysin O from *Bacillus thuringiensis*, latersporolysin O from *B. laterosporus*, botulinolysin from *Clostridium botulinum*, chauveolysin from *C. chauvoei*, bifermentolysin from *C. bifermentans*, sordellilysin from *C. sordellii*, histolyticolysin from *Clostridium histiolyticum*, novylysin from *Clostridium novyi*, and septicolysin O from *Clostridium septicum*. Other examples of cytolysins and cytolysoids can be found, for example in S. E. Gelber et al. (2008) *J. Bacteriology* 190:3896-3903; and B. H. Jost et al. (2003) *Infection and Immunity* 71:2966-2969, herein incorporated by reference in their entirety.

The immunogenic cytolysoid fusion proteins provided herein can comprise at least 1, 2, 3, 4, 5 or more immunogenic bacterial polypeptides. The bacterial polypeptide source can include, but is not limited to, the above listed examples of cytolysin comprising bacteria. The immunogenic polypeptides of the cytolysoid fusion proteins disclosed herein can be assembled in various combinations. The cytolysoid can be at either at the N-terminal or C-terminal end of the fusion protein, or it can be flanked by immunogenic bacterial polypeptides. The immunogenic bacterial polypeptides can be from the same bacteria as the cytolysoid or they can be from different bacteria.

In a specific embodiment, the cytolysoid fusion protein comprises a pneumolysoid (i.e. SEQ ID NOS: 7, 8, 17 or 39 or active variants or fragments thereof) and the immunogenic bacterial polypeptides can comprise any immunogenic protein from pneumococcal bacteria.

Active variants or fragments of the various immunogenic cytolysoids are provided herein. Such active variants can comprise at least 65%, 70%, 75%, 80%, 85%, 90%, 91%, 92%, 93%, 94%, 95%, 96%, 97%, 98%, 99% or more sequence identity to a cytolysoid polypeptide provided herein in that they maintain immunogenic activity, as described elsewhere herein. Active variants of immunogenic cytolysoids are known in the art. See, for example, U.S. Patent Application No. 2009/0285846A1 and U.S. Patent Application No. 2010/0166795, herein incorporated by reference in their entirety.

C. Polynucleotides Encoding the Immunogenic Fusion Proteins and Methods of Making the Immunogenic Fusion Proteins Compositions further include isolated polynucleotides that encode the various immunogenic fusion proteins described herein above, and variants and fragments thereof. Exemplary polynucleotides comprising nucleotide sequences that encode the various polypeptides and the various fusion proteins are summarized in Table 4. Variants and fragments of the isolated polynucleotides disclosed herein are also encompassed.

Vectors and expression cassettes comprising the polynucleotides described herein are further disclosed. Expression cassettes will generally include a promoter operably linked to a polynucleotide and a transcriptional and translational termination region.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues.

An "isolated" polynucleotide is substantially or essentially free from components that normally accompany or interact with the polynucleotide as found in its naturally occurring environment. Thus, an isolated polynucleotide is substantially free of other cellular material or culture medium when produced by recombinant techniques, or substantially free of chemical precursors or other chemicals when chemically synthesized.

Conventional molecular biology, microbiology, and recombinant DNA techniques within the skill of the art may be employed herein. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The polypeptides and fusion proteins disclosed herein may be altered in various ways including amino acid substitutions, deletions, truncations, and insertions. Methods for such manipulations are generally known in the art. For example, amino acid sequence variants and fragments of the CbpA or cytolysoid proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. In specific embodiments employing the looped conformation of the $R2_1$ and $R2_2$ polypeptides, the mutation comprises at least an insertion or a substitution of a cysteine residue in a CbpA polypeptide disclosed herein. In other embodiments, the mutations in CbpA (the R2 domain, the $R2_1$ or the $R2_2$ region) pneumolysin or cytolysins comprise at least a deletion, insertion, and/or amino acid substitution.

A vector which comprises the above-described polynucleotides operably linked to a promoter is also provided herein. A nucleotide sequence is "operably linked" to an expression control sequence (e.g., a promoter) when the expression control sequence controls and regulates the transcription and translation of that sequence. The term "operably linked" when referring to a nucleotide sequence includes having an appropriate start signal (e.g., ATG) in front of the nucleotide sequence to be expressed and maintaining the correct reading frame to permit expression of the sequence under the control of the expression control sequence and production of the desired product encoded by the sequence. If a gene that one desires to insert into a recombinant nucleic acid molecule does not contain an appropriate start signal, such a start signal can be inserted in front of the gene. A "vector" is a replicon, such as plasmid, phage or cosmid, to which another nucleic acid segment may be attached so as to bring about the replication of the attached segment. The promoter may be, or is identical to, a bacterial, yeast, insect or mammalian promoter. Further, the vector may be a plasmid, cosmid, yeast artificial chromosome (YAC), bacteriophage or eukaryotic viral DNA.

Other numerous vector backbones known in the art as useful for expressing protein may be employed. Such vectors include, but are not limited to: adenovirus, simian virus 40 (SV40), cytomegalovirus (CMV), mouse mammary tumor virus (MMTV), Moloney murine leukemia virus, DNA delivery systems, i.e. liposomes, and expression plasmid delivery systems. Further, one class of vectors comprises DNA elements derived from viruses such as bovine papilloma virus, polyoma virus, baculovirus, retroviruses or Semliki Forest virus. Such vectors may be obtained commercially or assembled from the sequences described by methods well-known in the art.

A host vector system for the production of a polypeptide which comprises the vector of a suitable host cell is provided herein. Suitable host cells include, but are not limited to, prokaryotic or eukaryotic cells, e.g. bacterial cells (including gram positive cells), yeast cells, fungal cells, insect cells, and animal cells. Numerous mammalian cells may be used as hosts, including, but not limited to, the mouse fibroblast cell NIH 3T3, CHO cells, HeLa cells, Ltk⁻ cells, etc. Additional animal cells, such as R1.1, B-W and L-M cells, African Green Monkey kidney cells (e.g., COS 1, COS 7, BSC1, BSC40, and BMT10), insect cells (e.g., Sf9), and human cells and plant cells in tissue culture can also be used.

A wide variety of host/expression vector combinations may be employed in expressing the polynucleotide sequences presented herein. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences (sequences that control the expression of a nucleotide sequence operably linked to it) may be used in these vectors to express the polynucleotide sequences provided herein. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

It will be understood that not all vectors, expression control sequences and hosts will function equally well to express the polynucleotide sequences provided herein. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular nucleotide sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the nucleotide sequences to be expressed, and the ease of purification of the expression products.

In preparing the expression cassette, the various polynucleotides may be manipulated, so as to provide for the polynucleotide sequences in the proper orientation and, as appropriate, in the proper reading frame. Toward this end, adapters or linkers may be employed to join the polynucleotides or other manipulations may be involved to provide for convenient restriction sites, removal of superfluous DNA, removal of restriction sites, or the like. For example, linkers such as two glycines may be added between polypeptides. Methionine residues encoded by atg nucleotide sequences may be added to allow initiation of gene transcription. For this purpose, in vitro mutagenesis, primer repair, restriction, annealing, resubstitutions, e.g., transitions and trans versions, may be involved.

Further provided is a method of producing a polypeptide which comprises expressing a polynucleotide encoding a fusion protein disclosed herein in a host cell under suitable conditions permitting the production of the polypeptide and recovering the polypeptide so produced.

D. Methods of Use

These fusion proteins disclosed herein comprising two or more distinct immunogenic polypeptides represent a novel, cost effective, way to improve vaccine efficacy. The CbpA, cytolysoid fusion proteins provided herein (such as those examples provided in Tables 1 and 2) are immunogenic and depending on the design of the fusion protein and the choice of the polypeptide components, they find use in the treatment and prevention of a variety of bacterial infections.

The compositions provided herein find use in methods for preventing and treating bacterial infections. As used herein, "preventing a bacterial infection" is intended administration of a therapeutically effective amount of an immunogenic fusion protein, immunogenic composition, or vaccine provided herein to an animal in order to protect the animal from the development of a bacterial infection or the symptoms thereof. In some embodiments, a composition presented herein is administered to a subject, such as a human, that is at risk for developing a bacterial infection. By "treating a bacterial infection" is intended administration of a therapeutically effective amount of a fusion protein, immunogenic composition, or vaccine provided herein to an animal that has a bacterial infection or that has been exposed to a bacterium, where the purpose is to cure, heal, alleviate, relieve, alter, remedy, ameliorate, improve, or affect the condition or the symptoms of the bacterial infection.

A "therapeutically effective amount" as used herein refers to that amount which provides a therapeutic effect for a given condition and administration regimen. Thus, the phrase "therapeutically effective amount" is used herein to mean an amount sufficient to cause an improvement in a clinically significant condition in the host. In particular aspects, a "therapeutically effective amount" refers to an amount of an immunogenic fusion protein, immunogenic composition, or vaccine provided herein that when administered to an animal brings about a positive therapeutic response with respect to the prevention or treatment of a subject for a bacterial infection. A positive therapeutic response with respect to preventing a bacterial infection includes, for example, the production of antibodies by the subject in a quantity sufficient to protect against development of the disease. Similarly, a positive therapeutic response in regard to treating a bacterial infection includes curing or ameliorating the symptoms of the disease. In the present context, a deficit in the response of the host can be evidenced by continuing or spreading bacterial infection. An improvement in a clinically significant condition in the host includes a decrease in bacterial load, clearance of bacteria from colonized host cells, reduction in fever or inflammation associated with infection, or a reduction in any symptom associated with the bacterial infection.

In particular aspects, methods for preventing a pneumococcal infection in an animal comprise administering to the animal a therapeutically effective amount of an immunogenic fusion protein disclosed herein, an immunogenic composition comprising an immunogenic fusion protein disclosed herein in combination with a pharmaceutically acceptable carrier, or a vaccine disclosed herein, thereby preventing a pneumococcal infection. When treating or preventing pneumococcal infections, at least one of the various immunogenic fusion proteins comprising at least one polypeptide from pneumococcus will be used (e.g., a CbpA fusion protein, a fusion peptide from any other immunogenic pneumococcal protein or a pneumolysoid fusion protein, as discussed elsewhere herein). In other embodiments, methods for treating a pneumococcal infection in an animal infected with or exposed to a pneumococcal bacterium comprise administering to the animal a therapeutically effective amount of a fusion protein, an immunogenic composition comprising a fusion protein in combination with a pharmaceutically acceptable carrier, or a vaccine disclosed herein, thereby treating the animal. For example, in an individual already infected with a pneumococcal bacterium, an immunogenic fusion protein provided herein could be used as protection against the spread of the infection from the blood to the brain.

A method of inducing an immune response in a subject which has been exposed to or infected with a pneumococcal bacterium is further provided comprising administering to the subject a therapeutically effective amount of an immunogenic fusion protein provided herein (i.e., such as the fusion proteins listed in Tables 1 or 2), or a biologically active variant or fragment thereof, an immunogenic composition, or a vaccine as disclosed herein, thereby inducing an immune response.

Pneumococcal infection involves bacterial colonization of nasopharyngeal epithelial cells and subsequent bacterial entry into the bloodstream and, possibly, the brain. While not being bound by any theory, CbpA binds to pIgR during colonization of the nasopharynx by pneumococcal bacteria and to the laminin receptor during the invasive phase of the disease when the bacteria enter the bloodstream and the brain. The two binding activities have been localized to specific regions of the R2 domain of CbpA. In particular, the $R2_1$ region is responsible for binding to pIgR and bacterial colonization in the nasopharynx, whereas the $R2_2$ region is involved in binding to the laminin receptor and subsequent bacterial entry into the bloodstream and brain. This information can be utilized to develop immunogenic compositions and vaccines that are protective against both steps of pneumococcal infection, namely colonization of the nasopharynx and bacterial entry into the bloodstream.

In some embodiments, a fusion protein comprising, but not limited to, a CbpA polypeptide, or a biologically active variant or fragment thereof, can be employed in various methods to decrease pneumococcal colonization of the nasopharynx (i.e. a fusion protein comprising the $R2_1$ region of SEQ ID NOS: 1 or 3 or an active variant or fragment thereof, wherein the $R2_1$ region is in the loop conformation) or to decrease bacterial entry into the bloodstream and brain (i.e. a fusion protein comprising the $R2_2$ region of SEQ ID NOS: 2 or 4 or an active variant or fragment thereof, wherein said $R2_2$ region is in the loop conformation), or in other embodiments, can be used to decrease bacterial entry into the lung, into the bloodstream or across the blood brain barrier (i.e. a fusion protein comprising both an $R2_1$ and $R2_2$ sequence such as those sequences of (SEQ ID NOS: 1, 2, 3 or 4, or active variants or fragments thereof, wherein the $R2_1$ and/or the $R2_2$ are in the loop conformation). As used herein a "decrease" is meant at least a 1%, 5%, 10%, 20%, 30%, 40%, 50%, 60%, 70%, 80%, or 90% decrease relative to an appropriate control, or alternatively, decreased to a sufficient level to produce a desired therapeutic effect in the animal. Various methods to measure bacterial colonization are known in the art. For example, bacteria in the blood can be measured by taking a blood sample and spreading the blood out on an agar plate which contains the appropriate medium for bacterial growth. Bacteria in the nasopharynx can be measured by culturing bacteria from a swab or lavage of the nasopharynx or lungs of an animal. Bacteria that have crossed the blood brain barrier can be measured in a sample of cerebrospinal fluid or by detecting the physical attributes of meningitis in an animal, such as spinning of the head.

In further embodiments, a fusion protein comprising, but not limited to, any pneumococcal immunogenic polypeptide can be employed in various methods to treat and prevent pneumococcal infections.

In yet another embodiment, a fusion protein comprising a CbpA polypeptide provided herein can be employed in various methods to treat and prevent *Neisseria meningitidis* infection. *Neisseria meningitidis* is another bacterium that crosses the blood brain barrier and causes meningitis. As disclosed in U.S. Patent Publication No. 2010-0143394-A1, herein incorporated by reference, *Neisseria meningitidis* binds to the laminin receptor to cross the blood brain barrier. This is the same mechanism used by *Streptococcus pneumoniae*. Herein, in Example 4, is disclosed that fusion proteins comprising, but not limited to, the $R2_1$ or $R2_2$ regions, $R2_1$ or $R2_2$ regions having loop conformations or active variants or fragments thereof, of CbpA can cross-protect against *Neisseria meningitidis*. Therefore, the fusion proteins provided herein have use as a vaccine for the treatment and prevention of infections of other bacteria that utilize similar infectious mechanisms.

A fusion protein comprising a cytolysoid can be employed in various methods to treat and prevent bacterial infections. As discussed above, the cytolysoid polypeptides (or active variant or fragment thereof) can be modified from any bacterial cytolysin and be employed to create a fusion protein with one or more immunogenic polypeptides from the same bacterial source or a different bacterial source as the cytolysoid. In this way, methods to treat and prevent various bacterial infections are encompassed herein. Some examples of bacteria that may cause bacterial infections are disclosed elsewhere herein.

The immunogenic fusion proteins provided herein could also be used in various methods to treat or prevent multiple bacterial infections in an animal. The immunogenic fusion proteins could comprise a combination of immunogenic polypeptides from two or more bacteria. In a particular aspect, the immunogenic polypeptides of the fusion protein would originate from bacterial sources that are frequently found simultaneously in a given animal. For example, infections caused by *Streptococcus pneumoniae* and Haemophilus influenzae, which can simultaneously infect the nasopharynx, could be treated or prevented by a fusion protein comprising immunogenic polypeptides from both bacteria.

II. Pharmaceutical Compositions

Compositions further include immunogenic compositions and vaccines comprising an immunogenic fusion protein disclosed herein. Immunogenic compositions provided herein comprise at least one immunogenic fusion protein as described herein in combination with a pharmaceutically acceptable carrier. In some embodiments, the fusion protein is present in an amount effective to elicit antibody production when administered to an animal. Methods for detecting antibody production in an animal are well known in the art.

Vaccines for treating or preventing bacterial infection are provided and comprise at least one fusion protein provided herein in combination with a pharmaceutically acceptable carrier, wherein the fusion protein is present in an amount effective for treating or preventing a bacterial infection. In particular embodiments, the vaccine elicits production of protective antibodies against the bacteria when administered to an animal. In specific embodiments, the vaccine comprises an immunogenic fusion protein comprising a cytolysoid. In other embodiments, the vaccine comprises an immunogenic fusion protein comprising a cytolysoid and one or more immunogenic polypeptides from the same bacterial source or a different bacterial source as the cytolysoid.

Vaccines for treating or preventing pneumococcal infection are also provided and comprise at least one fusion protein provided herein in combination with a pharmaceutically acceptable carrier, wherein the fusion protein is present in an amount effective for treating or preventing a pneumococcal infection. In particular embodiments, the vaccine elicits production of protective antibodies against *Streptococcus pneumoniae* when administered to an animal. In specific embodiments, the vaccine comprises an immunogenic fusion protein comprising a CbpA polypeptide(s) (i.e. such as those fusion proteins presented in Table 1).

In addition, compositions comprising an immunogenic fusion protein or biologically active variant or fragment thereof and an adjuvant in combination with a pharmaceutically acceptable carrier are provided. The immunogenic fusion proteins presented herein can be prepared in an admixture with an adjuvant to prepare a vaccine. Pharmaceutically acceptable carriers and adjuvants are well known in the art. Methods for formulating pharmaceutical compositions and vaccines are generally known in the art. A thorough discussion of formulation and selection of pharmaceutical acceptable carriers, stabilizers, and isomolytes can be found in *Remington's Pharmaceutical Sciences* (18th ed.; Mack Publishing Company, Eaton, Pa., 1990), herein incorporated by reference. As provided herein, a vaccine may comprise, for example, at least one of the fusion proteins disclosed in Table 1 or a biologically active variant or fragment thereof.

As described elsewhere herein, the $R2_1$ region of CbpA is believed to be involved in bacterial colonization of the nasopharynx and the $R2_2$ region of CbpA mediates bacterial entry into the bloodstream. Thus a vaccine that comprises a fusion protein comprising both an $R2_1$ and an $R2_2$ polypeptide can provide protection against both steps involved in pneumococcal infection. In specific embodiments, a vaccine comprising a fusion protein comprising both an $R2_1$ and an $R2_2$ polypeptide, for example, the fusion protein of SEQ ID NO: 9 or active variants or fragments thereof, may provide protection against both steps involved in pneumococcal infection.

The immunogenic compositions and vaccines disclosed herein may further comprise a mixture of 1 or more fusion proteins with 1 or more polypeptides provided herein. A vaccine may comprise, for example, any one of the immunogenic fusion proteins described in Table 1 or active variants or fragments thereof combined as a mixture with one or more of the polypeptides set forth in SEQ ID NOS: 1, 2, 3, 4, 5, 7, 8, 12, 13, 14, 17 or 39 or active variants or fragments thereof.

Further provided is a vaccine for treating or preventing a *Neisseria meningitidis* infection comprising an immunogenic fusion protein disclosed herein (i.e. such as the fusion proteins presented in Table 1) and a pharmaceutically acceptable carrier. As disclosed elsewhere herein, fusion proteins comprising, but not limited to, the $R2_1$ or $R2_2$ regions, $R2_1$ or $R2_2$ regions having loop conformations or active variants or fragments thereof, of CbpA can cross-protect against *Neisseria meningitidis*.

III. Methods of Administration

The vaccines provided herein can be administered via any parenteral route, including, but not limited, to intramuscular, intraperitoneal, intravenous, and the like. Preferably, since the desired result of vaccination is to elucidate an immune response to the antigen, and thereby to the pathogenic organism, administration directly, or by targeting or choice of a viral vector, indirectly, to lymphoid tissues, e.g., lymph nodes or spleen, is desirable. Since immune cells are continually replicating, they are ideal targets for retroviral vector-based nucleic acid vaccines, since retroviruses require replicating cells.

Further, as used herein "pharmaceutically acceptable carrier" are well known to those skilled in the art and include, but are not limited to, 0.01-0.1 M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al, *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvant include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*.

Controlled or sustained release compositions include formulation in lipophilic depots (e.g. fatty acids, waxes, oils). Also comprehended herein are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions presented herein incorporate particulate forms protective coatings, protease inhibitors or permeation enhancers for various routes of administration, including parenteral, pulmonary, nasal and oral.

When administered, compounds are often cleared rapidly from mucosal surfaces or the circulation and may therefore elicit relatively short-lived pharmacological activity. Consequently, frequent administrations of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al, 1981; Newmark et al, 1982; and Katre et al, 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Dosages.

The sufficient amount may include but is not limited to from about 1 µg/kg to about 1000 mg/kg. The amount may be 10 mg/kg. The pharmaceutically acceptable form of the composition includes a pharmaceutically acceptable carrier.

The preparation of therapeutic compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An active component can be formulated into the therapeutic composition as neutralized pharmaceutically acceptable salt forms. Pharmaceutically acceptable salts include the acid addition salts (formed with the free amino groups of the polypeptide) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The component or components of a therapeutic composition provided herein may be introduced parenterally, transmucosally, e.g., orally, nasally, pulmonarily, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Oral or pulmonary delivery may be preferred to activate mucosal immunity; since pneumococci generally colonize the nasopharyngeal and pulmonary mucosa, mucosal immunity may be a particularly effective preventive treatment. The term "unit dose" when used in reference to a therapeutic composition provided herein refers to physically discrete units suitable as unitary dosage for humans, each unit containing a predetermined quantity of active material calculated to produce the desired therapeutic effect in association with the required diluent; i.e., carrier, or vehicle.

In another embodiment, the active compound can be delivered in a vesicle, in particular a liposome (see Langer (1990) *Science* 249:1527-1533; Treat et al, in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid).

In yet another embodiment, the therapeutic compound can be delivered in a controlled release system. For example, the fusion protein may be administered using intravenous infusion, an implantable osmotic pump, a transdermal patch, liposomes, or other modes of administration. In one embodiment, a pump may be used (see Langer, supra; Sefton (1987) *CRC Crit. Ref. Biomed. Eng.* 14:201; Buchwald et al. (1980) *Surgery* 88:507; Saudek et al. (1989) *N. Engl. J. Med.* 321:574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas (1983) *J. Macromol. Sci. Rev. Macromol. Chem.* 23:61; see also Levy et al. (1985) *Science* 228:190; During et al. (1989) *Ann. Neurol.* 25:351; Howard et al. (1989) *J. Neurosurg.* 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (1990) *Science* 249:1527-1533.

A subject in whom administration of an active component as set forth above is an effective therapeutic regimen for a bacterial infection is preferably a human, but can be any animal. Thus, as can be readily appreciated by one of ordinary skill in the art, the methods and pharmaceutical compositions provided herein are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

In the therapeutic methods and compositions provided herein, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations often nanomolar to ten micromolar in the blood are contemplated.

Administration with Other Compounds.

For treatment of a bacterial infection, one may administer the present active component in conjunction with one or more pharmaceutical compositions used for treating bacterial infection, including but not limited to (1) antibiotics; (2) soluble carbohydrate inhibitors of bacterial adhesin; (3) other small molecule inhibitors of bacterial adhesin; (4) inhibitors of bacterial metabolism, transport, or transformation; (5) stimulators of bacterial lysis, or (6) anti-bacterial antibodies or vaccines directed at other bacterial antigens. Other potential active components include anti-inflammatory agents, such as steroids and non-steroidal anti-inflammatory drugs. Administration may be simultaneous (for example, administration of a mixture of the present active component and an antibiotic), or may be in seriatim.

Also contemplated herein is pulmonary or intranasal delivery of the present fusion protein (or derivatives thereof). The fusion protein (or derivative) is delivered to the lungs of a mammal, where it can interfere with bacterial, i.e., streptococcal, and preferably pneumococcal binding to host cells. Other reports of preparation of proteins for pulmonary delivery are found in the art [Adjei et al. (1990) *Pharmaceutical Research*, 7:565-569; Adjei et al. (1990) *International Journal of Pharmaceutics*, 63:135-144 (leuprolide acetate); Braquet et al. (1989) *Journal of Cardiovascular Pharmacology*, 13 (suppl. 5): 143-146 (endothelin-1); Hubbard et al. (1989) *Annals of Internal Medicine, Vol. III, pp.* 206-212 (a 1-antitrypsin); Smith et al. (1989) *J. Clin. Invest.* 84:1145-1146 (α-1-proteinase); Oswein et al, "Aerosolization of Proteins", *Proceedings of Symposium on Respiratory Drug Delivery II*, Keystone, Colo., March, (1990) (recombinant human growth hormone); Debs et al. (1988) *J. Immunol.* 140:3482-3488 (interferon-γ and tumor necrosis factor alpha); Platz et al, U.S. Pat. No. 5,284,656 (granulocyte colony stimulating factor)]. A method and composition for pulmonary delivery of drugs is described in U.S. Pat. No. 5,451,569, issued Sep. 19, 1995 to Wong et al.

All such devices require the use of formulations suitable for the dispensing of a fusion protein provided herein (or derivative). Typically, each formulation is specific to the type of device employed and may involve the use of an appropriate propellant material, in addition to the usual diluents, adjuvant and/or carriers useful in therapy. Also, the use of liposomes, microcapsules or microspheres, inclusion complexes, or other types of carriers is contemplated. Chemically modified fusion proteins may also be prepared in different formulations depending on the type of chemical modification or the type of device employed.

Formulations suitable for use with a nebulizer, either jet or ultrasonic, will typically comprise at least one fusion protein (or derivative) dissolved in water at a concentration of about 0.1 to 25 mg of biologically active fusion protein per ml of solution. The formulation may also include a buffer and a simple sugar (e.g., for stabilization and regulation of osmotic pressure). The nebulizer formulation may also contain a surfactant, to reduce or prevent surface induced aggregation of the polypeptide caused by atomization of the solution in forming the aerosol.

Formulations for use with a metered-dose inhaler device will generally comprise a finely divided powder containing the fusion protein (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

The liquid aerosol formulations contain a fusion protein provided herein and a dispersing agent in a physiologically acceptable diluent. The dry powder aerosol formulations consist of a finely divided solid form of a fusion protein provided herein and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of pulmonary administration of a drug are well known in the art, and manipulation of formulations, aerosolization means and construction of a delivery device require at most routine experimentation by one of ordinary skill in the art. In a particular embodiment, the mass median dynamic diameter will be 5 micrometers or less in order to ensure that the drug particles reach the lung alveoli [Wearley, L. L. (1991) *Crit. Rev. in Ther. Drug Carrier Systems* 8:333].

Systems of aerosol delivery, such as the pressurized metered dose inhaler and the dry powder inhaler are disclosed in Newman, S. P., *Aerosols and the Lung*, Clarke, S. W. and Davia, D. editors, pp. 197-22 and can be used herein.

In a further embodiment, as discussed in detail infra, an aerosol formulation can include other therapeutically or pharmacologically active ingredients in addition to a fusion protein, such as but not limited to an antibiotic, a steroid, a non-steroidal anti-inflammatory drug, etc.

Liquid Aerosol Formulations.

Also provided are aerosol formulations and dosage forms for use in treating subjects suffering from bacterial, e.g., streptococcal, in particularly pneumococcal, infection. In general such dosage forms contain at least one fusion protein in a pharmaceutically acceptable diluent. Pharmaceutically acceptable diluents include but are not limited to sterile water, saline, buffered saline, dextrose solution, and the like. In a specific embodiment, a diluent that may be used in the pharmaceutical formulation provided herein is phosphate buffered saline or a buffered saline solution generally between the pH 7.0-8.0 range, or water.

The liquid aerosol formulation provided herein may include, as optional ingredients, pharmaceutically acceptable carriers, diluents, solubilizing or emulsifying agents, surfactants and excipients. The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

Further contemplated are liquid aerosol formulations comprising at least one fusion protein and another therapeutically effective drug, such as an antibiotic, a steroid, a non-steroidal anti-inflammatory drug, etc.

Aerosol Dry Powder Formulations.

It is also contemplated that the present aerosol formulation can be prepared as a dry powder formulation comprising a finely divided powder form of fusion proteins and a dispersant.

Formulations for dispensing from a powder inhaler device will comprise a finely divided dry powder containing at least one fusion protein (or derivative) and may also include a bulking agent, such as lactose, sorbitol, sucrose, or mannitol in amounts which facilitate dispersal of the powder from the device, e.g., 50 to 90% by weight of the formulation. The fusion protein (or derivative) should most advantageously be prepared in particulate form with an average particle size of less than 10 mm (or microns), most preferably 0.5 to 5 mm, for most effective delivery to the distal lung. In another embodiment, the dry powder formulation can comprise a finely divided dry powder containing a fusion protein, a dispersing agent and also a bulking agent. Bulking agents useful in conjunction with the present formulation include such agents as lactose, sorbitol, sucrose, or mannitol, in amounts that facilitate the dispersal of the powder from the device.

Also contemplated are dry powder formulations comprising at least one fusion protein and another therapeutically effective drug, such as an antibiotic, a steroid, a non-steroidal anti-inflammatory drug, etc.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the component or components (or chemically modified forms thereof) and inert ingredients which allow for protection against the stomach environment, and release of the biologically active material in the intestine.

Also specifically contemplated are oral dosage forms of the above derivatized component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis (1981) "Soluble Polymer-Enzyme Abducts" In: *Enzymes as Drugs*, Hocenberg and Roberts, eds., Wiley-Interscience, New York, N.Y., pp. 367-383; Newmark, et al (1982) *J. Appl. Biochem.* 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The peptide therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextran and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the fusion protein (or derivative) are for instance the fatty acids oleic acid, linoleic acid and linolenic acid.

Pulmonary Delivery.

Also contemplated herein is pulmonary delivery of the present fusion protein (or derivatives thereof). The fusion protein (or derivative) is delivered to the lungs of a mammal while inhaling and coats the mucosal surface of the alveoli. Other reports of this include Adjei et al. (1990) *Pharmaceutical Research* 7:565-569; Adjei et al. (1990) *International Journal of Pharmaceutics* 63:135-144 (leuprolide acetate); Braquet et al. (1989) *Journal of Cardiovascular Pharmacology* 13 (suppl. 5): 143-146 (endothelin-1); Hubbard et al. (1989) *Annals of Internal Medicine* Vol. III, pp. 206-212 (al-antitrypsin); Smith et al. (1989) *J. Clin. Invest.* 84:1145-1146 (a-1-proteinase); Oswein et al. (1990) "Aerosolization of Proteins", Proceedings of Symposium on Respiratory Drug Delivery II, Keystone, Colo., March, (recombinant human growth hormone); Debs et al. (1988) *J. Immunol.* 140:3482-3488 (interferon-g and tumor necrosis factor alpha) and Platz et al, U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use are a wide range of mechanical devices designed for pulmonary delivery of therapeutic products, including but not limited to nebulizers, metered dose inhalers, and powder inhalers, all of which are familiar to those skilled in the art.

Formulations suitable for use with a nebulizer, either jet or ultrasonic, will typically comprise fusion protein (or derivative) dissolved in water at a concentration of about 0.1 to 25 mg of biologically active protein per ml of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the fusion protein (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing fusion protein (or derivative) and may also include a bulking agent, such as lactose, sorbitol, sucrose, or mannitol in amounts which facilitate dispersal of the powder from the device, e.g., 50 to 90% by weight of the formulation. The fusion protein (or derivative) should most advantageously be prepared in particulate form with an average particle size of less than 10 mm (or microns), most preferably 0.5 to 5 mm, for most effective delivery to the distal lung.

Nasal Delivery.

Nasal or nasopharyngeal delivery of the fusion protein (or derivative) is also contemplated. Nasal delivery allows the passage of the fusion protein directly over the upper respiratory tract mucosal after administering the therapeutic product to the nose, without the necessity for deposition of the product in the lung. Formulations for nasal delivery include those with dextran or cyclodextran.

IV. Variants and Fragments of the Disclosed Polynucleotides and Polypeptides

Active variants and fragments of the disclosed polynucleotides and polypeptides are also employed in the immunogenic fusion proteins described herein. "Variants" refer to substantially similar sequences. As used herein, a "variant polypeptide" is intended to mean a polypeptide derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant polypeptides continue to possess the desired biological activity of the native polypeptide, that is, they are immunogenic. A variant of an polypeptide or polynucleotide sequence disclosed herein (i.e. SEQ ID NOS: 1-25 or 39) will typically have at least about 65%, 70%, 75%, 80%, 85%, 90%, 91%, 92%, 93%, 94%, 95%, 96%, 97%, 98%, 99% or more sequence identity with the reference sequence.

The term "fragment" refers to a portion of an amino acid or nucleotide sequence comprising a specified number of contiguous amino acid or nucleotide residues. In particular embodiments, a fragment of a polypeptide disclosed herein may retain the biological activity of the full-length polypeptide and hence be immunogenic. Fragments of a polynucleotide may encode protein fragments that retain the biological activity of the protein and hence be immunogenic. Alternatively, fragments of a polynucleotide that are useful as PCR primers generally do not retain biological activity. Thus, fragments of a nucleotide sequence disclosed herein (i.e. SEQ ID NOS: 6 or 10) may range from at least about 15, 20, 30, 40, 50, 60, 70, 80, 90, 100, 110, 120, 130, 140, 150, 175, 200, 225, 250, 300, 400, 500, 600, 700, 800, 900, 1000, 1100, 1200, 1300, 1400, or 1500 contiguous nucleotides or up to the full-length polynucleotide. Fragments of a polypeptide sequence disclosed herein (i.e. SEQ ID NOS: 1-5, 7-9, 11, 12-14, 17-25 or 39) may comprise at least 10, 15, 25, 30, 50, 60, 70, 80, 90, 100, 110, 120, 130, 140, 150, 160, 170, 180, 190, 200, 225, 250, 275, 300, 400, 425, 450, 475, or 500 contiguous amino acids, or up to the total number of amino acids present in a full-length protein.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence provided herein. To obtain gapped alignments for comparison purposes, Gapped BLAST (in BLAST 2.0) can be utilized as described in Altschul et al. (1997) *Nucleic*

Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix. By "equivalent program" is intended any sequence comparison program that, for any two sequences in question, generates an alignment having identical nucleotide or amino acid residue matches and an identical percent sequence identity when compared to the corresponding alignment generated by GAP Version 10.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

The following examples are provided by way of illustration, not by way of limitation.

EXPERIMENTAL

Background

Infection by *S. pneumoniae* remains a significant health threat worldwide. Shortcomings of the current vaccines include: restricted protective activity based on serotype, <50% protection against pneumonia, and production costs that are too high for developing world use. A new vaccine must be protein-based to be immunogenic in high-risk children under the age of 2 yrs. Thus, candidate vaccines should be composed of highly conserved proteins, preferably whose function is important in disease at multiple stages of infection. We have designed a vaccine composed of pneumolysoid (toxoid of pneumolysin) and CbpA. These proteins elicit some of the highest antibody titers in sera from humans exposed to pneumococci (McCool, T. et al. *Infect Immun* 71, 5724-5732 (2003)), their functions in disease pathogenesis are known, and involve processes in all body compartments (Rosenow, C. et al. *Mol Microbiol* 25, 819-829 (1997); Watson, D. et al. *Eur J Clin Microbiol Infect Dis* 195, 479-490 (1995)). There is strong preclinical data in animals suggesting protective activity across serotypes, and they are even more efficacious when used in combinations with each other (Palaniappan, R. et al. *Infect Immun* 73, 1006-1013 (2005); Briles, D. et al. *J Infect Dis* 188, 339-348 (2003); Ogunniyi, A., Woodrow, M., Poolman, J. & Paton, J. *Infect Immun* 69, 5997-6003 (2001)). To minimize cost but still provide efficacy to a breadth of serotypes, we have used genetic fusions of key components of these three proteins. Pneumolysoid has been used as a scaffold to which components of CbpA have been added.

Example 1: CbpA Peptide Fusions to PdB Pneumolysoid

Aim:

Construct and test a vaccine where genes encoding CbpA peptides are fused to the gene for pneumolysoid and the resulting single polypeptide has CbpA and pneumolysoid domains.

Conclude:

Peptide fusion is immunogenic for both toxoid and CbpA domains; Linear peptide fusion is not protective; looped peptide fusion is protective.

Significance:

CbpA peptide elicits antibody in the context of fusion to a toxoid and the antibody is protective and the tertiary looped structure of the peptide is preserved.

Background for Fusion of Proteins to CbpA Peptides

CbpA contains a region of important biological activity, termed R2 (SEQ ID NO: 14) which can be subdivided into two bioactive fragments YPT ($R2_1$ region) and NEEK ($R2_2$ region). These regions are shown in FIGS. 1 and 2. US 2010-0143394-A1 shows how these two regions can be used as vaccines and elicit the full protection that the entire CbpA protein confers. As shown in US 2010-0143394-A1 (FIG. 1), small peptides such as from the $R2_1$ or $R2_2$ regions are not recognized by the immune system and therefore do not generate a protective response when used alone as vaccines in a mouse model of pneumococcal infection. This is true even if the peptide is modified to be held in the appropriate folded tertiary conformation.

Also as shown in US 2010-0143394-A1, attaching the peptide to a protein makes the peptides part of a bigger molecule and it becomes detectable by the immune system and generates antibodies. Such proteins are "carriers" for the peptides. The carrier protein can be a T cell epitope (TCE) of the sequence listed in SEQ ID NO: 15 or 16 or a larger protein containing TCEs. Care must be taken to maintain the native three dimensional conformation of all the components in a fusion polypeptide so they do not interfere with each other and generate antibodies that recognize the conformation of the native protein from which the piece came.

Construction of Fusions Between CbpA Peptides and Pneumolysin Toxoid PdB

Since combinations of proteins can be more effective vaccines than single proteins alone but vaccines with more components are more expensive, we created genetic constructs where the gene sequences for the bioactive fragments of CbpA were linked directly to the gene for pneumolysoid PdB (detoxified pneumolysin). This is termed a 'fusion'. Upon transcription/translation, one protein is made from the fused gene parts. In this way, the important components of several proteins can be incorporated into one polypeptide.

The peptides of CbpA that are of particular interest are shown in FIG. 2 in boxes labeled YPT and NEEK (SEQ ID NOS: 1-4). This set of experiments tests two properties of the fusion of YPT and/or NEEK to pneumolysoid PdB. First (part 1) it tests if the small peptide fused to the larger PdB can be detected by the immune system, i.e. make antibody. Second (part 2) tests if the conformation of the YPT and/or NEEK as either linear or looped (native conformation) makes a difference in the protective activity of the immune response.

Two constructs were made and tested in experiments part 1 and 2:

Construct 1: Linear NEEK fused to PdB: The carrier protein pneumolysoid, PdB, was compared to PdB-2-TCEs-linear-NEEK (SEQ ID NO: 18), a construct modified to fuse a TCE and linear NEEK to the C terminus. The linear fragment is the native sequence but when not within the native protein it unfolds and becomes linear rather than looped as shown in FIG. 2. This linear form does not generate antibody to the native CbpA and therefore is not expected to be protective. Therefore, this construct tests if fusing any protein to pneumolysoid can generate specific antibodies to both the PdB and the peptide.

Construct 2: Looped YPT added to construct 1: This construct adds the looped YPT to construct 1 and tests if the looped YPT generates antibody and if that antibody is protective in the context of PdB and linear NEEK. The carrier protein pneumolysoid, PdB, was compared to looped-YPT-PdB-2TCEs-linear-NEEK (SEQ ID NO: 19), a construct modified to fuse a looped YPT domain on the N-terminus and a TCE with linear NEEK to the C-terminus.

Construct 1:

Primers were designed to add 2 tandem T-cell epitopes (TCE's) and linear NEEK sequence to PdB Pneumolysin toxoid. (This NEEK was linear and lacked cysteine linkers which allow loop formation.) All fusion peptides are linked together with two glycine residues denoted by the lowercase letters. Restriction sites are underlined. primers:

```
FORWARD
JAT 201
                                          (SEQ ID NO: 26)
5'-CgCgGGATCCAGAAGATGGCAAATAAAGCAG-3'

REVERSE
C-Term Fusion
                                          (SEQ ID NO: 27)
5'-CgCgGAGCTCAGAGCTATTTAAGTTGCTTAACTTTTTCCTCGTTTC GAGGTTCCTTAGCAAGTTTaccaccAGTAATACCAATAAATTTAGAATT

AGCTTTAATATATTGAGTAATACCAATAAATTTAGAATTAGCTTTAATA

TATTGaccaccGTCATTTTCTACCTTATCTTCTACC-3'
```

Recloned into pET15b with primers:

```
JAT209
                                          (SEQ ID NO: 28)
5'-CGCGCATATGAAGATGGCAAATAAAGCAG-3'

JAT210
                                          (SEQ ID NO: 29)
5'-CGCGGGATCCAGAGCTATTTAAGTTGCTTAAC-3'
```

Cloned into expression strain *E coli* BL21 (DE3) and expressed protein for immunization experiments.

Construct 2:

Designed a primer to put YPT on the N-terminus of the PdB fusion construct containing TCE's and NEEK. RNYPT construct contains two cysteine linkers to ensure loop formation. Cloned into pET15b and expressed for immunization experiments.

```
                                          (SEQ ID NO: 30)
5'-CGCGCATATGGCTTGTAAAAAAGCCGAGGATCAAAAAGAAGAAGAT

CGCCGTAACTACCCAACCAATACTTACAAAACGCTTGAACTTGAATGTG

CTGAGGGTGGTGCAAATAAAGCAGTAAATGAC-3'
```

Mouse Challenge for Protection:

Aim:

Compare immunogenicity and protective activity of PdB pneumolysoid, PdB linear peptide fusion (construct 1) and PdB looped peptide fusion (construct 2).

Experimental Design:

Testing to determine immunogenicity and protective efficacy was done in two parts.

Part 1: Immunogenicity of Toxoid Vs. Toxoid Fusion

Three groups of seven BALB/c mice (6 week old) were injected with 30 μg of PdB, PdB fusion linear peptide (PdB-2TCEs-linear NEEK), or PBS (saline). PHAD was used as adjuvant (200 μg/dose). Mice were boosted two weeks after priming and again two weeks after first boost. Mice were bled 1 week after last boost and serum tested by ELISA at 1:450 dilution for anti-NEEK, anti-CbpA R2, and anti-PdB antibodies.

Results as shown in FIG. 3 demonstrate that immunization with the fusion protein elicits antibodies against both PdB and CbpA while immunization with PdB alone does not elicit anti-CbpA antibodies.

Part 2: Protective Activity of Antibodies Generated by Toxoid Vs. Two Toxoid Fusions Four groups of 10 BALB/c mice were primed subcutaneously with 10 μg of immunogen using Alhydrogel (3.2 mg/ml) as adjuvant and subsequently boosted twice at two week intervals. Mice were challenged the following week intranasally with $2.7 \times 10^7$ *S. pnuemoniae* T4X and followed for survival.

Figure 4:
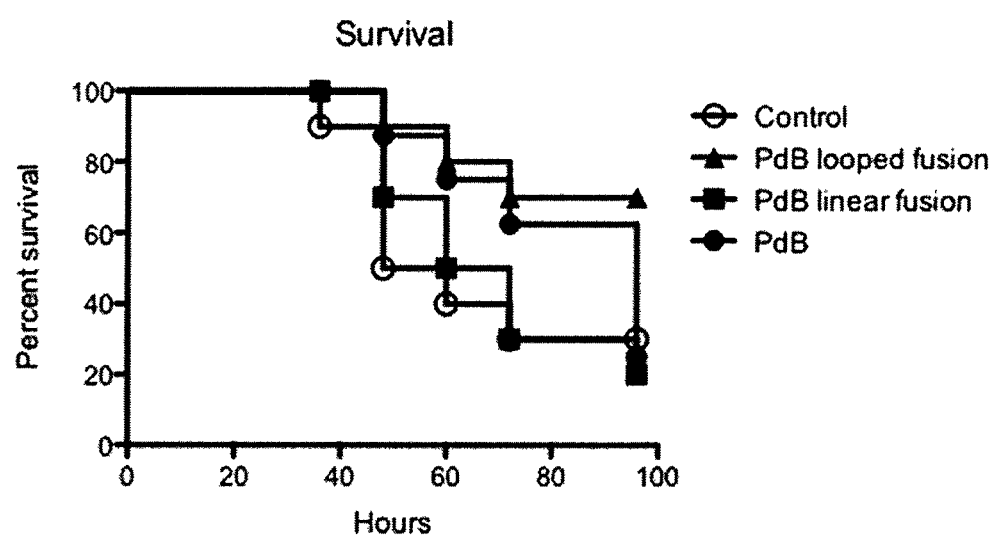
FIG. 4 demonstrates that when mice were challenged the following week intranasally with $2.7 \times 10^7$ *S. pneumoniae* T4X and followed for survival, the fusion protein elicited protection.

Results shown in FIG. 4 demonstrate that the fusion with the looped YPT adduct was protective while the fusion with the linear NEEK adduct was not. This indicates that using the looped technology, a fusion protein can be made that has the necessary tertiary structure to elicit protective antibodies.

Conclusions from Example 1

Both linear and looped peptide PdB fusions are immunogenic for both toxoid and CbpA. However, the linear peptide PdB fusion does not elicit protective antibody while the looped peptide PdB usion is protective. This confirms fusions are immunogenic but the loop technology in needed in constructing fusions to toxoid to retain the native shape of the peptide and therefore generate antibodies that are protective.

From this point forward for all examples only looped peptides of CbpA were used.

Example 2: CbpA Peptide Fusions to Δ6N385 Pneumolysoid

Aim:

Δ6N385 is a pneumolysoid distinct from PdB of Example 1. This experiment tests if peptide fusion to one or both ends of Δ6N385 is protective against pneumococcal sepsis and meningitis in mice.

Construction of Fusions to Δ6N385 Pneumolysoid

Δ6N385 is a mutant form of pneumolysin that is non-toxic as disclosed in US 2010/0166795, in particular paragraph 0068 and 0069 and in Mitchell et al, *Molecular Microbiology* 5:1883-1888, 1991. The following fusion proteins using Δ6N385 in pet33b as template were created:

1) Δ6N385-NEEK (Δ6N385-KECAKEPRNEEKVKQCK) (SEQ ID NO: 20)

2) YPT-Δ6N385-NEEK (ACKKAEDQKEEDRRNYPTNTYKTLELEC AE-Δ6N385-KECAKEPRNEEKVKQCK) (SEQ ID NO: 11)

3) Δ6N385-TCENEEK (Δ6N385-qyikanskfigitqyikanskf igitggKECAKEPRNEEKVKQCK)* (SEQ ID NO: 21)

4) YPT-Δ6N385 (ACKKAEDQKEEDRRNYPTNTYKTLELECAE- Δ6N385) (SEQ ID NO: 22)

5) YPT-Δ6N385-TCENEEK (ACKKAEDQKEEDRRNYPTNTYKTLE LECAE-Δ6N385-qyikanskfigitqyikanskfigitggKECA KEPRNEEKVKQCK) (SEQ ID NO: 23)

*lower case letters denote t-cell epitope (TCE)

For construct Δ6N385-NEEK, primers PLYNdel (gcgcgcgc-catatggcaaataaagcagtaaatgac) (SEQ ID NO: 31) and NEEK-SacI (cgcgcggagctcctatttacattgcttaacttttcctcgtttcgaggttccttag-cacactctttgtcatttt (SEQ ID NO: 32) were used to amplify by PCR. For construct YPT-Δ6N385-NEEK primers YPT (cgcgcatatggcttgtaaaaaagccgaggatcaaaaagaagaagatcgccg-taactacccaaccaatac ttacaaaacgcttgaacttgaatgtgctgagggtggtg-caaataaagcagtaaatgac) (SEQ ID NO: 33) and NEEKSacI were used. For construct Δ6N385-TCENEEK, primers JAT201b (cgcgtaacatatgatggcaaataaagcag) (SEQ ID NO: 34) and TCE-NEEK(2) (cgcggagctcctatttacattgcttaactttttc-ctcgtttcgaggttccttagcacactctttaccaccagtaataccaataat att-agcttttaatatattgaccaccagtaataccaataaatttagaattagctttaatatatt-gaccaccgtcattttctaccttatcctc) (SEQ ID NO: 35) were used. For construct YPT-Δ6N385, primers YPT and JAT215 (cgc-cgagctcctagtcattttctaccttatcctc) (SEQ ID NO: 36) were used. For construct YPT-Δ6N385-TCENEEK, primers YPT and TCE-NEEK(2) were used.

For each construct, the PCR product was digested overnight with NdeI and SacI and ligated into prepared vector pet33b. Clones were sequenced by the St. Jude Children's Research Hospital Hartwell Center. Clones containing the correct sequence were transformed into BL21 (DE3) competent cells. Over night LB cultures were back diluted 1:50 into fresh media and shaken at 37° C. to $OD_{600}=0.5$. Cultures were induced with 0.07 mM IPTG overnight at 22° C. E. Coli was lysed using Bugbuster HT reagent (Novagen) and purified over a Ni++ affinity column (Sigma). Protein was dialyzed into 10% glycerol/PBS. Endotoxin was removed and protein was further diluted into 50% glycerol and stored at −20° C.

Mouse Challenge for Protection Against Two Different Strains of Pneumococci

Aim:

Compare unmodified Δ6N385 to peptide fusion on one or both ends of Δ6N385 for immunogenicity and protective activity. Determine if protection is generated for both serotype 4 and serotype 2 pneumococci.

Experimental Design:

This Experiment was Repeated in 3 Parts:

Part 1. Are Fusions to Both Ends of Δ6N385 Protective Against Serotype 4 Meningitis and Death?

Mice used for this immunization were 6 week old female BalbC, 7 per group. Mice received 3 doses of antigen separated by 2 week intervals (Day 1, 15, 29). Mice were allowed to rest 3 weeks before challenge on day 50 with S. pneumoniae T4X. Bleeds for antibody titers (supernatant of a 75 μL bleed with heparanized capillary) were obtained by retro-orbital bleeding prior to immunization on day 1 and day 36. For each boost 10 μg of protein or 200 μg synthetic peptide were used with 200 μg adjuvant PHAD. Antigens used were as follows:

1) Δ6N385 (SEQ ID NO: 8)
2) Δ6N385-NEEK (SEQ ID NO: 20)
3) YPT-Δ6N385 (SEQ ID NO: 22)
4) YPT-Δ6N385-NEEK (SEQ ID NO: 11)
5) Δ6N385-TCENEEK (SEQ ID NO: 21)
6) YPT-Δ6N385-TCENEEK (SEQ ID NO: 23)
7) PBS (−) control (adjuvant alone)

Figure 5:
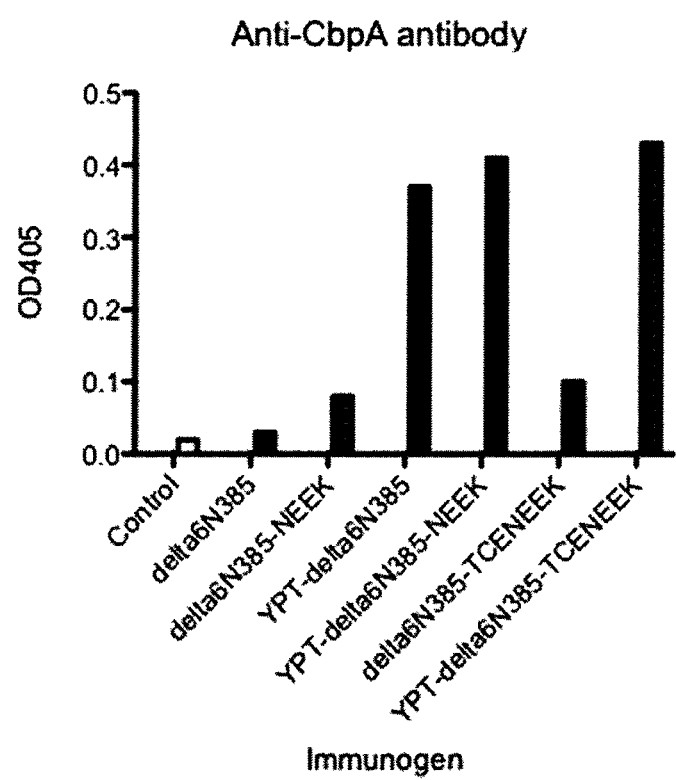
FIG. 5 provides the antibody titers for various fusion proteins.

Antibody titers were determined by ELISA against plates coated overnight at 4 C with rCbpA or wild type pneumolysin (rPLY) (100 ng/well). Serum samples were diluted 1/50, 1/150, 1/450 and 1/1050. Plates were blocked 2 hours with 10% FBS and then incubated with diluted serum for one hour at room temperature. Plates were washed 5 times and incubated 1 hour with anti-mouse IgG-AP (1:2000). Plates were washed 5× and incubated 20 minutes in AP-yellow substrate (Sigma). $OD_{405}$ readings were taken. The data for 1:450 dilution is set forth in FIG. 5 which shows high anti-CbpA antibodies elicited by the N-terminal YPT and C-terminal NEEK looped fusions.

Figure 6:
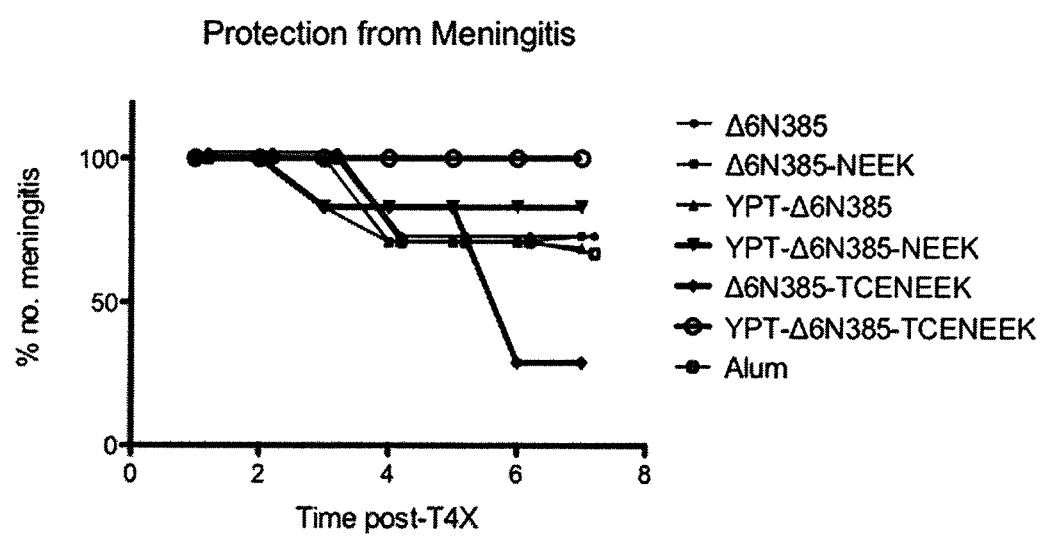
FIG. 6 provides the percent protection against meningitis for various fusion proteins.
Figure 7:
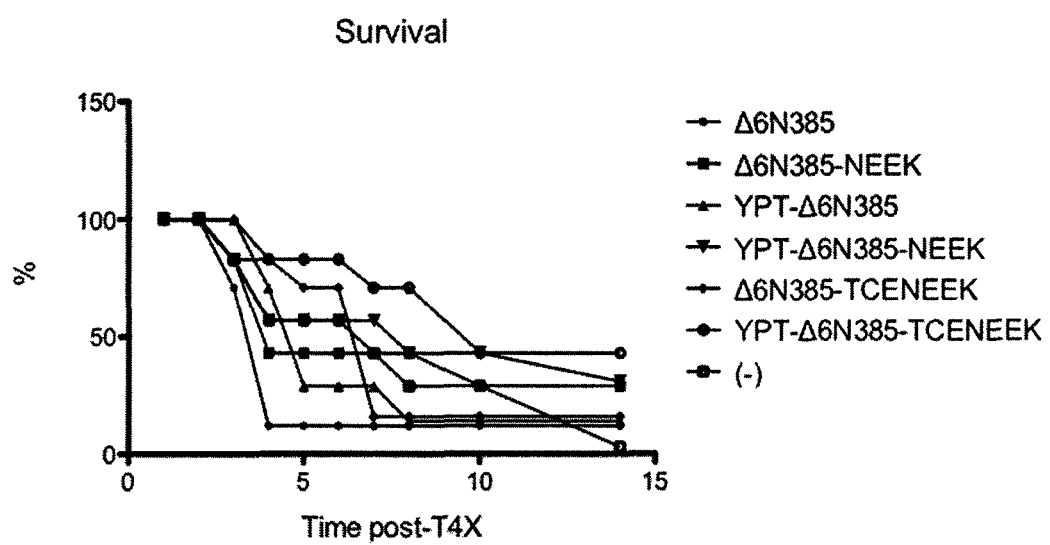
FIG. 7 provides the percent survival for various fusion proteins.

Mice were challenged with T4X ($1\times10^7$ cfu) intratracheally. Meningitis was determined by physical attributes (spinning of the head) and collecting cerebrospinal fluid (CSF) for bacterial number. Survival was monitored daily for 2 weeks. The data for percent protection against meningitis is set forth in FIG. 6. The data for percent survival is set forth in FIG. 7. These data show that fusion to both ends of pneumolysoid is protective against serotype 4 meningitis and death.

Part 2: Are Fusion Proteins Equal to or Better than Non-Fused Mixtures of Whole Proteins?

Mice used for this immunization were 6 week old female BalbC, 14 per group. Mice received 3 doses of antigen separated by 2 week intervals (Day 1, 15, 29). Mice were allowed to rest 3 weeks before intratracheal challenge on day 50 with S. pneumoniae T4X. Bleeds for antibody titers (supernatant of a 75 μL bleed with heparanized capillary) were obtained by retro-orbital bleeding prior to immunization on day 1 and day 36. For each boost 10 μg of protein was used with 100 μg adjuvant Alhydrogel (Sigma). Antigens used were as follows (fusions are #5 and 6):

1) WT PLY (SEQ ID NO: 5)
2) CbpA domain R2 (SEQ ID NO: 14)
3) Δ6N385 (SEQ ID NO: 8)
4) CbpA Domain R2 (SEQ ID NO: 14) mixed with Δ6N385 (SEQ ID NO: 8)
5) YPT-Δ6N385-NEEK (SEQ ID NO: 11)
6) YPT-Δ6N385-TCENEEK (SEQ ID NO: 23)
7) PBS (negative control, adjuvant alone)

Antibody titers were determined by ELISA against plates coated overnight at 4 C with rCbpA (100 ng/well). Serum samples were diluted 1/50, 1/150, 1/450 and 1/1050. Plates were blocked 2 hours with 10% FBS and then incubated with diluted serum for one hour at room temperature. Plates were washed 5 times and incubated 1 hour with anti-mouse IgG-AP (1:2000). Plates were washed 5× and incubated 20 minutes in AP-yellow substrate (Sigma). $OD_{405}$ readings were taken. The data for the 1/450 dilution is set forth in FIG. 8 and shows that the fusions are equivalent to mixtures of native proteins in generating antibody.

Figure 9:
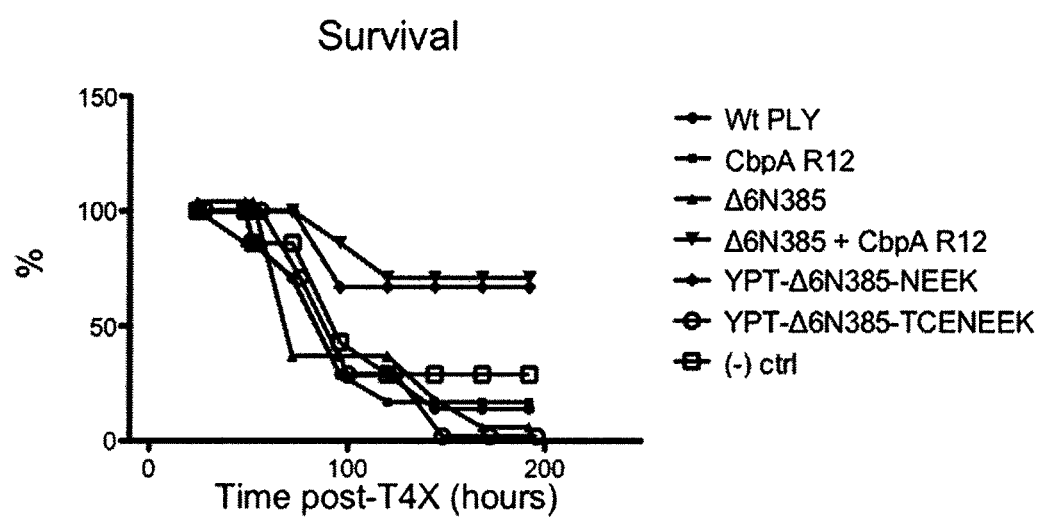
FIG. 9 provides the percent survival for various fusion proteins.

Mice were challenged with T4X (1×10⁷ cfu) intratracheally. Survival was monitored daily for 2 weeks. FIG. 9 provides the percent survival and shows that the fusion construct YPT-Δ6N385-NEEK is equivalent to the mixture of Δ6N385 and CbpA R2 and both are superior to either native protein alone.

Part 3: Are Mice Immunized with Fusion Protein of Sequence Serotype 4 Protected if Challenged with a Strain of Pneumococci of Serotype 2?
Mouse Challenge Mice used for this immunization were 6 week old female BalbC, 7 per group. Mice received 3 doses of antigen separated by 2 week intervals (Day 1, 15, 29). Mice were allowed to rest 3 weeks before intratracheal challenge on day 50 with *S. pneumoniae* D39 (serotype 2). Bleeds for antibody titers (supernatant of a 75 μL bleed with heparanized capillary) were obtained by retro-orbital bleeding prior to immunization on day 1 and day 36. For each boost 10 μg of protein was used with 100 μg adjuvant Alhydrogel (Sigma). Antigens used were as follows (fusions are #5 and 6):
1) WT PLY
2) CbpA domain R2 (SEQ ID NO: 14)
3) Δ6N385 (SEQ ID NO: 8)
4) CbpA Domain R2 (SEQ ID NO: 14) mixed with Δ6N385 (SEQ ID NO: 8)
5) YPT-Δ6N385-NEEK (SEQ ID NO: 11)
6) YPT-Δ6N385-TCENEEK (SEQ ID NO: 23)
7) PBS (negative control, adjuvant alone)

Antibody titers were determined by ELISA against plates coated overnight at 4 C with rCbpA (100 ng/well). Serum samples were diluted 1/50, 1/150, 1/450 and 1/1050. Plates were blocked 2 hours with 10% FBS and then incubated with diluted serum for one hour at room temperature. Plates were washed 5 times and incubated 1 hour with anti-mouse IgG-AP (1:2000). Plates were washed 5× and incubated 20 minutes in AP-yellow substrate (Sigma). $OD_{405}$ readings were taken. Final antibody titers at 1/450 dilution are shown in FIG. 10 and show the fusions are as immunogenic as mixtures of native proteins (replicates FIG. 8 results).

Figure 11:
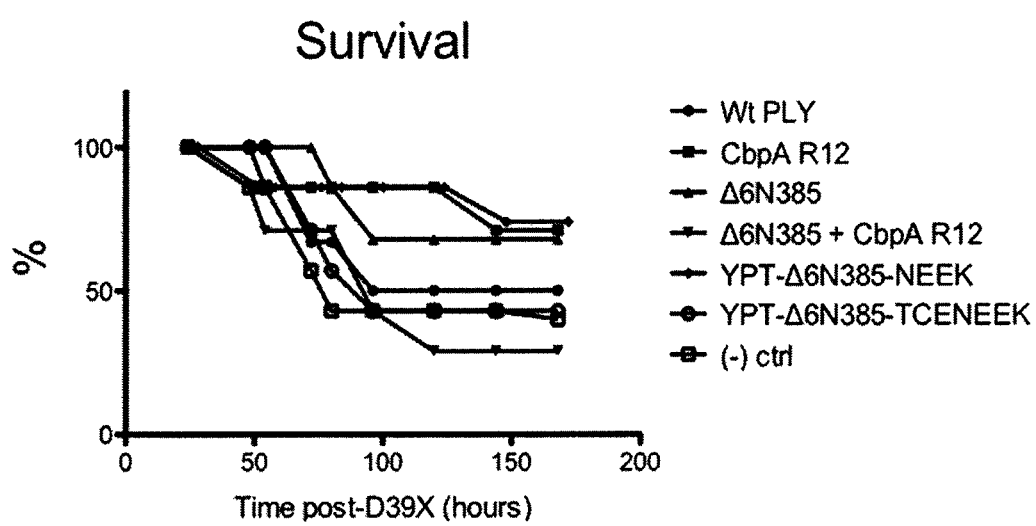
FIG. 11 shows the percent survival following administration of various fusion proteins.

Mice were challenged with D39X (3.5×10⁷ cfu) intratracheally. Survival was monitored daily for 2 weeks. FIG. 11 shows the percent survival and indicates the fusion is in the superior group of protection even if challenge is a heterologous serotype.

Conclusions from Example 2

Peptide fusion to Δ6N385 is immunogenic for both toxoid and CbpA. Peptide fusion to both ends of Δ6N385 is protective against meningitis and improves survival in an intratracheal challenge model. The fusion protein vaccine provides protection against a strain of pneumococci of a serotype 2 that is different than the serotype 4 immunizing sequence and protection is better than toxoid alone.

Significance:

This indicates that fusion of looped peptides and toxoid, specifically with modifications at both ends of the toxoid protein, improves vaccine efficacy and is as good or better than mixtures of the native proteins CbpA and pneumolysoid. Vaccine is effective across different serotypes.

Example 3: CbpA Peptide Fusions to L460D Pneumolysoid

Another toxoid of pneumolysin is the mutant changing the amino acid at 460 from Leucine (L) to Aspartic acid (D) (called L460D). This is disclosed in US 2009/0285846A1 by R. Tweten, herein incorporated by reference in its entirety. L460D is distinguished by more complete loss of the hemolytic activity of the native toxin than other pneumolysoids PdB or Δ6N385. This would potentially make it a superior carrier for fused peptides as it might be a less toxic vaccine.

The experiments disclosed herein that make reference to L460D could have contained either the pneumolysoid sequence set forth in SEQ ID NO: 7 or SEQ ID NO: 39. In all experiments, the two L460D pneumolysoids behaved identically and will be referred to from this point forward as L460D.

Aim:

Compare L460D as a carrier for the CbpA peptides to other fusion/toxoids for immunogenicity and protective activity.

Construction of Fusions to L460D Toxoid

The following CbpA-L460D fusion proteins using L460D as template were generated.
1) YPT-L460D-NEEK (SEQ ID NO: 9)
2) YPT-L460D-TCENEEK (SEQ ID NO: 24)

For construct YPT-L460D-NEEK primers YPT (CGCG-CATATGGCTTGTAA AAAAGCCGAGGAT-CAAAAAGAAGAAGATCGCCGTAACTACCCAAC-CAATACT TACAAAACGCTTGAACTTGAATGTGCTGAGGGTG-GTGCAAATAAAGCAGTAA ATGAC) (SEQ ID NO: 33) and NEEKSacI (cgcgcggagctcctatttacattgcttaactttttcctcg tttcgaggttccttagcacactctttgtcattttctaccttatcctc) (SEQ ID NO: 32) were used. For construct YPT-L460D-TCENEEK, primers YPT (SEQ ID NO: 33) and TCENEEK2 (cgcggagctcct-atttacattgcttaactttttcctcgtttcgaggttccttagcacactcttaccaccag-taa taccaataaatttagaattagctttaatatattgaccaccagtaataccaataaattta-gaattagctttaatata ttgaccaccgtcattttctaccttatcctc) (SEQ ID NO: 35) were used.

For each construct, the PCR product was digested overnight with NdeI and SacI and ligated into prepared vector pet33b. Clones were sequenced by the St. Jude Children's Research Hospital Hartwell Center. Clones containing the correct sequence were transformed into BL21(DE3) competent cells. Over night LB cultures were back diluted 1:50 into fresh media and shaken at 37° C. to OD600=0.5. Cultures were induced with 0.07 mM IPTG overnight at 22° C. *E. Coli* was lysed using Bugbuster H T reagent (Novagen) and purified over a Ni++ affinity column (Sigma). Protein was dialyzed into 10% glycerol/PBS. Endotoxin was removed and protein was further diluted into 50% glycerol and stored at −20° C.

Mouse Challenge: This Experiment was in Two Parts with Different Challenge Bacteria
Part 1: Challenge with Serotype 4 Pneumococci Mice used for this immunization were 6 week old female BalbC, 10 per group. Mice received 3 doses of antigen separated by 2 week intervals (Day 1, 15, 29). Mice were allowed to rest 3 weeks before challenge on day 50 with *S. pneumoniae* T4X. Bleeds for antibody titers (supernatant of a 75 μL bleed with heparanized capillary) were obtained by retro-orbital bleeding prior to immunization on day 1 and day 36.

For each boost 10 μg of protein was used with 100 μg adjuvant Alhydrogel (Sigma). Antigens used were as follows:
1) WT PLY (SEQ ID NO: 5)
2) Δ6N385 (SEQ ID NO: 8)
3) L460D (SEQ ID NO: 7)
4) YPT-L460D-NEEK (SEQ ID NO: 9)

5) YPT-L460D-TCENEEK (SEQ ID NO: 24)
6) PBS (−) (adjuvant alone)

Antibody titers were determined by ELISA against plates coated overnight at 4 C with rCbpA or rPLN (100 ng/well). Serum samples were diluted 1/50, 1/150, 1/450 and 1/1050. Plates were blocked 2 hours with 10% FBS and then incubated with diluted serum for one hour at room temperature. Plates were washed 5 times and incubated 1 hour with anti-mouse IgG-AP (1:2000). Plates were washed 5× and incubated 20 minutes in AP-yellow substrate (Sigma). $OD_{405}$ readings were taken. The data showing the antibody titers at 1/450 dilution is shown in FIG. 12 and indicates that fusions to L460D show superior antigenicity.

Figure 13:
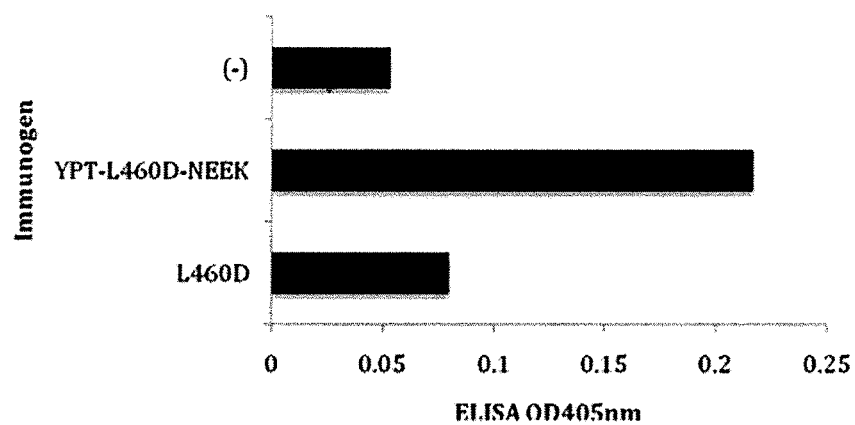
FIG. 13 shows the use of an anti-sera against L460D, YPT-L460D-NEEK and PBS (−) control in an ELISA based assay for recognition of *S. pneumoniae* T4R whole bacteria.

Anti-sera against L460D, YPT-L460D-NEEK and PBS (−) control were also tested for functional activity for binding to S. pneumoniae T4R whole bacteria in an ELISA based assay. Plates were coated with $1\times10^6$ cfu/well and ELISA protocol as previously described was used. The data is shown in FIG. 13. Antibody binding to intact bacteria was highest in the group YPT-L460D-NEEK.

Figure 14:
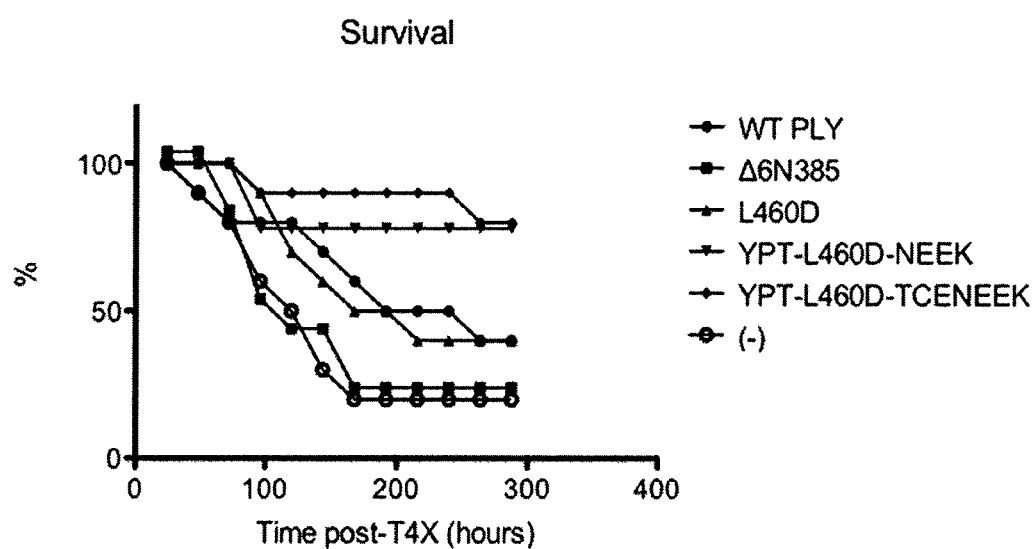
FIG. 14 shows the percent survival of various fusion proteins.

Mouse Challenge:

Mice were challenged with T4X ($1\times10^7$ cfu) intratracheally. Survival was monitored daily for 2 weeks. FIG. 14 shows the percent survival.

Fusion of L460D with two peptides is superior to one peptide and L460D is a superior carrier than Δ6N385.

Part 2: Challenge with Serotype 2 Pneumococci

Mouse Challenge

Mice used for this immunization were 6 week old female BalbC, 10 per group. Mice received 3 doses of antigen separated by 2 week intervals (Day 1, 15, 29). Mice were allowed to rest 3 weeks before challenge on day 50 with S. pneumoniae D39. Bleeds for antibody titers (supernatant of a 75 μL bleed with heparanized capillary) were obtained by retro-orbital bleeding prior to immunization on day 1 and day 36.

For each boost 10 μg of protein was used with 100 μg adjuvant Alhydrogel (Sigma). Antigens used were as follows:

1) WT PLY (SEQ ID NO: 5)
2) Δ6N385 (SEQ ID NO: 8)
3) L460D (SEQ ID NO: 7)
4) YPT-L460D-NEEK (SEQ ID NO: 9)
5) YPT-L460D-TCENEEK (SEQ ID NO: 24)
6) PBS (−) (adjuvant alone)

Figure 15:
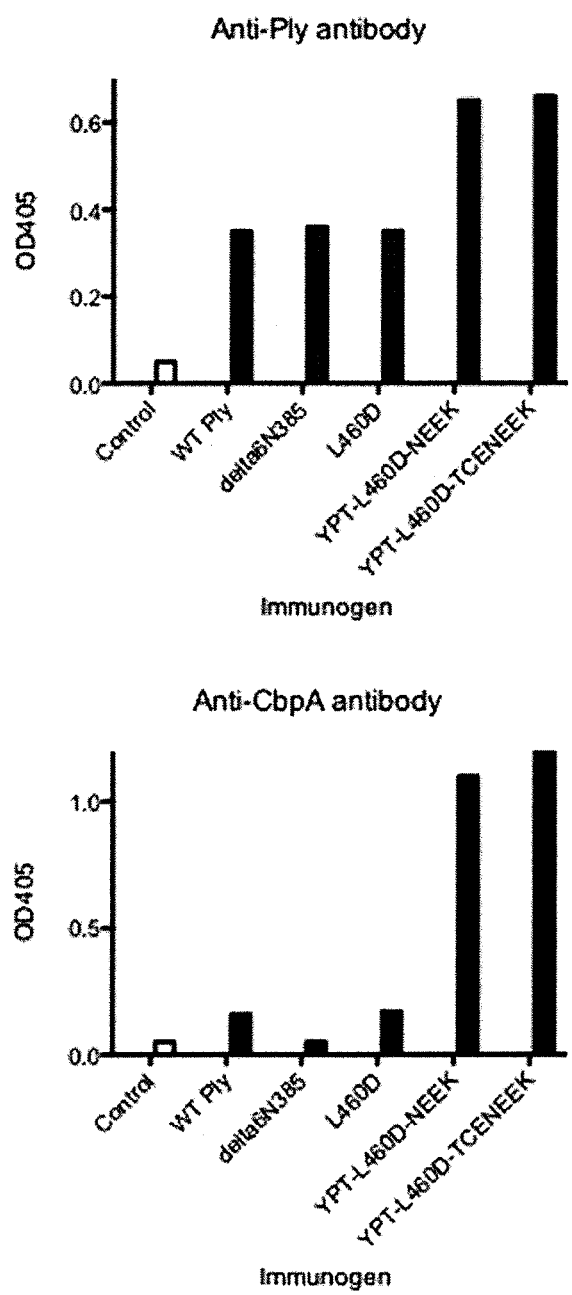
FIG. 15 shows antibody titers for various fusion proteins.

Antibody titers were determined by ELISA against plates coated overnight at 4 C with rCbpA and rPLN (100 ng/well). Serum samples were diluted 1/50, 1/150, 1/450 and 1/1050. Plates were blocked 2 hours with 10% FBS and then incubated with diluted serum for one hour at room temperature. Plates were washed 5 times and incubated 1 hour with anti-mouse IgG-AP (1:2000). Plates were washed 5× and incubated 20 minutes in AP-yellow substrate (Sigma). OD405 readings were taken. The data for 1/450 dilution is shown in FIG. 15 and indicates that the fusion construct elicits the highest antibody for both CbpA and Pin.

Figure 16:
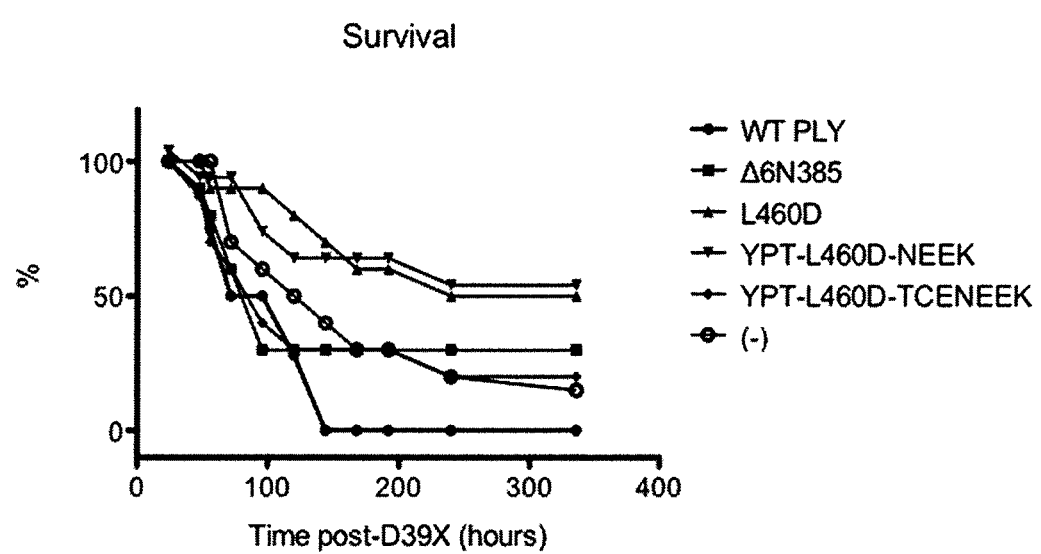
FIG. 16 shows the percent survival of the mice after challenge with various fusion proteins.

Mice were challenged with D39X ($1\times10^7$ cfu) intratracheally. Survival was monitored daily for 2 weeks. The percent survival is shown in FIG. 16.

The fusion of two peptides to L460D is protective against serotype 2 strain D39 which is a different serotype than the sequences of the immunogen. This establishes cross-serotype protection.

Conclusions from Example 3

L460D is superior to Δ6N385 as a carrier for CbpA fusion peptides in terms of immunogenicity and generation of protective antibody. Cross serotype protection was demonstrated.

Example 4: Protection from *Neisseria Meningitis*

*Neisseria meningitidis* is an important cause of meningitis. *Neisseria* and pneumococcus share binding to the same laminin receptor protein at the blood brain barrier to initiate meningitis. This property is carried by the NEEK portion of CbpA and *Neisseria* carry a protein cross reactive with NEEK. Thus, a vaccine containing NEEK might also react with *Neisseria* and prevent meningitis.

Aim:

Determine if peptide toxoid fusion confers cross protection against *Neisseria meningitis*.

Fusion Confers Protection from *Neisseria meningitis*

Mice used for this immunization were 6 week old female BalbC, 8 per group. Mice received 3 doses of antigen intraperitoneally separated by 2 week intervals (Day 1, 15, 29). For each boost 10 μg of protein was used with 100 μg adjuvant Alhydrogel (Sigma). Antigens used were as follows:

1) L460D (SEQ ID NO: 7)
2) YPT-L460D-NEEK (SEQ ID NO: 9)
3) CbpA R2 domain (SEQ ID NO: 14)
4) PBS (negative control, adjuvant alone)

Figure 17:
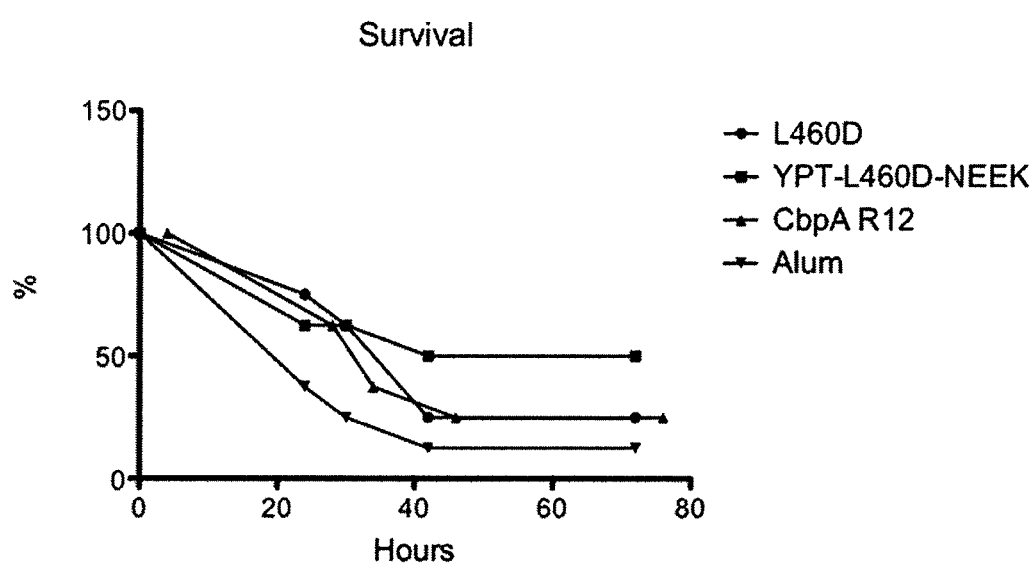
FIG. 17 shows the percent survival upon administration of various fusion proteins.

Mice were challenged intraperitoneally on day 50 with $1\times10^6$ cfu *Neisseria meningitidis* group a. Survival and presence of meningitis was monitored for 1 week. FIG. 17 shows the percent survival and indicates the fusion was protective against death by *Neisseria*. FIG. 18 shows that the fusion protein is protective against meningitis compared to toxoid alone or negative control.

Conclusion from Example 4

Peptide toxoid fusion confers significant protection across species from meningitis and death due to either pneumococcus or meningococcus.

Example 5: Protection by the Fusion Protein is Due to Toxoid Components

Aim:

Dissect protective activity to document that peptide and toxoid each contribute to protection by the fusion construct.

Two isogenic mutants were used as challenge strains to dissect protective activity. D39X expresses both toxoid and CbpA; CbpA-D39X has a deletion of CbpA. It would be expected that a vaccine would need to elicit antibodies to both toxin and CbpA to counter an infection with D39X. It would be expected that a vaccine would need to elicit antibodies only to toxin to counter an infection by a bacteria not expressing CbpA.

Mice used for this immunization were 6 week old female BalbC, 30 per group. Mice received 3 doses of antigen separated by 2 week intervals (Day 1, 15, 29). Bleeds for antibody titers (supernatant of a 75 μL bleed with heparanized capillary) were obtained by retro-orbital bleeding prior to immunization on day 1 and day 36. For each boost 10 μg of protein was used with 100 μg adjuvant Alhydrogel (Sigma). Antigens used were as follows:

1) L460D (SEQ ID NO: 7)
2) YPT-L460D-NEEK (SEQ ID NO: 9)
3) PBS (−) (adjuvant alone)

Mice were challenged on day 50 with $1\times10^7$ cfu of either D39X or an isogenic mutant CbpA−/D39X (10 mice from each immunized group used per strain). No differences were seen in the course or titer of the two strains of bacteria in blood. Survival was monitored daily for 2 weeks. As shown in FIG. 19, fusion toxoid showed enhanced survival protection over L460D alone when both pneumolysin and CbpA were on the bacteria (i.e. D39X). Fusion was not better than L460D alone if there was no CbpA on the bacteria (CbpA-D39X). These differences indicate that the toxoid and the CbpA peptide components of the fusion both contribute to protection.

Conclusion from Example 5

Both parts of the fusion construct, the peptides and the carrier, contribute to the protective activity of the vaccine when wild type bacteria expressing both CbpA and Pln are the challenge.

Example 6: Efficacy of Peptide-Toxoid Fusion in Colonization Model

Pneumococci initiate infection by colonizing the nasopharynx before spreading to the lung or blood. A vaccine that could prevent colonization would be desirable. The YPT portion of the fusion vaccine is designed to block translocation of bacteria from the nasopharynx to the lung/blood. For vaccines to have activity on a mucosal surface such as the nasopharynx, they typically need to be administered to the mucosa directly, i.e. intranasally. A vaccine that could elicit protection from colonization even when given parenterally would be desirable.

Aim:
Determine if immunization with peptide-toxoid fusion intraperitoneally (IP) decreases colonization of the nasopharynx.

Fusion Active Against Colonization (Data from Two Experiments)

Mice used for this immunization were 6 week old female BalbC, 7 per group. Mice received 3 doses of antigen intraperitoneally separated by 2 week intervals (Day 1, 15, 29). For each boost 10 μg of protein was used with 100 μg adjuvant Alhydrogel (Sigma). Antigens used were as follows:

1) L460D (SEQ ID NO: 7)
2) YPT-L460D-NEEK (SEQ ID NO: 9)
3) CbpA R2 (SEQ ID NO: 14)
4) PBS (−) (adjuvant alone)

Mice were infected intranasally on day 50 with $1.5\times10^7$ cfu T4X. Nasal lavages were taken at 24, 48, 72 and 96 hours and plated for bacterial numbers to indicate extent of colonization. Results are shown in Table 2.

TABLE 2

| Log CFU in nasopharyngeal wash following IP vaccine | | | | |
|---|---|---|---|---|
| | L460D | YPT-L460D-NEEK | CbpA R2 | PBS(−) |
| Exp 1 48 h | 5.8 | 6.5 | 6.4 | 6.0 |
| 96 h | 5.6 | 4.9* | 4.8* | >8 |

TABLE 2-continued

| Log CFU in nasopharyngeal wash following IP vaccine | | | | |
|---|---|---|---|---|
| | L460D | YPT-L460D-NEEK | CbpA R2 | PBS(−) |
| Exp 2 48 h | 5.7 | 6.3 | 6.2 | 6.0 |
| 96 h | 5.7 | 5.2* | 5.1 | >8 |

*Significant difference between 48 h and 96 h

Conclude:
Negative control animals (PBS) experienced a 2.5 log increase in bacterial titer in nasopharynx between 48 to 96 h. L460D animals stayed the same as original inoculum. CbpA R2 (positive control) and YPT-L460D-NEEK decreased nasopharyngeal baterial numbers by 1.5 logs and were 3 logs less than PBS control at 96 h.

Conclusion for Example 6

IP immunization with peptide-toxoid fusion prevents growth of bacteria in model of colonization of the nasopharynx.

Significance:
Activity in controlling colonization of the nasopharynx is detectable for YPT-L460D-NEEK even with immunization IP.

Example 7: Does Protection in the Nasopharynx Arise from IL-17 T Cells and/or B Cells in Nasal Associated Lymphoid Tissue (NALT) Post Immunization Protection from systemic diseases is believed to be due to antibody mediated defenses. On mucosal surfaces such as the nasopharynx, T cells and B cells cooperate. In particular IL-17 is believed to be important in recruiting cells to the nasopharynx to eliminate colonization. To measure T and B cells in the nose, the NALT must be harvested and cells separated to enumerate and determine specific cell markers for identification. In our model, NALT contains ~2% T cells producing IL-17 in naïve colonized mice and IL-17 cytokine production peaks at day 10 post immunization.

Method to Quantitate NALT T Cells Post Vaccine:

Groups of 5 mice were immunized either intranasally or intraperitoneally 3 times in two week intervals with L460D, YPT-L460D-NEEK fusion, or CbpA R12. Adjuvant was cholera toxin (CT, not heat inactivated). For the CT alone group, NALT was harvested before final boost for baseline. For remaining groups, NALT and spleen were harvested 10 days after the final boost and assayed by Harvest of NALT yeilded ~$5\times10^5$ T cells, a value in range of previous controls in naïve and colonized mice. Spleens yielded $1\times10^7$ cells. 100,000 cells were counted and tested by:

1) FACS for pneumcoccal-reactive T cells bearing $CD4^+$, $CD19^+$ or $IL-17^+$
2) ELISPOT for B cells making antibody to CbpA or Pln T Cell Characteristics from NALT and Spleen Results are shown in Table 3 and show that immunization IN with CbpA or the fusion invoked a small increase in IL-17 T cells compared to CT alone only in NALT. This was greater than if immunization was IP.

TABLE 3

Characteristics of T cells elicited by fusion vaccine

| | % T Cells + for IL-17 | |
|---|---|---|
| | NALT | Spleen |
| CbpA IN | 3.8 | 0.2 |
| L460D IN | 2.1 | 0.2 |
| Fusion IN | 3.3 | 0.2 |
| CT alone IN | 2.9 | 0.2 |
| CbpA IP | 0.6 | 0.2 |
| L460D IP | 2.1 | 0.3 |
| Fusion IP | 2.6 | 0.2 |
| CT alone IP | 2.3 | 0.2 |

Figure 20:
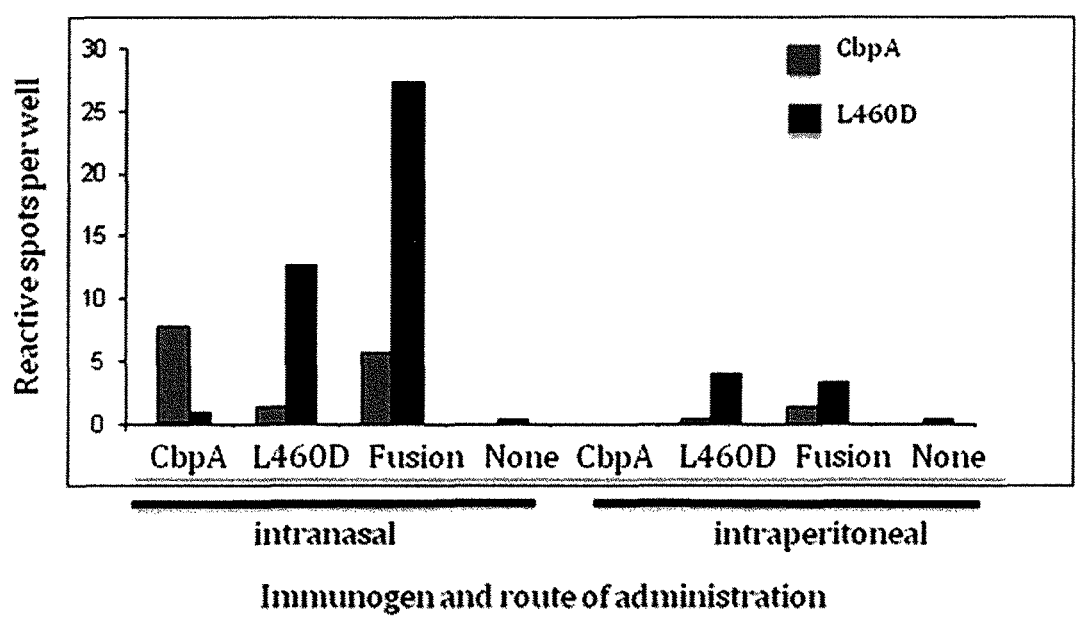
FIG. 20 shows the number of positive spots per well reactive to CbpA or pneumolysin.

B Cell Results:

ELISPOT: $1 \times 10^5$ B cells were seeded per well of a 96 well plate. Cells were incubated with antigen (CbpA or L460D) and antibody production in response to stimulation by specific antigen was indicated by development of colored spots. Maximum is ~40 spots/filter. The data (number of positive spots per well reactive to CbpA or L460D) is set forth in FIG. 20 as a function of 4 immunizing antigens, given by 2 routes.

B cells in NALT were strongest with intranasal route of immunization. However, it is notable that reactive B cells were detected even after intraperitoneal immunization with L460D and Fusion. Fusion induced strong response to CbpA as expected but also strong to pneumolysoid.

Conclusion from Example 7

The fusion construct elicits a small increase in IL-17⁺ T cells and a strong increase in B cells reactive for anti-CbpA and anti-pneumolyin in the NALT. More activity was seen with IN than IP administration.

Example 8: CbpA-Pneumolysin Fusion Protein Expressed/Purified from Tagless Vector For vaccines used in humans, constructs that do not express a tag such as poly-histidine are desired.

YPT-L460D-NEEK was amplified from the pet33 construct using oligos YPTNDE (cgcgcgcgcatatggcttg-taaaaaagccgagg) (SEQ ID NO: 37) and NEEKSAC (SEQ ID NO: 38). The PCR product was cut overnight with NdeI and SacI and ligated into prepared tagless vector pET27b. Clones were sequenced by the St. Jude Children's Research Hospital Hartwell Center. Clones containing the correct sequence were transformed into BL21(DE3) competent cells. Protein expression/purification was carried out by St Jude Children's Research Hospital's Protein Production Facility.

Test Constructs Using Tagless CbpA Pneumolysin Fusion

Mice used for this immunization were 6 week old female BalbC, at least 40 per group in total, (i.e. 10 per group) in multiple experiments. Mice received 3 doses of antigen separated by 2 week intervals (Day 1, 15, 29). Bleeds for antibody titers (supernatant of a 75 µL bleed with heparanized capillary) were obtained by retro-orbital bleeding prior to immunization on day 1 and day 36.

For each boost 10 µg of protein was used with 100 µg adjuvant Alhydrogel (Sigma). Antigens used were as follows:

1) YPT-L460D-NEEK (SEQ ID NO: 9)
2) L460D-NEEK (SEQ ID NO: 25)
3) PBS (−) (adjuvant alone)

Mice were challenged on day 50 with $1 \times 10^7$ cfu T4X intratracheally. Meningitis was determined by physical attributes (spinning of the head) and collection of cerebrospinal fluid (CSF) for bacterial number. Survival was monitored daily for 2 weeks. The data is summarized in FIG. 21 and then shown for each mouse in FIGS. 22 to 25.

Figure 22:
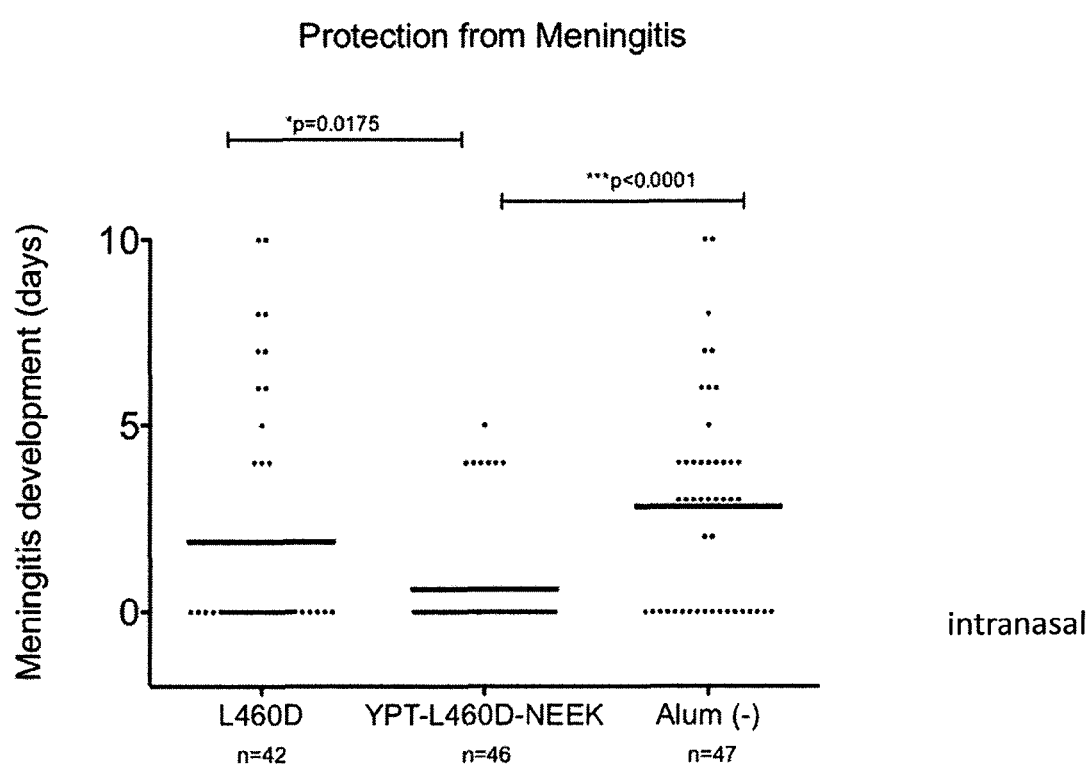
FIG. 22 provides data showing the frequency and time to development of meningitis.
Figure 23:
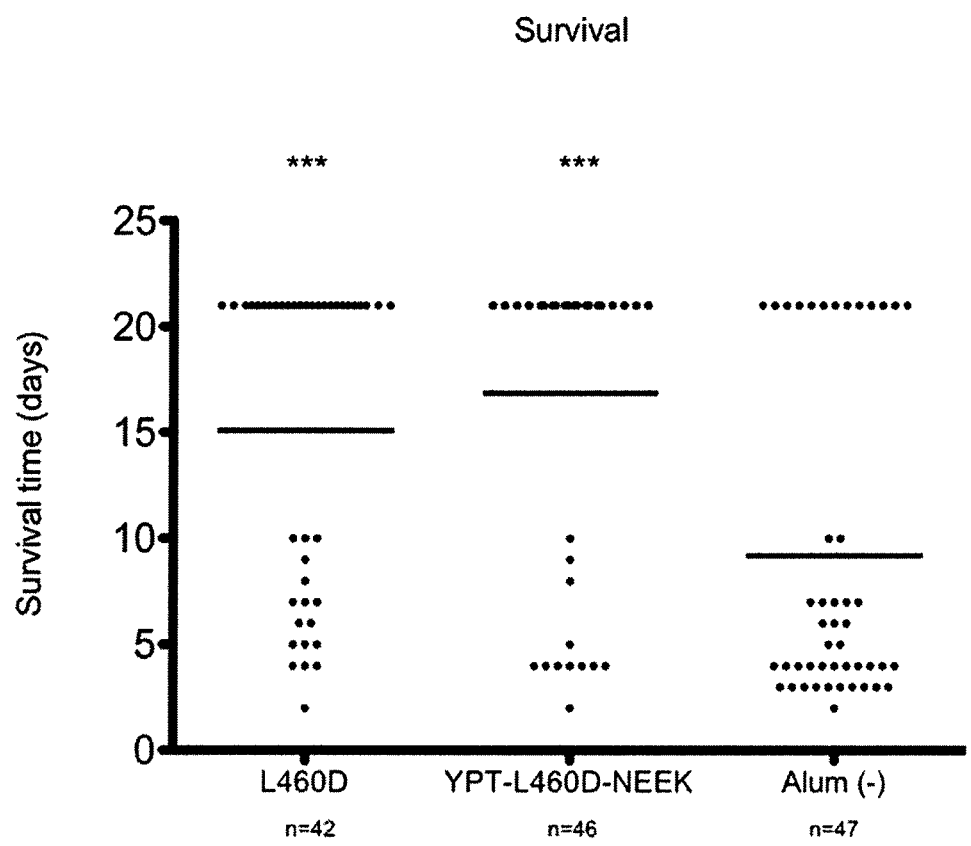
FIG. 23 provides data showing the survival time for mice immunized with L460D, YPT-L460D-NEEK or Alum (−) control.

As shown in FIG. 22, mice immunized with YPT-L460D-NEEK had a significantly lower incidence of meningitis than mice immunized with L460D toxoid or adjuvant alone. As shown in FIG. 23, mice immunized with YPT-L460D-NEEK or L460D toxoid were protected similarly and both were significantly better than adjuvant alone.

Figure 24:
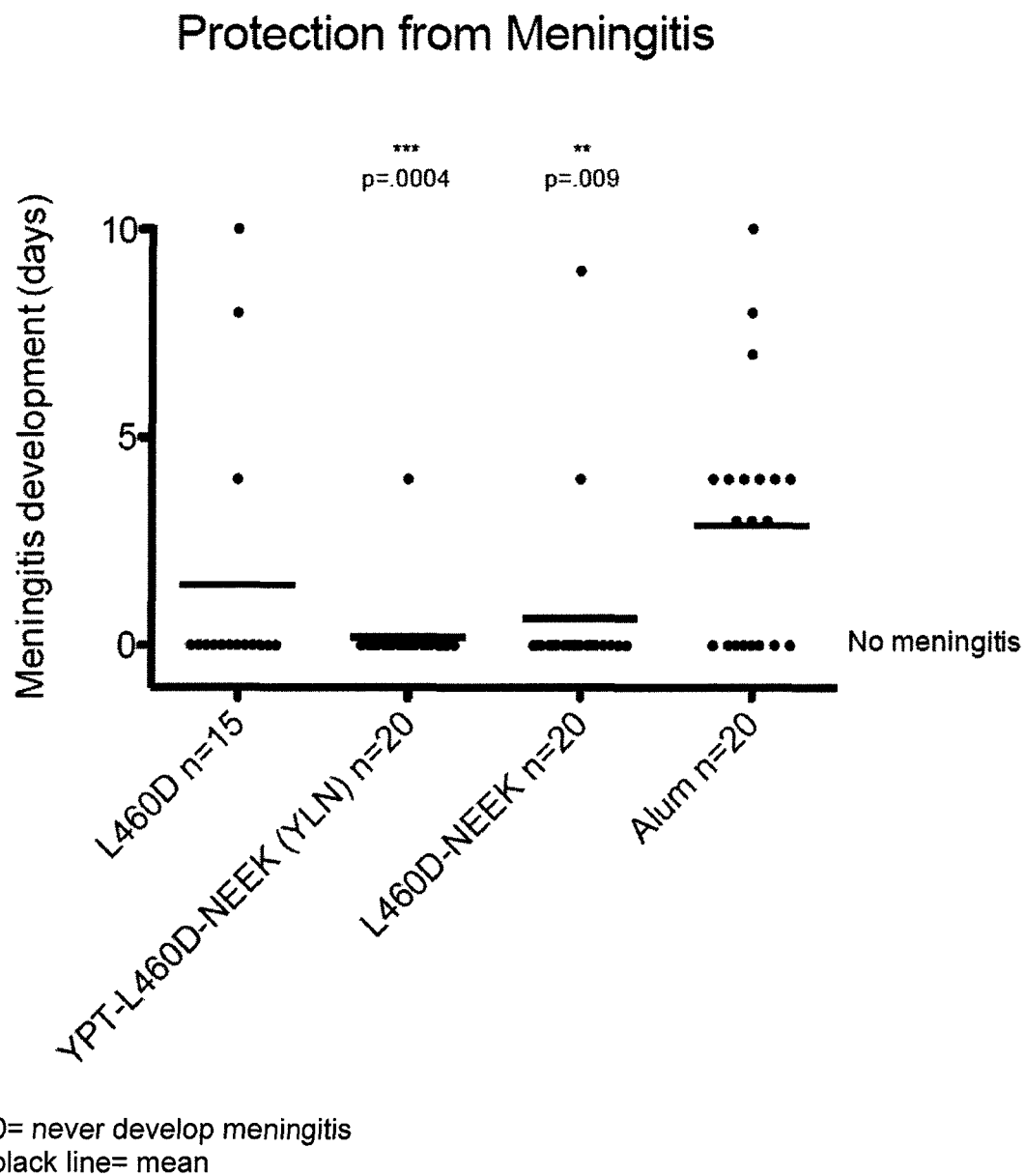
FIG. 24 shows mice immunized with YPT-L460D-NEEK or L460D were protected similarly and both were significantly better than adjuvant alone.

As shown in FIG. 24, mice immunized with YPT-L460D-NEEK had a significantly lower incidence of meningitis than mice immunized with L460D toxoid or adjuvant alone.

Figure 25:
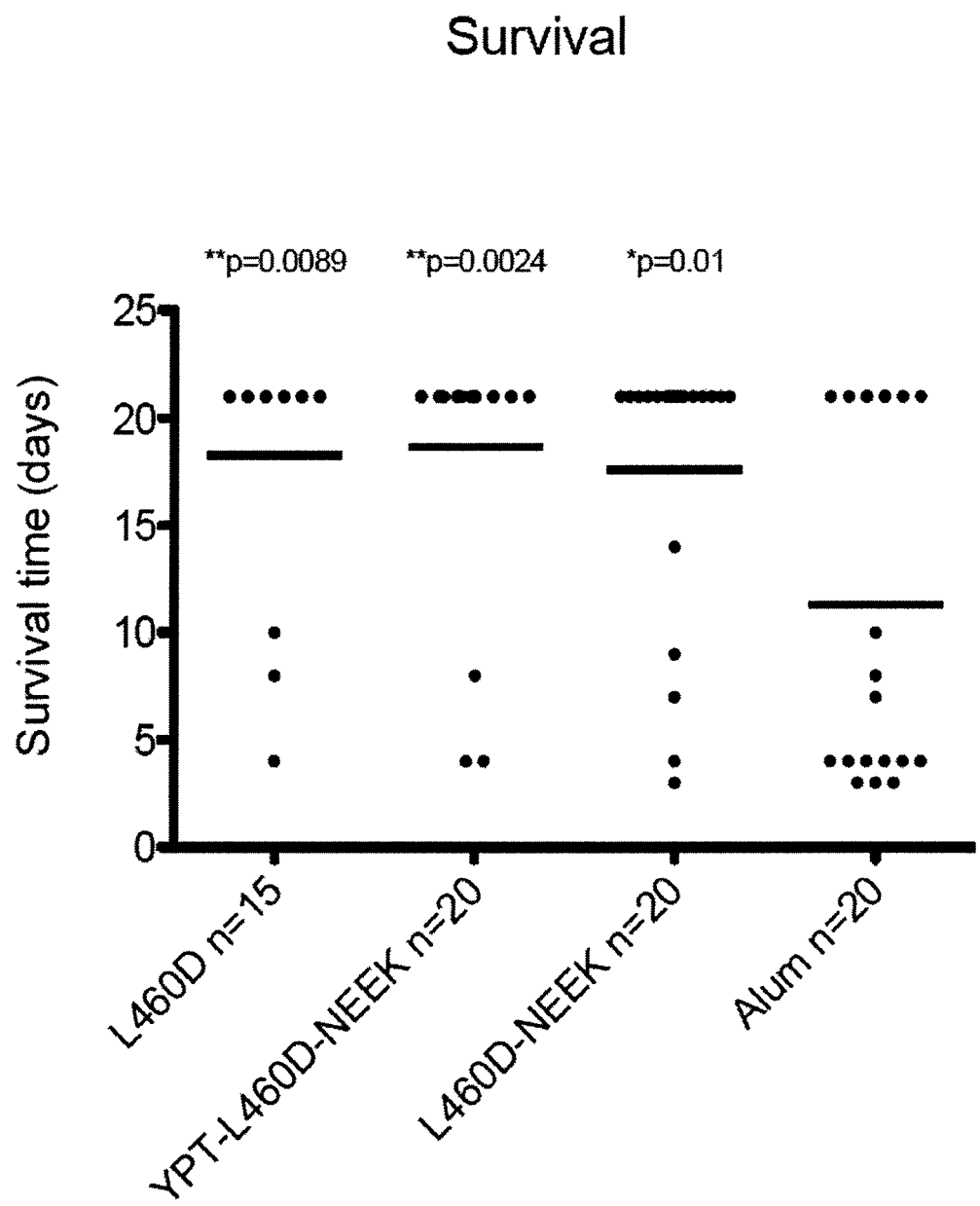
FIG. 25 L460D and YPT-L460D-NEEK show best protection followed by L460D-NEEK.

As shown in FIG. 25, L460D and YPT-L460D-NEEK show excellent protection followed by L460D-NEEK.

Conclusion from Example 8

YPT-L460D-NEEK and L460-NEEK were significantly better than L460D alone in preventing meningitis and death.

Example 9: Test Pneumolysoids Δ6N385 and L460D and their Fusions for Residual Hemolytic Activity and Determine if they Elicit Antibody Neutralizing Toxin-Induced Hemolysis For use in humans, the pneumolysoids must be nontoxic and generate antibody that can neutralize the hemolytic (cytotoxic) activity of the wild type toxin. The fusion must not increase toxic activity.

Aim:

Quantify residual toxic activity of toxoids and whether fusion alters this property. Determine relative ability of toxoids±fusions to elicit antibody capable of neutralizing toxic activity of native Pneumolysin.

Toxoid Constructs Remained Nonhemolytic

Figure 26:
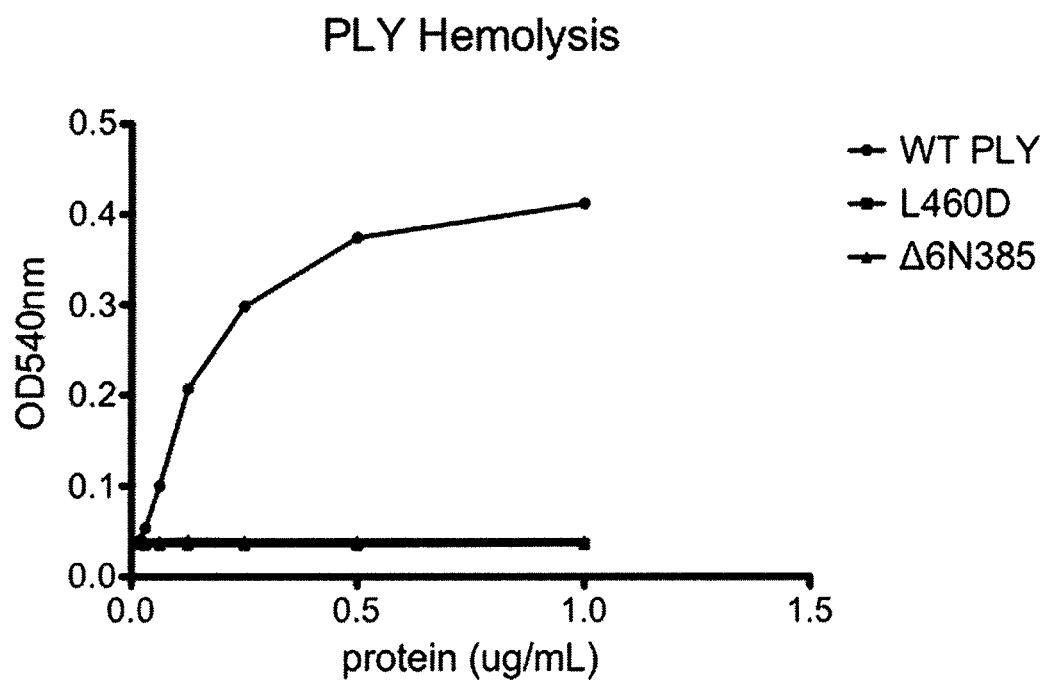
FIG. 26 shows data demonstrating toxoid constructs remained nonhemolytic.

Recombinant proteins were tested for hemolytic activity against sheep red blood cells. Proteins were diluted to 10 µg/m concentration in PBS. Protein was then serial diluted 1:2 with a starting concentration of 1 µg/m in dilution buffer (10 ml PBS, 0.01 g BSA, 0.015 g DTT) in a 96 well V-bottom plate. 50 µL from each well was transferred to a fresh V-bottom plate. 1 ml of defibrinated sheep blood was washed 3× in 10 ml PBS (blood was centrifuged 5 minutes at 1000×g). 50 µL blood was added to each well containing protein and the plate was incubated 30 minutes at 37° C. The plate was centrifuged 3 minutes at 1000×g and supernatant was transferred to a 96 well ELISA plate. OD540 readings were taken with a plate reader. 1% Triton X-100 was used as a positive control with dilution buffer as the negative control. The experiment was repeated twice and the results combined and shown in FIG. 26. Wild type pneumolysin is hemolytic and this activity titrates out with dilution. L460D and Δ6N385 are non-hemolytic even at high concentrations. Fusions show same profile as the pneumolysoid on which they are attached.

Pneumolysin Neutralization Assays Using Antisera from Immunized Mice

Figure 27:
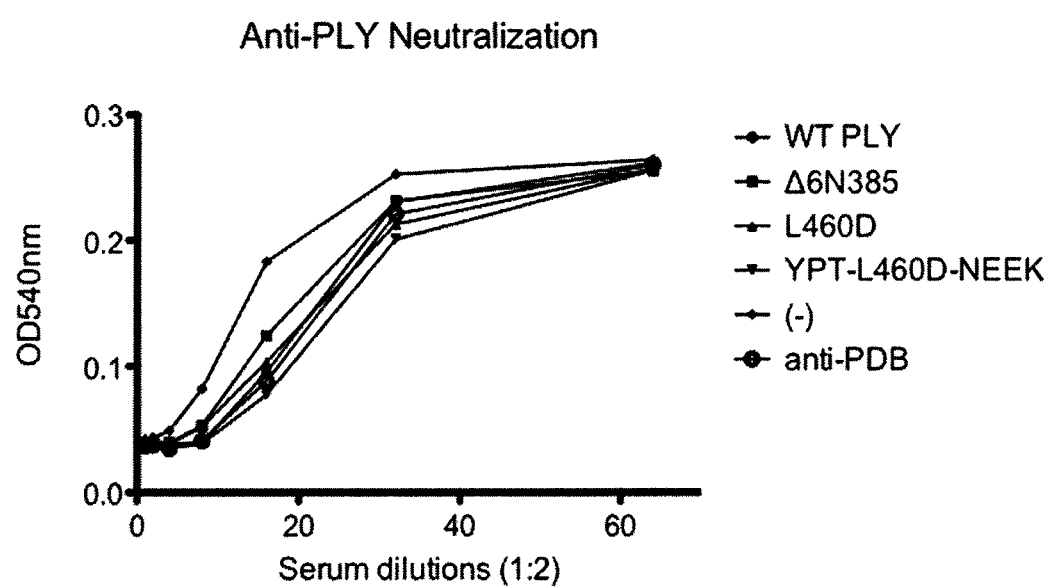
FIG. 27 shows pneumolysin neutralization assays using antisera from immunized mice.

Serum samples from immunized mice were tested for anti-hemolytic activity with wild type pneumolysin. Briefly, 1.2 µL serum was mixed with 6 µL 10% glycerol and 52.8 µL PBS 1 hour at room temperature to remove inhibitory cholesterol. Samples were spun 5 minutes at 10,000×g and 50 µL supernatant was transferred to a V-bottom plate. Samples were heat inactivated at 56° C. for 30 minutes to remove complement. Make 2-fold serial dilutions of sera in PBS and add 50 μL wild type pneumolysin (4 hemolytic units). Incubate 15 minutes at 37° C. Prepare 1% rabbit blood by washing 1 ml blood in 10 mls PBS 3 times. Add 0.001% beta-mercaptoethanol to final volume of blood. Add 50 μL to each well and incubate 30 minutes at 37° C. Spin plates 3 minutes at 1000×g and transfer 60-80 μL to fresh ELISA plate. Read absorbance at 540 nm. Anti-PdB antiserum was used as the positive control and results are shown in FIG. 27. Titer of antibody neutralizing wild type toxin hemolytic activity was greatest after immunizing with YPT-L460D-NEEK more so than L460D which was more so than Δ6N385.

The article "a" and "an" are used herein to refer to one or more than one (i.e., to at least one) of the grammatical object of the article. By way of example, "an element" means one or more element.

TABLE 4

| SEQ ID NO: | AA/NT | Description |
|---|---|---|
| 1 | AA | R2$_1$ fragment sequence of CbpA of S. pneumoniae |
| 2 | AA | R2$_2$ fragment sequence of CbpA of S. pneumoniae |
| 3 | AA | Cysteine mutant of R2$_1$ fragment sequence of S. pneumoniae (AKA "YPT"; looped) |
| 4 | AA | Cysteine mutant of R2$_2$ fragment sequence of S. pneumoniae (AKA "NEEK"; looped) |
| 5 | AA | Wild-type pneumolysin amino acid sequence of S. pneumoniae (AKA "PLY") |
| 6 | NT | Wild-type pneumolysin nucleotide sequence of S. pneumoniae |
| 7 | AA | L460D pneumolysoid sequence |
| 8 | AA | Δ6N385 pneumolysoid sequence |
| 9 | AA | YPT-L460D-NEEK fusion protein sequence |
| 10 | NT | YPT-L460D-NEEK fusion protein nucleotide sequence |
| 11 | AA | YPT-Δ6N385-NEEK fusion protein sequence |
| 12 | AA | Full-length CbpA amino acid sequence of S. pneumoniae |
| 13 | AA | CbpA R1R2 amino acid sequence of S. pneumoniae |
| 14 | AA | R2 domain amino acid sequence of CbpA of S. pneumoniae |
| 15 | AA | TCE1 sequence |
| 16 | AA | TCE2 sequence |
| 17 | AA | PdB pneumolysoid amino acid sequence |
| 18 | AA | PdB-2TCEs-linear NEEK fusion protein sequence |
| 19 | AA | Looped YPT-PdB-2 TCEs-linear NEEK fusion protein sequence |
| 20 | AA | Δ6N385-NEEK fusion protein sequence |
| 21 | AA | Δ6N385-TCE-NEEK fusion protein sequence |
| 22 | AA | YPT-Δ6N385 fusion protein sequence |
| 23 | AA | YPT-Δ6N385-TCE-NEEK fusion protein sequence |
| 24 | AA | YPT-L460D-TCE-NEEK fusion protein sequence |
| 25 | AA | L460D-NEEK fusion protein sequence |
| 26 | NT | JAT201 primer |
| 27 | NT | C-term Fusion primer |
| 28 | NT | JAT209 primer |
| 29 | NT | JAT210 primer |
| 30 | NT | Construct 2 primer |
| 31 | NT | PLYNde1 primer |
| 32 | NT | NEEKSac1 primer |
| 33 | NT | YPT primer |
| 34 | NT | JAT201b primer |
| 35 | NT | TCENEEK2 primer |
| 36 | NT | JAT215 primer |
| 37 | NT | YPTNDE primer |
| 38 | NT | NeekSac primer |
| 39 | AA | L460D pnemolysoid variant sequence |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polynucleotide that encodes a fusion protein, said fusion protein comprising a) a first polypeptide having at least 90% sequence identity to the amino acid sequence of SEQ ID NO: 3 or SEQ ID NO: 4, wherein said first polypeptide forms a loop conformation and is immunogenic, b) a second polypeptide, fused in frame to said first polypeptide, said second polypeptide comprises at least one T cell epitope (TCE), and c) a third polypeptide comprising an amino acid sequence having at least 90% sequence identity to SEQ ID NO:3 or SEQ ID NO:4, wherein said third polypeptide forms a loop conformation and is immunogenic;

and wherein said fusion protein comprises said first, said second and said third polypeptide in the following order: said first polypeptide operably linked to said second polypeptide operably linked to said third polypeptide and wherein said second polypeptide is heterologous to said first and said third polypeptides.

2. An expression cassette comprising the polynucleotide according to claim 1, operably linked to a promoter.

3. A vector comprising the expression cassette of claim 2.

4. The isolated polynucleotide of claim 1, wherein said first polypeptide comprises the amino acid sequence of SEQ ID NO: 3 or SEQ ID NO: 4.

5. The isolated polynucleotide of claim 1, wherein said third polypeptide comprises the amino acid sequence of SEQ ID NO: 3 or SEQ ID NO: 4.

6. The isolated polynucleotide of claim 1, wherein said second polypeptide comprises an immunogenic pneumococcal polypeptide.

7. The isolated polynucleotide of claim 1, wherein said second polypeptide comprises a pneumolysoid.

8. The isolated polynucleotide of claim 7, wherein said pneumolysoid comprises:

(a) the amino acid sequence set forth in SEQ ID NO:7 or a sequence having at least 90% sequence identity to SEQ ID NO:7 and is immunogenic; or (b) the amino acid sequence set forth in SEQ ID NO:8 or a sequence having at least 90% sequence identity to SEQ ID NO:8 and is immunogenic; or (c) the amino acid sequence set forth in SEQ ID NO:17 or a sequence having at least 90% sequence identity to SEQ ID NO:17 and is immunogenic.

9. The isolated polynucleotide of claim 1, wherein (a) said first polypeptide comprises the amino acid sequence of SEQ ID NO:3, said second polypeptide comprises the amino acid sequence of SEQ ID NO:7, and said third polypeptide comprises the amino acid sequence of SEQ ID NO:4; or (b) said first polypeptide comprises the amino acid sequence of SEQ ID NO:4, said second polypeptide comprises the amino acid sequence of SEQ ID NO:7, and said third polypeptide comprises the amino acid sequence of SEQ ID NO:3.

10. The isolated polynucleotide of claim 1, wherein said fusion protein comprises the amino acid sequence of SEQ ID NOS: 9 or 11 or has at least 90% sequence identity to the amino acid sequence set forth in SEQ ID NOS: 9 or 11.

* * * * *